(12) United States Patent
Tsutsui

(10) Patent No.: US 10,071,211 B2
(45) Date of Patent: Sep. 11, 2018

(54) INTRANASAL DELIVERY DEVICES

(75) Inventor: Tatsuo Tsutsui, Yokohama (JP)

(73) Assignee: SHIN NIPPON BIOMEDICAL LABORATORIES, LTD., Kagoshima (JP)

(*) Notice: Subject to any disclaimer, the term of this patent is extended or adjusted under 35 U.S.C. 154(b) by 686 days.

(21) Appl. No.: 13/982,461

(22) PCT Filed: Jan. 31, 2012

(86) PCT No.: PCT/JP2012/000620
§ 371 (c)(1),
(2), (4) Date: Nov. 18, 2013

(87) PCT Pub. No.: WO2012/105236
PCT Pub. Date: Aug. 9, 2012

(65) Prior Publication Data
US 2014/0060535 A1    Mar. 6, 2014

Related U.S. Application Data

(60) Provisional application No. 61/437,994, filed on Jan. 31, 2011.

(51) Int. Cl.
*A61M 15/08* (2006.01)
*A61M 11/02* (2006.01)
(Continued)

(52) U.S. Cl.
CPC .......... *A61M 15/08* (2013.01); *A61M 11/02* (2013.01); *A61M 15/0028* (2013.01);
(Continued)

(58) Field of Classification Search
CPC .......... A61M 15/0005; A61M 15/0006; A61M 15/0008; A61M 15/0028; A61M 15/003;
(Continued)

(56) References Cited

U.S. PATENT DOCUMENTS 2,307,986 A * 1/1943 Brown ............... A61M 13/00
                                                604/201
2,581,182 A * 1/1952 Fields ............... A61M 15/0065
                                                128/203.15
(Continued)

FOREIGN PATENT DOCUMENTS

CN    1161866 A    10/1997
EP    1390091 B1    1/2009
(Continued)

OTHER PUBLICATIONS

International search report and written opinion dated May 22, 2012 for PCT/JP2012/000620.
(Continued)

*Primary Examiner* — Annette Dixon
(74) *Attorney, Agent, or Firm* — Wilson, Sonsini, Goodrich & Rosati

(57) ABSTRACT

Devices for delivery of dry powder formulations are also provided. Devices can be single-use devices. Formulations and methods of manufacture are provided for dry powder compositions suitable for intranasal administration. Also provided are methods of use for preventing or controlling emesis and other diseases and disorders and devices, compositions, and methods for nasal delivery of therapeutic formulations.

20 Claims, 13 Drawing Sheets

(51) Int. Cl.
*A61M 16/00* (2006.01)
*A61M 15/00* (2006.01)

(52) U.S. Cl.
CPC .... *A61M 15/0043* (2014.02); *A61M 16/0045* (2013.01); *A61M 2202/064* (2013.01); *A61M 2205/075* (2013.01); *A61M 2206/16* (2013.01)

(58) Field of Classification Search
CPC .......... A61M 15/0031; A61M 15/0043; A61M 15/0061; A61M 15/08; A61M 2202/064; A61M 2205/075; A61M 2206/16; A61M 1/0003; A61M 1/0072; A61M 11/00; A61M 11/001; A61M 11/003; A61M 11/005; A61M 11/007; A61M 11/008; A61M 11/02; A61M 11/06; A61M 13/00; A61M 15/00; A61M 15/0015; A61M 15/0018; A61M 15/002; A61M 15/0021; A61M 15/0025; A61M 15/0035; A61M 15/0036; A61M 15/0038; A61M 15/004; A61M 15/0041; A61M 15/0045; A61M 15/0048; A61M 15/005; A61M 15/0051; A61M 15/0055; A61M 15/0065; A61M 15/0066; A61M 15/0068; A61M 15/0086; A61M 15/0088; A61M 15/009; A61M 15/0091; A61M 15/0096; A61M 15/0098; A61M 15/06; A61M 15/085; A61M 16/00; A61M 16/0866; A61M 16/1055; A61M 16/1065; A61M 16/1075; A61M 16/208; A61M 2005/31508; A61M 2016/0021; A61M 2016/0039; A61M 2202/04; A61M 2202/0468; A61M 2202/062; A61M 2202/30; A61M 2205/0233; A61M 2205/071; A61M 2205/073; A61M 2205/13; A61M 2205/43; A61M 2205/581; A61M 2205/583; A61M 2205/59; A61M 2205/8218; A61M 2205/8225; A61M 2206/10; A61M 2206/14; A61M 2209/06; A61M 2210/0618; A61M 2210/0625; A61M 2210/0668; A61M 2230/005; A61M 2230/43; A61M 3/0233; A61M 3/0279; A61M 31/00; B05B 11/041; B05B 11/045; B05B 11/06; B05B 11/062; A61B 5/085; A61B 5/097; A61B 5/415; A61B 17/24; A61B 18/12; A61B 18/14; A61B 18/1206; A61B 2018/0066; A61B 5/4839; A61F 5/08; A61J 1/067
USPC ................. 239/327, 399, 403; 222/630–633; 128/200.14, 200.18, 200.21, 200.22, 128/200.23, 200.24, 203.12, 203.15, 128/203.18, 203.19, 203.21, 203.22, 128/203.28, 204.12, 206.11, 207.18
See application file for complete search history.

(56) References Cited

U.S. PATENT DOCUMENTS

| | | | | |
|---|---|---|---|---|
| 3,506,162 A * | 4/1970 | Schwartzman | ....... | B05B 11/047 222/207 |
| 3,522,659 A * | 8/1970 | Welch | ....... | A61M 11/02 34/443 |
| 3,656,660 A * | 4/1972 | Mueller | ....... | B05B 11/004 222/212 |
| 3,856,185 A | 12/1974 | Riccio | | |
| 4,017,007 A | 4/1977 | Riccio | | |
| 4,069,819 A * | 1/1978 | Valentini | ....... | A61M 15/0028 128/203.15 |
| 4,200,099 A | 4/1980 | Guenzel et al. | | |
| 4,358,028 A | 11/1982 | Chiquiar-Arias | | |
| 5,046,493 A | 9/1991 | Kropkowski et al. | | |
| 5,067,655 A * | 11/1991 | Farago | ....... | B05B 1/3478 239/124 |
| 5,215,221 A * | 6/1993 | Dirksing | ....... | A61J 1/067 169/30 |
| 5,224,471 A * | 7/1993 | Marelli | ....... | B05B 11/0005 128/200.14 |
| 5,328,099 A * | 7/1994 | Petit | ....... | A61M 11/02 128/200.14 |
| 5,429,122 A * | 7/1995 | Zanen | ....... | A61M 15/0065 128/200.22 |
| 5,647,349 A * | 7/1997 | Ohki | ....... | A61M 15/0028 128/203.12 |
| 5,683,361 A | 11/1997 | Elk et al. | | |
| 5,702,362 A | 12/1997 | Herold et al. | | |
| 5,810,004 A * | 9/1998 | Ohki | ....... | A61M 15/0028 128/203.15 |
| 6,089,228 A | 7/2000 | Smith et al. | | |
| 6,136,346 A * | 10/2000 | Eljamal | ....... | A61K 9/0075 424/488 |
| 6,158,676 A * | 12/2000 | Hughes | ....... | A61M 11/06 239/337 |
| 6,186,141 B1 | 2/2001 | Pike et al. | | |
| 6,290,667 B1 | 9/2001 | Cook | | |
| 6,345,737 B1 | 2/2002 | Martin et al. | | |
| 6,398,077 B1 * | 6/2002 | Gross | ....... | B65D 47/2031 222/145.1 |
| 6,427,680 B1 | 8/2002 | Oechsel | | |
| 6,443,152 B1 * | 9/2002 | Lockhart | ....... | A61M 15/0028 128/200.14 |
| 6,488,648 B1 | 12/2002 | Matsugi et al. | | |
| 6,494,204 B1 | 12/2002 | Ponce | | |
| 6,543,448 B1 | 4/2003 | Smith et al. | | |
| 6,585,172 B2 | 7/2003 | Arghyris | | |
| 6,644,305 B2 | 11/2003 | Macrae et al. | | |
| 6,824,080 B2 | 11/2004 | Matsugi et al. | | |
| 6,866,039 B1 * | 3/2005 | Wright | ....... | A61M 15/0028 128/203.15 |
| 6,938,798 B2 | 9/2005 | Stradella | | |
| 7,063,686 B2 * | 6/2006 | Mezzoli | ....... | A61H 35/04 128/200.14 |
| 7,220,457 B2 * | 5/2007 | Anderson | ....... | B05B 7/10 239/406 |
| 7,278,982 B2 | 10/2007 | Tsutsui | | |
| 7,353,823 B2 * | 4/2008 | Tsutsui | ....... | A61M 15/0028 128/203.15 |
| 7,438,700 B2 | 10/2008 | Ishizeki et al. | | |
| 7,481,218 B2 | 1/2009 | Djupesland | | |
| 7,703,620 B2 * | 4/2010 | Rand | ....... | A61M 15/0045 220/23.2 |
| 7,713,518 B2 * | 5/2010 | Rand | ....... | A61M 15/0028 128/203.12 |
| 7,934,503 B2 * | 5/2011 | Djupesland | ....... | A61M 15/0028 128/203.21 |
| 8,056,762 B2 * | 11/2011 | Wright | ....... | A61M 15/0028 222/209 |
| 8,302,823 B2 * | 11/2012 | Lim | ....... | B65D 35/46 222/212 |
| 8,517,009 B2 * | 8/2013 | Kakade | ....... | A61M 15/009 128/200.18 |
| 8,827,946 B2 * | 9/2014 | Tsutsui | ....... | A61K 9/0043 604/212 |
| 2002/0174865 A1 | 11/2002 | Brian, Jr. et al. | | |
| 2004/0112378 A1 | 6/2004 | Djupesland | | |
| 2004/0149289 A1 | 8/2004 | Djupesland | | |
| 2004/0176719 A1 | 9/2004 | Ishizeki et al. | | |
| 2004/0187868 A1 | 9/2004 | Hochrainer et al. | | |
| 2005/0177095 A1 | 8/2005 | Tsutsui | | |
| 2006/0024185 A1 | 2/2006 | Akerman | | |
| 2006/0062740 A1 * | 3/2006 | Rand | ....... | A61M 15/0028 424/46 |
| 2006/0191931 A1 * | 8/2006 | Rand | ....... | A61M 15/0045 220/23.4 |

(56) References Cited

U.S. PATENT DOCUMENTS

| | | |
|---|---|---|
| 2006/0219240 A1 | 10/2006 | Djupesland |
| 2006/0254585 A1* | 11/2006 | Ishizeki .............. A61M 11/02 128/203.21 |
| 2007/0129665 A1 | 6/2007 | Dickens et al. |
| 2008/0142018 A1 | 6/2008 | Doshi et al. |
| 2008/0161771 A1 | 7/2008 | Djupesland |
| 2008/0289629 A1 | 11/2008 | Djupesland et al. |
| 2009/0025720 A1 | 1/2009 | Chen |
| 2009/0064997 A1 | 3/2009 | Li |
| 2010/0175698 A1 | 7/2010 | Rand |

FOREIGN PATENT DOCUMENTS

| | | |
|---|---|---|
| GB | 2400565 A | 10/2004 |
| GB | 2418147 A | 3/2006 |
| GB | 2472327 A | 2/2011 |
| JP | H 0871152 A | 3/1996 |
| JP | H 08103499 A | 4/1996 |
| JP | H 08206208 A | 8/1996 |
| JP | H 08280808 A | 10/1996 |
| JP | H 08322934 A | 12/1996 |
| JP | H 0928805 A | 2/1997 |
| JP | 9-154948 A | 6/1997 |
| JP | H 09248342 A | 9/1997 |
| JP | H 1028735 A | 2/1998 |
| JP | H 11197245 A | 7/1999 |
| JP | H 11221280 A | 8/1999 |
| JP | H 11226127 A | 8/1999 |
| JP | 2001-095918 A | 4/2001 |
| JP | 2005-168513 A | 6/2005 |
| JP | 2005-270372 A | 10/2005 |
| JP | 2006122189 | 5/2006 |
| WO | WO 90/07351 A1 | 7/1990 |
| WO | WO 96/29109 A1 | 9/1996 |
| WO | WO 97/04826 A1 | 2/1997 |
| WO | WO 97/42992 A1 | 11/1997 |
| WO | WO 02/00282 A1 | 1/2002 |
| WO | WO 03/000310 A2 | 1/2003 |
| WO | WO 2005/000477 A1 | 1/2005 |
| WO | WO 2005/023335 A2 | 3/2005 |
| WO | WO 2007/102089 A2 | 9/2007 |
| WO | WO 2008/026730 A1 | 3/2008 |

OTHER PUBLICATIONS

European search report dated Jul. 31, 2015 for EP Application No. 12742112.

* cited by examiner

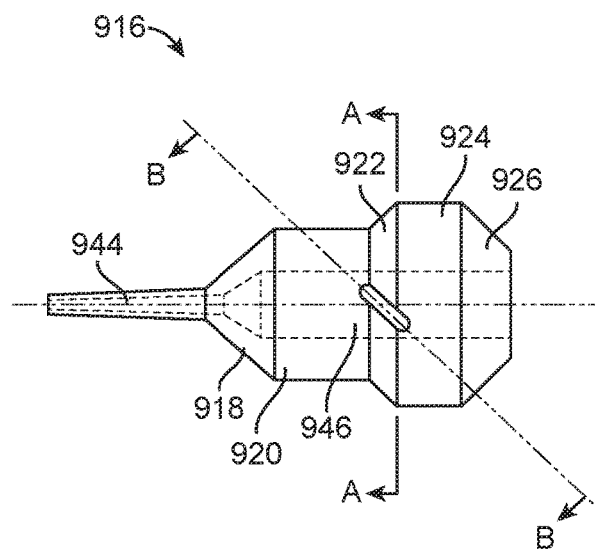
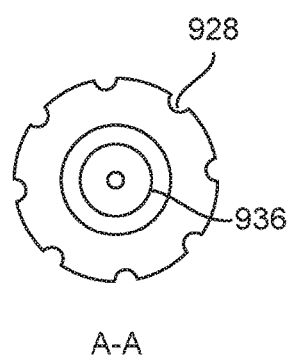
FIG. 10A    FIG. 10B
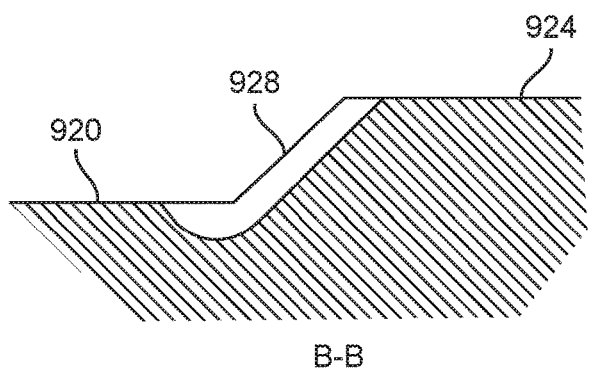
FIG. 10C
  
FIG. 10D    FIG. 10E    FIG. 10F

INTRANASAL DELIVERY DEVICES

TECHNICAL FIELD

Priority

Incorporation by Reference

This application claims the benefit of U.S. Provisional Application No. 61/437,994, filed Jan. 31, 2011, which is hereby incorporated by reference. All publications and patent applications mentioned in this specification are herein incorporated by reference to the same extent as if each individual publication or patent application was specifically and individually indicated to be incorporated by reference.

BACKGROUND ART

Background of the Invention

Devices and methods for delivering a powdered therapeutic formulation into a nostril and/or nasal cavity of a subject (e.g., a patient) are generally known and can include devices and methods described in U.S. Pat. Nos. 7,278,982 and 7,438,700, herein incorporated by reference in their entireties. Available devices and methods for delivering a powdered therapeutic formulation can have one or more deficiencies. For example, reusable intranasal delivery devices can require regular cleaning and maintenance to prevent contamination and assure good hygiene and proper operation. Additionally, intranasal delivery devices can fail to deliver a consistent or reproducible dose or can fail to deliver substantially all of a dose. The size and weight of an intranasal delivery device can impose a burden when the user carries the device about or can make the intranasal delivery device awkward to hold or use. Methods and devices described herein can address these and other issues, thereby providing a simple and more convenient way for a patient or caregiver to intranasally administer a powdered therapeutic formulation.

CITATION LIST

Patent Literature
[PTL 1]U.S. Pat. No. 7,278,982
[PTL 2]U.S. Pat. No. 7,438,700

SUMMARY OF INVENTION

In one aspect, a device is provided comprising: a) a nozzle having an upstream end and a downstream end adapted to allow positioning of at least a portion of said nozzle into a nostril of a subject; b) a reservoir comprising a single dose of a powdered therapeutic formulation, the reservoir having an upstream end and a downstream end, and disposed within said nozzle; c) a valve having an upstream end and a downstream end, wherein the valve is adapted to occupy a first position and a second position in the device, and wherein the valve is adapted to cause diffusion of the powdered therapeutic formulation when the device is activated; and d) an air source operably linked to the upstream end of a valve, wherein the device is a single-use device. In one embodiment, the valve is adapted to create a spinning airflow in the reservoir when the air source is activated. In another embodiment, the valve is adapted to permit the entire wall of the reservoir to be covered by airflow when the air source is activated. In another embodiment, the valve is at least partially located in the nozzle. In another embodiment, the powdered therapeutic formulation is located along the internal wall of the nozzle and between the valve and internal wall of the nozzle. In another embodiment, the valve is adapted to minimize the powdered therapeutic formulation remaining between the valve and the internal wall of the nozzle when the air source is activated. In another embodiment, the device is adapted to deliver between 80% and 99% of the single dose of powdered therapeutic formulation into the nostril of the subject. In another embodiment, the device is adapted to deliver between 80% and 99% of the single dose of powdered therapeutic formulation into the nostril of the subject after a single activation of the air source. In another embodiment, the air source comprises a flow outlet. In another embodiment, the valve is adapted to prevent movement of the powdered therapeutic formulation through the flow outlet when the device is not activated. In another embodiment, the valve is adapted to prevent movement of the powdered therapeutic formulation through the flow outlet when the device is activated. In another embodiment, the valve covers the flow outlet when the device is not activated. In another embodiment, the valve does not cover the flow outlet when the device is activated. In another embodiment, the valve comprises a top section connected to a first cylindrical section, and the first cylindrical section is connected to a first shelf, and the first shelf is connected to a second cylindrical section.

In another embodiment, wherein the top section comprises a conical shape. In another embodiment, a surface of the first shelf comprises at least one slit. In another embodiment, the first shelf comprises at least one slit. In another embodiment, the first shelf comprises about 1 to 50 slits. In another embodiment, the first shelf comprises about 1 to 20 slits. In another embodiment, the first shelf comprises about 1 to 10 slits. In another embodiment, the at least one slit lies at a 45 degree angle relative to an edge of the first shelf. In another embodiment, the at least one slit is adapted to permit air flow from the air source to the nozzle when the air source is engaged. In another embodiment, the nozzle comprises a nozzle pipe. In another embodiment, the valve is partially located within the nozzle pipe. In another embodiment, the top section and first cylindrical section of the valve are located within the nozzle pipe. In another embodiment, the second cylindrical section of the valve is not located within the nozzle pipe.

In another embodiment, the first shelf contacts the nozzle pipe in the air source is activated. In another embodiment, the air source is adapted to deliver between 2 and 7 mL of air. In another embodiment, the device is adapted to deliver between 1 and 50 mg of powdered therapeutic agent. In another embodiment, the device is less than 50 cm$^3$ in volume. In another embodiment, the device has a mass of less than 20 grams. In another embodiment, the air source is adapted to be activated by a user to force air from the air source through the flow outlet, along the surface of the at least one slit in the first shelf, into the reservoir, and out the downstream end of a nozzle. In another embodiment, the device is adapted to provide laminar airflow within at least a portion of a reservoir while a device is in use. In another embodiment, the air source comprises a pump. In another embodiment, the device is adapted to deliver a powdered therapeutic composition into the nostril of the subject by application of between about 5 and about 30 kilopascals of compressive force to a pump. In another embodiment, the pump further comprises a deformable volume adapted to be activated by a user. In another embodiment, the pump comprises a manual air pump. In another embodiment, the manual air pump is adapted to be activated by a user by squeezing the pump between a thumb and a forefinger, middle finger, ring finger, little finger or combination thereof. In another embodiment, the reservoir comprises an inner diameter of less than 10 mm. In another embodiment, the nozzle further comprises a length perpendicular to an upstream to downstream axis of between 5 mm and 20 mm. In another embodiment, the nozzle further comprises a length parallel to an upstream to downstream axis of between 5 mm and 40 mm.

In another embodiment, the air source further comprises a flow inlet, wherein said flow inlet is less than 10% of the size of a flow outlet. In another embodiment, said flow inlet is between 0.1 and 2 mm in diameter. In another embodiment, the nozzle further comprises an airtight cap positioned on the upstream end of a nozzle and adapted to prevent outside air from contacting a powdered therapeutic formulation. In another embodiment, the nozzle further comprises a removable or breakable cover positioned at the downstream end of a nozzle, and adapted to prevent a flow of air through a nozzle. In another embodiment, the downstream end of the nozzle further comprises a nozzle hole.

In another embodiment, the valve is adapted to provide laminar airflow along at least a portion of the reservoir. In another embodiment, the valve is adapted to move from a first position to a second position, wherein in the first position the upstream surface is in communication with a flow outlet and thereby the flow of air into a reservoir is blocked, and in the second position the flow of air into the reservoir is allowed. In another embodiment, sufficient flow of air is generated by a compression force of at least 20 kilopascals applied to the air source. In another embodiment, the nozzle is comprised of a substantially clear or translucent material. In another embodiment, the nozzle further comprises a thread adaptable to secure the nozzle to the air source.

In another aspect, a method of using a device to deliver a powdered therapeutic formulation is provided, wherein said method comprises positioning a nozzle of a device into a nostril of a subject and activating an air source, and wherein said device is a single-use device that comprises: a) a nozzle having an upstream end and a downstream end, said nozzle adapted to allow position of at least a portion of said nozzle into a nostril of a subject; b) a reservoir comprising a dose of a powdered therapeutic formulation and having an upstream end and a downstream end, operably linked to and disposed within said nozzle; c) a valve having an upstream end and a downstream end, wherein the valve is adapted to occupy a first position and a second position in the device, and wherein the valve is adapted to cause diffusion of the powdered therapeutic formulation when the device is activated; and d) an air source operably linked to the upstream end of a valve, wherein the device is a single-use device. In one embodiment, the nozzle and the reservoir of the device comprise clear or translucent material and wherein the method further comprises visually inspecting the amount of powdered therapeutic formulation remaining in a reservoir and repeating the method until a sufficient dose is delivered. In another embodiment, the method further comprises moving the valve from a first position to a second position when the device is activated. In another embodiment, the method further comprises activating the air source to produce laminar flow along at least a portion of a reservoir. In another embodiment, the method further comprises delivering between 1 mg and 50 mg of a powdered therapeutic formulation to the nostril of the subject. In another embodiment, the method further comprises delivering between 80% and 99% of the single dose of powdered therapeutic formulation to the nostril of the subject. In another embodiment, the method further comprises compressing the manual air pump with between 5 and 30 kilopascals of force. In another embodiment, the method further comprises removing a cover from the nozzle before the nozzle is positioned in the nostril of the subject.

In another aspect, a method of manufacturing a device for delivering a powdered therapeutic formulation to a subject, wherein said method comprises providing a powdered therapeutic formulation to a reservoir and subsequently coupling a nozzle to an air source, wherein said device comprises: a) a nozzle having an upstream end and a downstream end, said nozzle adapted to allow positioning of at least a portion of said nozzle into a nostril of a subject; b) a reservoir comprising a dose of a powdered therapeutic formulation and having an upstream end and a downstream end, operably linked to and disposed within said nozzle; c) a valve having an upstream end and a downstream end, wherein the valve is adapted to occupy a first position and a second position in the device, and wherein the valve is adapted to cause diffusion of the powdered therapeutic formulation when the device is activated; and d) an air source operably linked to the upstream end of a valve.

In one embodiment, the device does not comprise a flow inlet when the removable cover positioned at the downstream end of the nozzle is not removed. In one embodiment, the reservoir for a powdered therapeutic formulation is a closed system when the removable or breakable cover is not removed, thereby increasing the stability of a powdered therapeutic formulation within the reservoir. In one embodiment, the device comprises a flow inlet when the removable cover positioned at the downstream end of the nozzle is removed. In one embodiment, the downstream end of the nozzle further comprises a nozzle hole and the nozzle hole comprises the flow inlet.

In some embodiments, the valve comprises an inner inlet section and the inner inlet section is connected to a first cylindrical section, and the first cylindrical section is connected to a first shelf, and the first shelf is connected to a second cylindrical section. In one embodiment the valve further comprises an inner inlet section and the inner inlet section is connected to the top section. In some embodiments, the valve comprises a valve cavity. In one embodiment, the valve cavity comprises a hollow chamber within the valve, an opening at the upstream end of the valve cavity, and an opening at the downstream end of the valve cavity. In one embodiment, the valve cavity spans the entire length of the valve. In one embodiment, the valve cavity and the opening at the upstream end of the valve cavity is connected to the reservoir and the opening at the downstream end of the valve cavity is connected to the air source.

In some embodiments, all air within the pump enters the reservoir when the pump is activated, thereby increasing delivery of the powdered therapeutic formulation.

BRIEF DESCRIPTION OF DRAWINGS

The novel features are set forth with particularity in the appended claims. A better understanding of the features and advantages will be obtained by reference to the following detailed description that sets forth illustrative embodiments, in which the principles of devices, methods, and compositions are utilized, and the accompanying drawings of which:

FIG. 1 illustrates a cross-sectional view of an intranasal delivery device described herein. The breakable cover (134) can be a removable cover.

Figure 1:
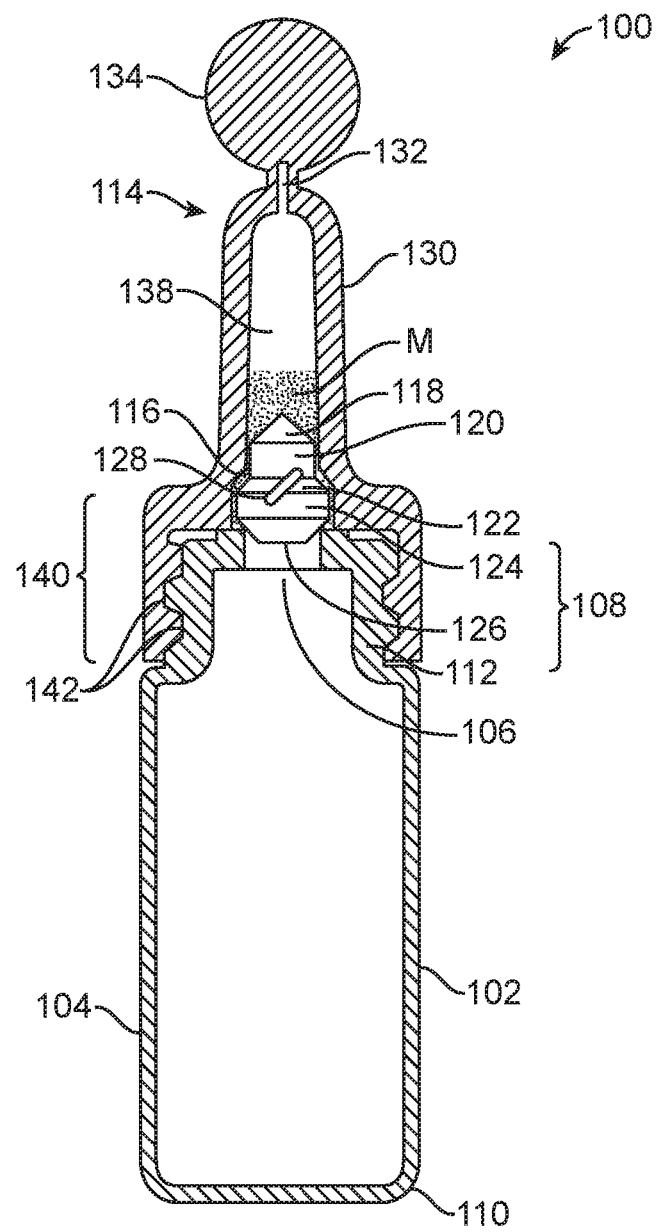
Figure 6:
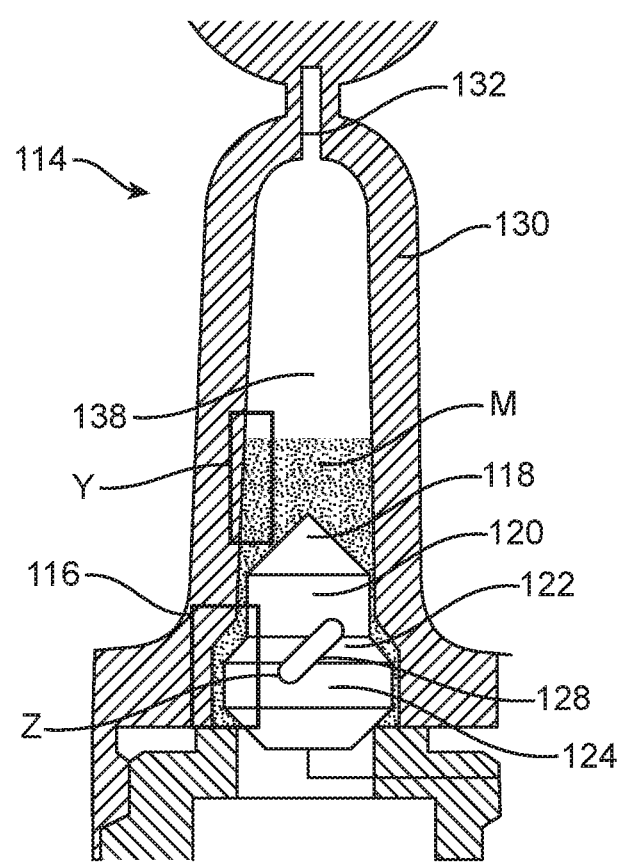

FIG. 6 illustrates a magnified view of an embodiment of a device illustrated in FIG. 1. One box in the figure highlights powdered therapeutic formulation along an internal wall of the nozzle (Y). Another box in the figure highlights powdered therapeutic formulation between an internal wall of the nozzle and the one way valve (Z).

Figure 7A:
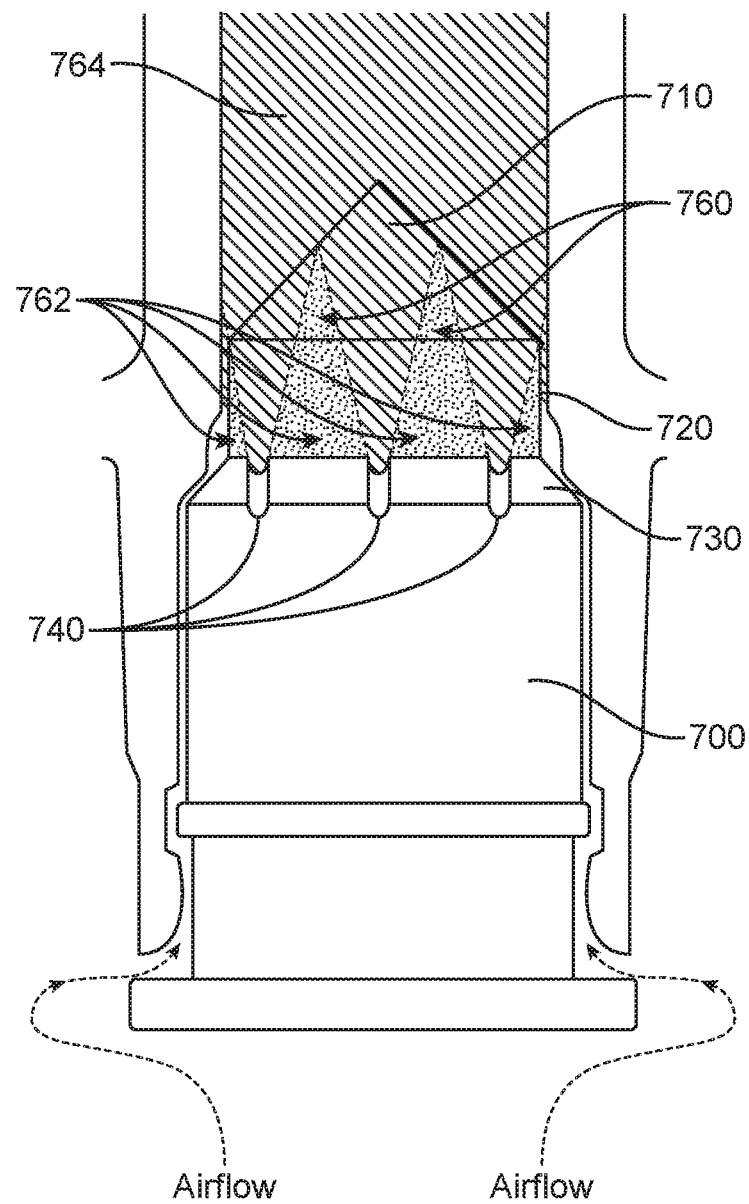
Figure 7B:
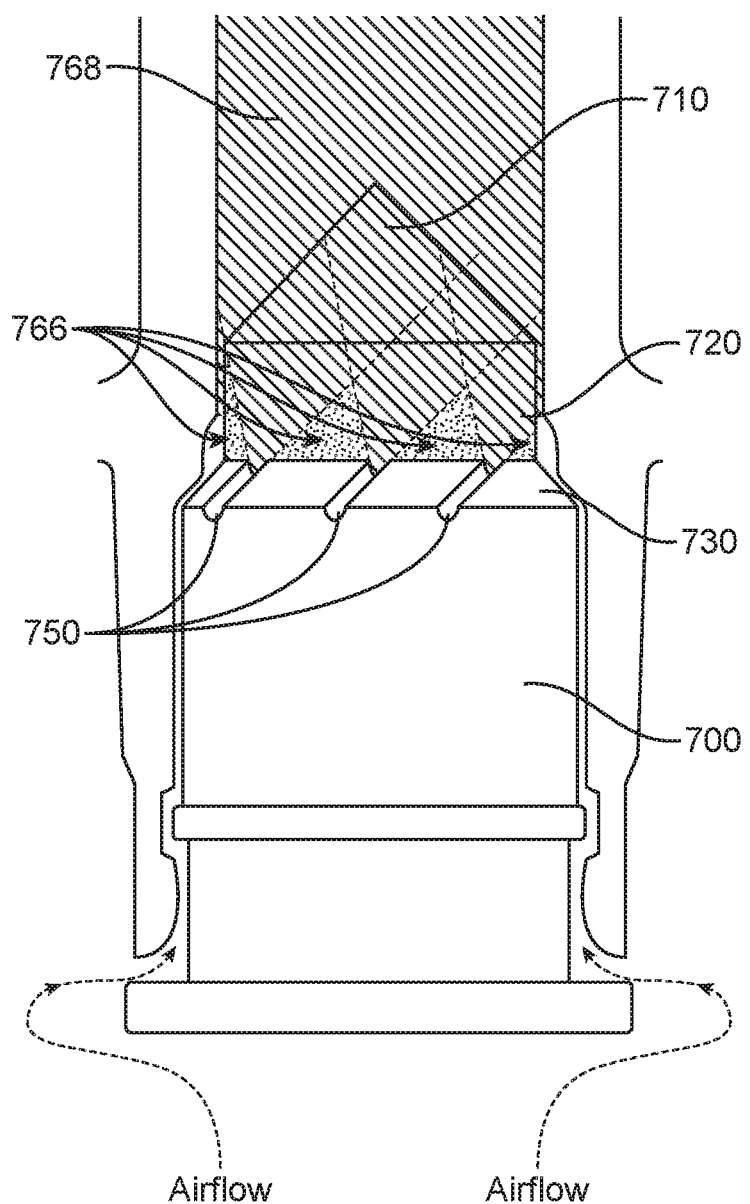

FIGS. 7A and 7B illustrate differences in access of air flow along the internal wall of the nozzle and along the surface of the one way valve (700) when the slits on the first shelf (730) of the one way valve (700) are non-diagonal (FIG. 7A, 740) and when the slits are diagonal (FIG. 7B, 750).

Figure 8A:
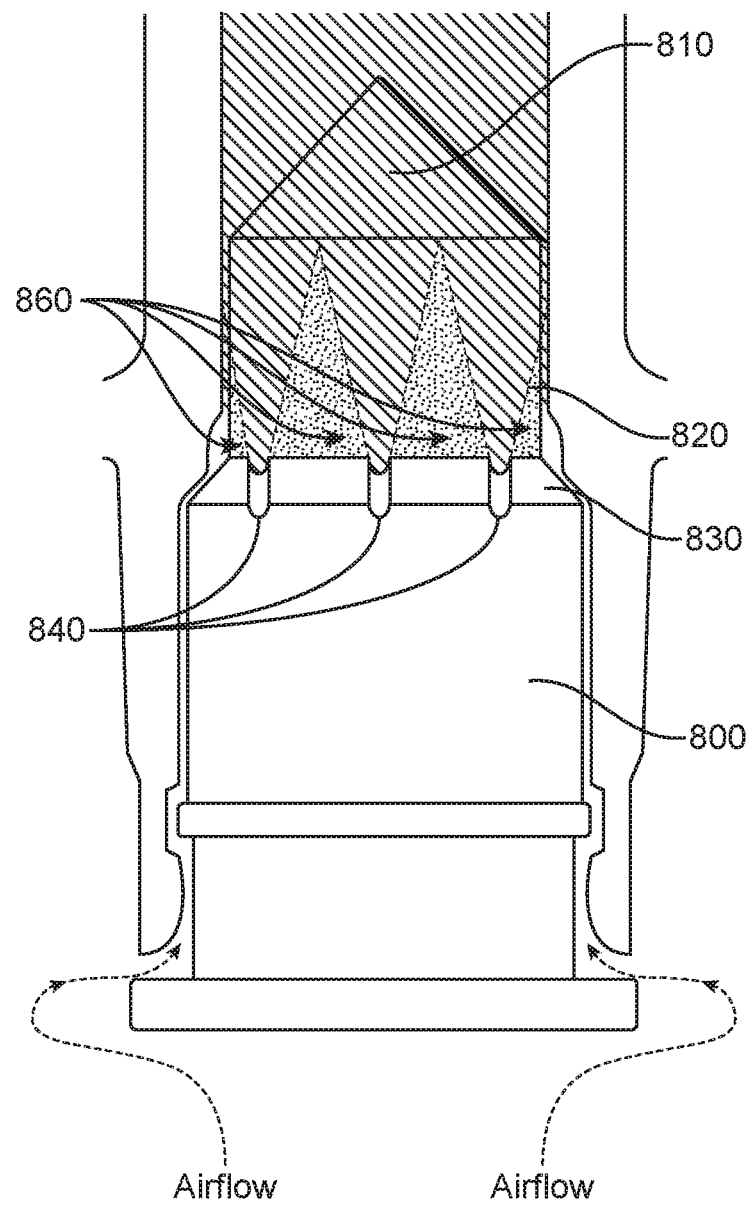
Figure 8B:
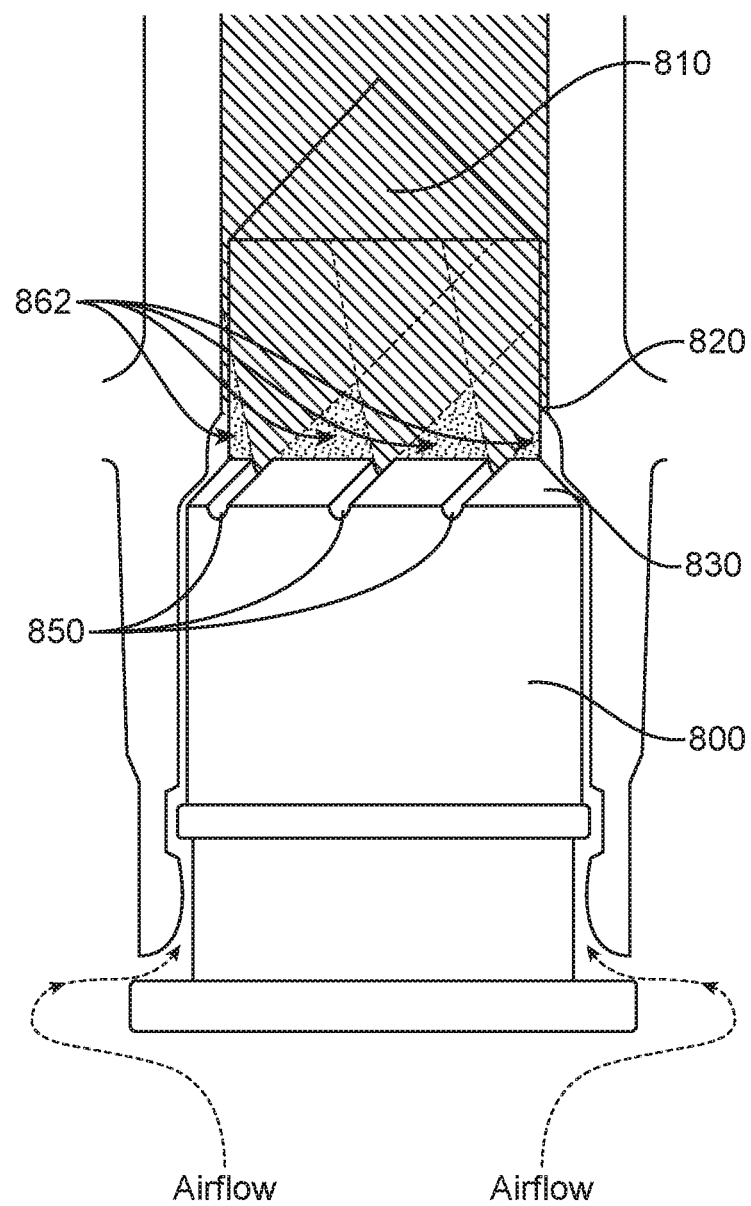

FIGS. 8A and 8B illustrate differences in access of air flow along the one way valve (800) when the slits in the first shelf (830) are non-diagonal (FIG. 8A, 840) and when the slits are diagonal (FIG. 8B, 850).

Figure 9:
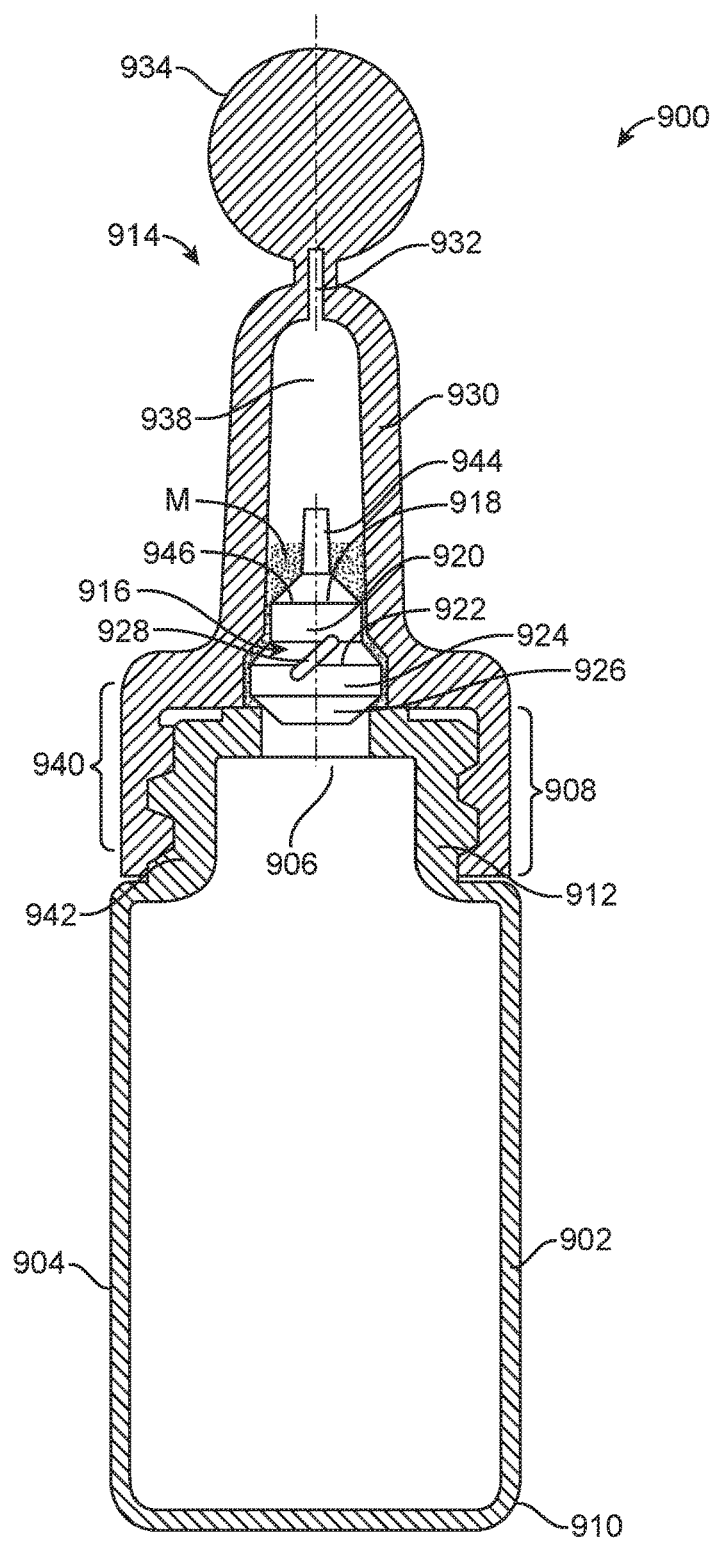

FIG. 9 illustrates a cross-sectional view of an intranasal delivery device described herein.

FIGS. 10A-10F illustrate different views of a one way valve for use in intranasal delivery devices.

Figures 11A, 11B:
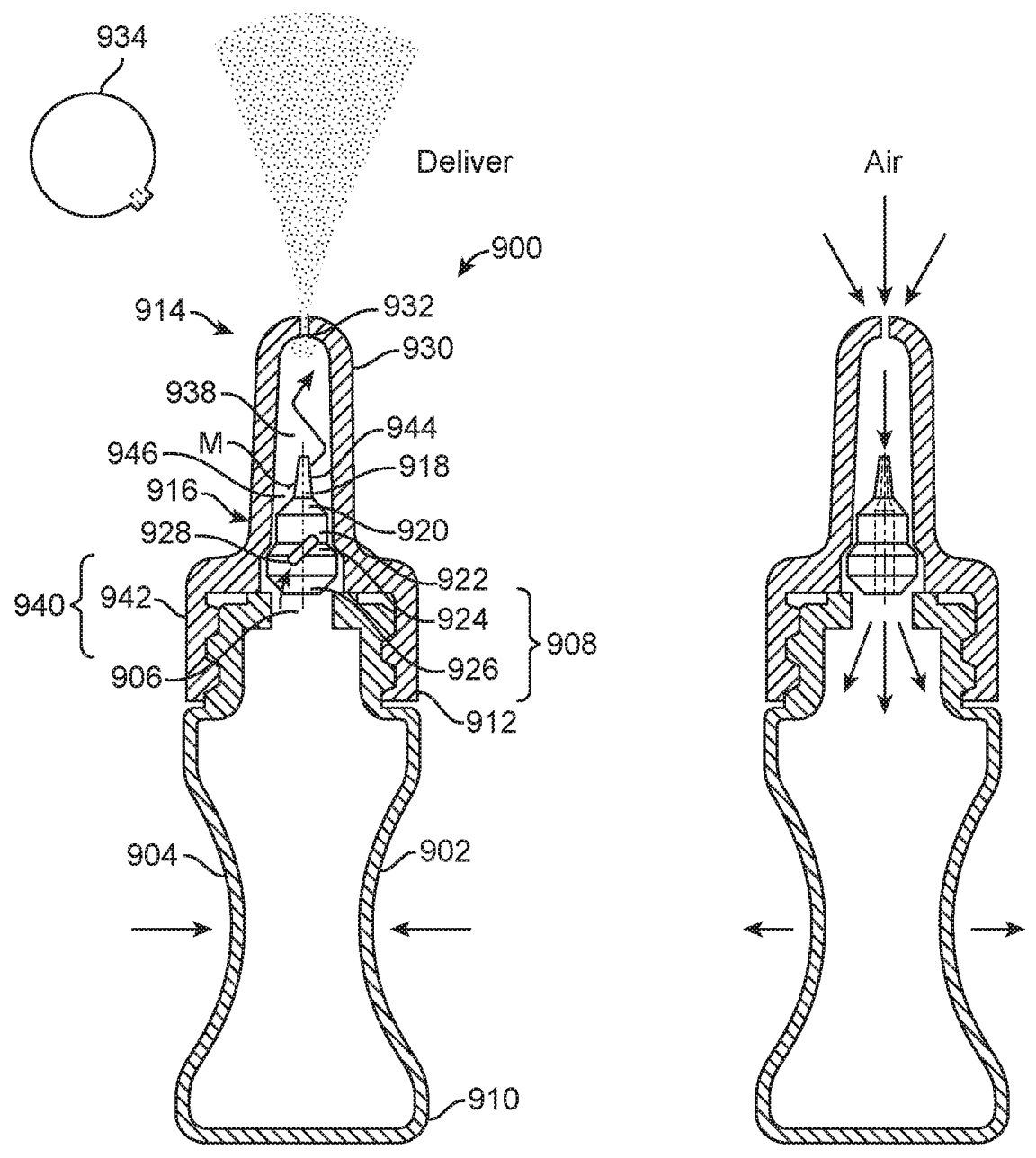

FIGS. 11A-11B illustrate a method of using the intranasal delivery device illustrated in FIG. 9.

DESCRIPTION OF EMBODIMENTS

Detailed Description of the Invention

The present application describes intranasal delivery devices. An intranasal delivery device can be used for administering a powdered therapeutic formulation to a person in need of treatment. Delivery of a powdered therapeutic formulation can be performed by a medical professional and/or by the person in need of treatment (e.g., a patient). As described herein, devices can be pre-loaded with a dry powdered therapeutic formulation. An intranasal delivery device can be a single-use device. Devices described herein can have few parts. For example, devices described herein can comprise three parts, e.g., an air source, a nozzle, and a one-way valve. A powdered therapeutic formulation can be introduced into the nozzle of a device, which can serve as a reservoir. The nozzle can be coupled with an air source. A novel feature of single-use intranasal delivery devices disclosed herein can be the presence of a one way valve which can allow for a high rate of clearance of a powdered therapeutic formulation from the devices. Devices described herein can provide for complete delivery of a powdered therapeutic formulation with minimal powdered therapeutic formulation remaining in the device after activation of the device. The one way valve can occupy a first position in a device when the device is not activated and a second position in the device when the device is activated. A one way valve can be adapted to regulate airflow from an air source to a nozzle when the device is activated. A one way valve can be adapted to prevent movement of a powdered therapeutic formulation from a reservoir in the device upstream to an air source in the device. The one way valve can comprise slits (canals or grooves) that can be used to generate a vortex in a reservoir to enable efficient delivery of a powdered therapeutic formulation. The slits in the one way valve can be positioned to permit laminar air flow in the reservoir. The slits in the one way valve can be positioned to create spinning air flow in the reservoir when the air source is activated.

I. Devices

Overview

Provided herein are intranasal delivery devices that can comprise a nozzle, a one way valve, and an air or gas source. The nozzle can be in communication with the air or gas source, and the one way valve can be positioned within the nozzle. In some embodiments, the nozzle is not in fluid communication with the air or gas source when the one way valve is in a first position and the nozzle is in fluid communication with the air or gas source when the one way valve is in a second position.

Devices described herein can be more fully understood by reference to the figures provided herein. FIG. 1 illustrates a cross-sectional view of a single-use intranasal delivery device. The intranasal delivery device (100) can comprise air source, which can be a flexible vial (102). The flexible vial can function as a manual air pump (104). The flexible vial can comprise a flow inlet (not shown) and a flow outlet (106). Optionally, the flexible vial does not need to comprise a flow inlet. The flexible vial can comprise a throat (108) at the top of the flexible vial with a narrower diameter than the bottom of the flexible vial (110). The throat (108) can comprise an external thread (112) for attachment of a nozzle (114).

A one way valve (116) can sit on a surface in the throat (108) of the flexible vial (102) and block the flow outlet (106) when the device is not activated (e.g., when the manual air pump is not compressed). Resting of the one way valve (116) on a surface in the throat (108) can prevent a powdered therapeutic composition (M) from entering the flexible vial (102) when the device is not activated.

A one way valve (116) can comprise a top section (118), a first cylindrical section (120), a first shelf (122), a second cylindrical section (124), and a second shelf (126). One or more slits (128) can be in the surface of the first shelf. One or more slits (128) can permit flow of air or gas from the flexible vial (102) to the nozzle (114) when the manual air pump (104) is compressed (see e.g., FIG. 3). Embodiments of the one way valve (116) are depicted in FIGS. 2A-2F.

An intranasal device (100) can further comprise a nozzle (114) that can comprise a nozzle pipe (130) which can be inserted or partially inserted into the nasal cavity or a nostril of a subject. The nozzle (114) can further comprise a nozzle hole (132), a removable or breakable cover (134), and a reservoir for a powdered therapeutic formulation (138). The reservoir for the powdered therapeutic formulation can comprise a powdered therapeutic formulation (M). The nozzle (114) can comprise a base (140) that can comprise an internal thread (142) for attachment to the throat (108) of the flexible vial (102). The internal thread of the nozzle base can mate with an external tread of the vial throat.

Figure 2A:
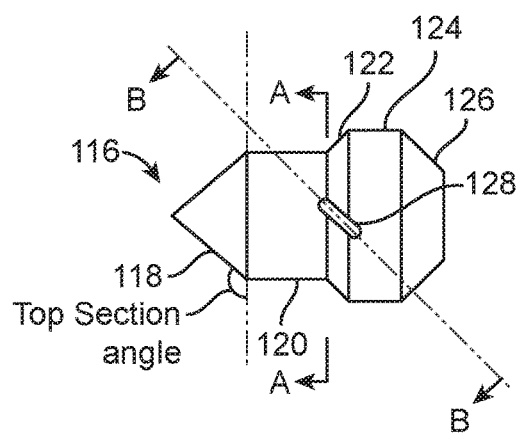
FIGS. 2A-2F illustrate different views of a one way valve for use in intranasal delivery devices.

FIGS. 2A-2F illustrate different views of embodiments of a one way valve (116) that correspond to the one way valve (116) illustrated in FIG. 1. FIG. 2A illustrates a side view of a one way valve (116) with the top of the one way valve pointing to the left. In this embodiment, the one way valve comprises a top section (118) and a first cylindrical section (120) extending from the base of the top section (118). At the base of the first cylindrical section is a first shelf (122) that extends outward and downward from the base of the first cylindrical section (120). Illustrated here is a single slit (128) on the top of the first shelf (122), and the slit lies at a non 90 degree angle relative to either edge of the shelf. The first shelf can have multiple slits. The bottom of the first shelf connects to the top of a second cylindrical section (124). The bottom of the second cylindrical section connects to a second shelf (126) that can extend inward and downward relative to the bottom of the second cylindrical section (124). In some embodiments, the one way valve can be integrally formed as a single piece. For example, a top section, first cylindrical section, first shelf, second cylindrical section, and second shelf can be integrally formed as a single piece. Alternatively, one or more parts of the one way valve can be formed separately.

Figure 2B:
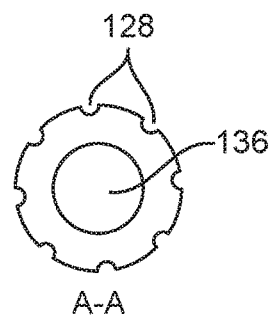

FIG. 2B illustrates a cross-sectional view of the one way valve along a plane AA of FIG. 2A as viewed from the right of the one way valve (116) depicted in FIG. 2A. The cross-sectional view illustrates multiple indentations (128) around the perimeter of the first shelf of the one way valve that correspond to slits (128). The circle in the middle (136) illustrates that the one way valve (116) can be hollow. In other embodiments, the one way valve can be solid. In other embodiments, the one way valve is not hollow.

Figure 2C:
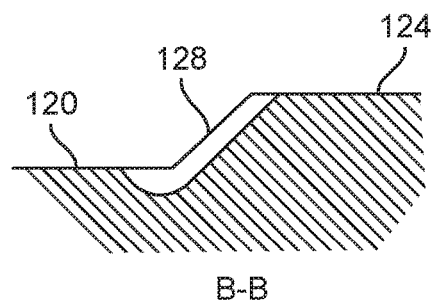

FIG. 2C illustrates a cross-sectional view along the plane of BB of FIG. 2A as viewed from the bottom and left of the one way valve illustrated in FIG. 2A. A slit is illustrated (128).

Figure 2D:
Figure 2E:
Figure 2F:

FIGS. 2D-2F illustrate cross-sectional views of a portion of a one way valve along a plane AA as in FIG. 2A as viewed from the right of the one way valve depicted in FIG. 2A. Different geometries for slits that can be formed in the top shelf of the one way valve of FIG. 2A are illustrated. The geometry of the slit in this view can be formed by a curved surface (FIG. 2D), by two surfaces (FIG. 2E), or by 3 surfaces (FIG. 2F). The cross-sectional geometry of the slit can be curved, angled, or any combination thereof.

Figure 3:
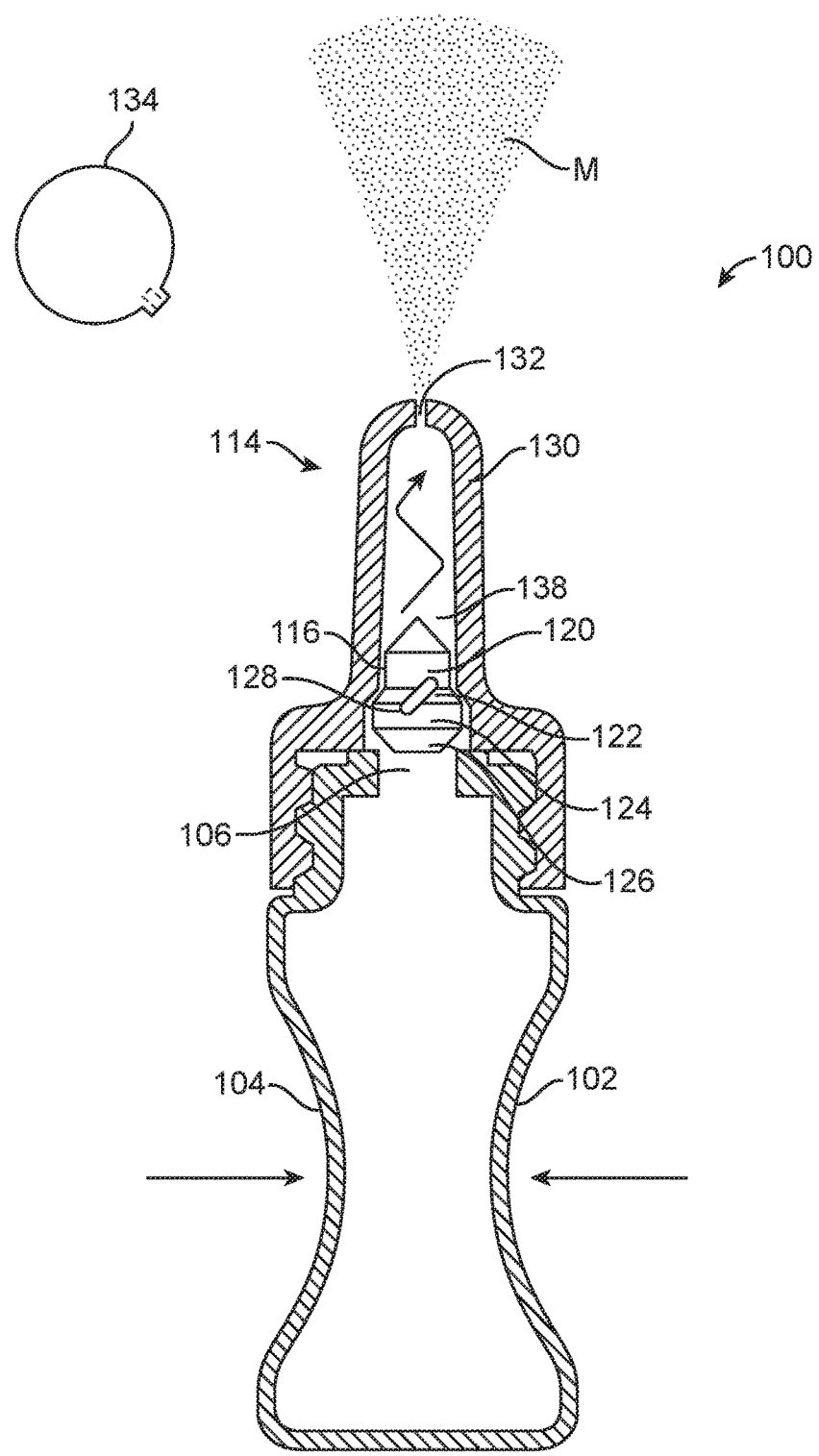
FIG. 3 illustrates a method of using the intranasal delivery device illustrated in FIG. 1. The breakable cover (134) can be a removable cover.
Figure 4:
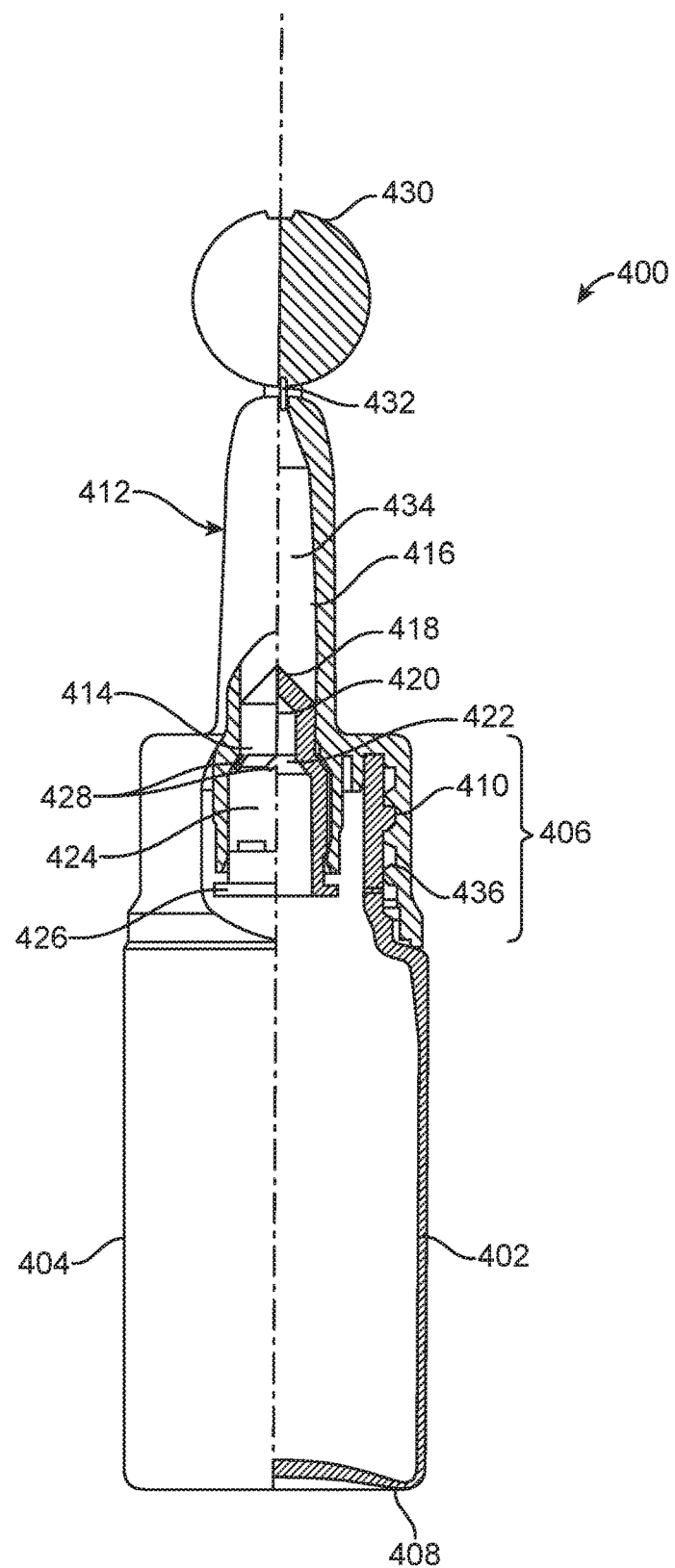
FIG. 4 illustrates an external view (left) and a cross-sectional view (right) of an intranasal delivery device and one way valve described herein. The breakable cover (430) can be a removable cover.

FIG. 3 illustrates an activated configuration of the intranasal delivery device illustrated in FIG. 1 and the flow path of air or gas from the manual air pump (104) to the nozzle (114). The removable or breakable cover (134) is removed from the intranasal delivery device (100). A one way valve (116) can be resting on the surface of a vial throat (108). A user compresses the flexible vial (102) (compression is illustrated by the arrows and the deformed flexible vial relative to the vial in FIG. 1) that serves as a manual air pump (104). Air flows out the flow outlet (106) of the flexible vial (102). The air flow causes the one way valve (116) to rise in the nozzle (114). When the one way valve (116) rises in the nozzle it may no longer be resting on the vial throat (108). The non-slit portions of the first shelf (122) of the one way valve contact the nozzle pipe (130) to prevent a powdered therapeutic formulation from moving upstream into the flexible vial (102). Air travels around the second shelf (126) of the one way valve (116) and the second cylindrical section (124) of the one way valve (116) and flows through the slit (128) in the first shelf (122) of the one way valve (116). The air then flows between the first cylindrical section (120) and the nozzle pipe (130) into the reservoir (138) and forces the powdered therapeutic formulation (M) up the nozzle pipe (130) and out the nozzle hole (132).

FIG. 4 illustrates another embodiment of an intranasal delivery device. The left half of the illustration is a partial external view of an intranasal delivery device with part of the external portion of the nozzle cut-away to permit an external view of an embodiment of a one way valve (414). The right half of the illustration is a cross-sectional view of the intranasal delivery device including a cross-sectional view of a one way valve (414). An intranasal delivery device (400) can comprise a flexible vial (402) that can serve as a manual air pump (404). The flexible vial can comprise a throat (406) at the top of the flexible vial with a narrower diameter than the bottom of the flexible vial (408). The throat (406) can comprise an external thread (410) for attachment of a nozzle (412). The internal thread of a nozzle base can mate with an external tread of the vial throat (410).

A one way valve (414) can be partial located in a nozzle pipe (416). A one way valve can comprise a top section (418), a first cylindrical section (420), a first shelf (422), a second cylindrical section (424), and a base (426). The base can extend outward from the second cylindrical section. The base can have a flat bottom. Alternatively, the base can have a curved or slanted bottom. In some embodiments, the base can be solid. Alternatively, the base can have one or more opening or hole that can lead to a hollow section of the one way valve. One or more slits (428) can be in the surface of the first shelf (422). One or more slits (428) can permit flow of air or gas from the flexible vial (402) to the nozzle (412) when the manual air pump is compressed.

An intranasal delivery device (400) can further comprise a nozzle (412) which can comprise a nozzle pipe (416) which can be inserted or partially inserted into the nasal cavity or a nostril of a subject. The nozzle (412) can further comprise a removable or breakable cover (430), a nozzle hole (432), and a reservoir for a powdered therapeutic formulation (434). The nozzle (412) can further comprise a thread (436) for attachment to the flexible vial (402).

FIG. 5 is a magnified view of FIG. 4 that illustrates an external view of a one way valve (414) on the left and a cross-sectional view of the one way valve (414) on the right. A portion of the throat (406) of a flexible vial is shown and a thread (408) of the throat is shown. A portion of the nozzle pipe (416) and nozzle base (436) are shown.

An air inlet (438) is shown in the throat (406) of the flexible vial. Air can enter the vial through a space between the nozzle base and throat of the flexible vial (440) that is connect to the air inlet (438). A portion of a nozzle base (436) is shown attached to the flexible vial throat (406), and portion of a thread of the nozzle (442) and a portion of the nozzle pipe (416) and reservoir (434) for a powdered therapeutic formulation are shown.

The one way valve (414) can comprise a top section (418), a first cylindrical section (420), a first shelf (422), a second cylindrical section (424), and a base (426). A one way valve (414) can also comprise a ridge (444) that can sit on a lower bulge (446) of the nozzle pipe (416) to prevent a powdered therapeutic formulation from moving upstream into the flexible vial. The one way valve can be hollow.

In the embodiment illustrated in FIGS. 4 and 5, when the manual air pump is activated, the one way valve (414) moves upward and the ridge (444) of the one way valve moves off the lower bulge (446) of the nozzle pipe (416). The first shelf (422) of the one way valve (414) contacts the upper ridge (448) of the nozzle pipe, which stops the upward movement of the one way valve (414). Air or gas flows between the second cylindrical section (424) and the nozzle pipe (416), through the slits (428), and between the first cylindrical section (420) and the nozzle pipe (416), forcing a powdered therapeutic formulation in the powdered therapeutic formulation reservoir (434) up the nozzle.

Device Height

The devices disclosed herein can be of any convenient dimensions for application of a powdered therapeutic formulation contained therein. For example, a device can be between about 3-15 cm, 4-15 cm, 5-15 cm, 6-15 cm, 7-15 cm, 8-15 cm, 3-10 cm, 3-9 cm, or 3-8 cm in height. A device can be about 3 cm, about 4 cm, about 5 cm, about 6 cm, about 7 cm, about 8 cm, about 9 cm, about 10 cm, about 11 cm, about 12 cm, about 13 cm, about 14 cm, or about 15 cm in height. A device can be more than about 3 cm, about 4 cm, about 5 cm, about 6 cm, about 7 cm, about 8 cm, about 9 cm, about 10 cm, about 11 cm, about 12 cm, about 13 cm, about 14 cm, or about 15 cm in height. A device can be less than about 3 cm, about 4 cm, about 5 cm, about 6 cm, about 7 cm, about 8 cm, about 9 cm, about 10 cm, about 11 cm, about 12 cm, about 13 cm, about 14 cm, or about 15 cm in height. Dimensions for the device can be chosen based on the amount of powdered therapeutic composition to be delivered, ease of use, ease of portability, or manufacturing convenience.

Device Volume

As described herein, a device can be configured to be a small size such that it can easily be stored or transported. A device can be between about 1 and 100 $cm^3$ in volume, between about 5 and 90 $cm^3$ in volume, between about 10 and 80 $cm^3$ in volume, between about 25 and 80 $cm^3$ in volume, between about 50 and 100 $cm^3$ in volume, between about 1 and 50 $cm^3$ in volume, between about 5 and 75 $cm^3$ in volume, between about 1 and 25 $cm^3$ in volume, between about 5 and 50 $cm^3$ in volume, between about 10 and 50 $cm^3$ in volume, or between about 25 and 50 $cm^3$ in volume. A device can be at least about 1, 2, 5, 10, 25, 30, 40, 50, 75, or 100 $cm^3$ in volume. A device can be less than about 250, 200, 175, 150, 125, 100, 75, 70, 65, 60, 55, 50, 40, 30, 25, 10, 5, 2, or 1 $cm^3$ in volume.

Device Width

At its widest point, the device can be between about 0.5-5 cm in width. The device at its widest point can be about 0.5, 1, 1.5, 2, 2.5, 3, 3.5, 4, 4.5, or 5 cm in width. The device at its widest point can be more than about 0.5, 1, 1.5, 2, 2.5, 3, 3.5, 4, 4.5, or 5 cm in width. The device at its widest point can be less than about 0.5, 1, 1.5, 2, 2.5, 3, 3.5, 4, 4.5, or 5 cm in width.

Device Mass

A device can be configured to be lightweight. For example, a device can have a total mass of between about 1 and about 50 grams, between about 5 and about 40 grams, between about 10 and about 35 grams, between about 10 and about 30 grams, between about 10 and about 25 grams, between about 1 and about 10 grams, between about 1 about 5 grams, or between about 10 and about 20 grams. A device can have a total mass of less than about 100 grams, 90 grams, 80 grams, 75 grams, 70 grams, 65 grams, 60 grams, 55 grams, 50 grams, 45 grams, 40 grams, 35 grams, 30 grams, 25 grams, 20 grams, 10 grams, 9 grams, 8 grams, 7 grams, 6 gram, 5 grams, 4 grams, 3 grams, 2 grams, 1 gram, 0.5 gram, or less. A device can have a total mass of more than about 0.5 gram, 1 gram, 2 grams, 3 grams, 4 grams, 5 grams, 6 grams, 7 grams, 8 grams, 9 grams, 10 grams, 11 grams, 12, grams, 13 grams, 14 grams, 15 grams, 16 grams, 17 grams, 18 grams, 19 grams, 20 grams, 25 grams, 30 grams, 35 grams, 40 grams, 45 grams, 50 grams, 55 grams, 60 grams, 65 grams, 70 grams, 75 grams, 80 grams, 85 grams, 90 grams, 95 grams, or 100 grams. A device can a have a total mass of about 1 gram, 2 grams, 3 grams, 4 grams, 5 grams, 6 grams, 7 grams, 8 grams, 9 grams, 10 grams, 11 grams, 12, grams, 13 grams, 14 grams, 15 grams, 16 grams, 17 grams, 18 grams, 19 grams, 20 grams, 25 grams, 30 grams, 35 grams, 40 grams, 45 grams, 50 grams, 55 grams, 60 grams, 65 grams, 70 grams, 75 grams, 80 grams, 85 grams, 90 grams, 95 grams, or 100 grams. Total mass can be the mass of a device without a powdered therapeutic formulation or the mass of a device with a powdered therapeutic formulation.

Device Delivery Efficiency

As described herein, a device can be configured to deliver a substantial fraction of a single dose of a powdered therapeutic formulation (powdered composition) into a nostril of a subject. A device can be configured to deliver a substantial fraction of an amount of powdered therapeutic formulation residing within the device into a nostril of a subject. A powdered therapeutic formulation or a substantial fraction thereof can be delivered after a single activation of a device. Activation of a device can be, for example, compression of a flexible vial that serves as a manual air pump. A substantial fraction of a powdered therapeutic formulation can be delivered after multiple activations of a device, such as, for example 2, 3, 4, 5, 6, 7, 8, 9, or 10 activations. Multiple activations of a device can constitute a single use of a device. The substantial fraction of powdered therapeutic formulation that can be delivered by a device can be at least 50%, 55%, 60%, 65%, 70%, 75%, 80%, 85%, 90%, 90.5%, 91%, 91.5%, 92%, 92.5%, 93%, 93.5%, 94%, 94.5%, 95%, 95.5%, 96%, 96.5%, 97%, 97.5%, 98%, 98.5%, 99%, 99.1%, 99.2%, 99.3%, 99.4%, 99.5%, 99.5%, 99.6%, 99.7%, 99.8% 99.9%, 99.95%, or 100% of the amount of powdered therapeutic formulation such as the amount in a single dose or the amount residing in the device. The substantial fraction of powdered therapeutic formulation that can be delivered by a device can be about 50%, 55%, 60%, 65%, 70%, 75%, 80%, 85%, 90%, 90.5%, 91%, 91.5%, 92%, 92.5%, 93%, 93.5%, 94%, 94.5%, 95%, 95.5%, 96%, 96.5%, 97%, 97.5%, 98%, 98.5%, 99%, 99.1%, 99.2%, 99.3%, 99.4%, 99.5%, 99.5%, 99.6%, 99.7%, 99.8% 99.9%, 99.95%, or 100% of the amount of powdered therapeutic formulation such as the amount in a single dose or the amount residing in the device. In some instances, about 60-100%, 60-99%, 60-95%, 60-90%, 60-85%, 60-80%, 60-75%, 60-70%, 70-100%, 70-99%, 70-95%, 70-90%, 70-85%, 70-80%, 75-100%, 75-99%, 75-95%, 75-90%, 75-85%, 75-80%, 80-100%, 80-99%, 80-95%, 80-90%, 80-85%, 85-100%, 85-99%, 85-95%, 85-90%, 90-100%, 90-99%, 90-95%, 95-100%, or 95-99% of the amount of powdered therapeutic formulation is expelled from the device after the first activation. In such instances, a second activation can result in expulsion of substantially all of the powdered therapeutic formulation. The remainder of 1% or less of the powdered therapeutic formulation in the device, typically as a residual powder on the walls of the chamber, can constitute delivery of substantially all of the powdered therapeutic formulation.

A. Nozzle

Provided herein are nozzles adapted to deliver a powdered therapeutic formulation to a nostril of a subject. In one embodiment, a nozzle is adapted to be placed partially or completely into a nostril of a subject during use. In another embodiment, a nozzle is adapted to be placed externally and adjacent to a nostril, totally or partially covering the opening of a nostril.

Nozzle Shape

A nozzle disclosed herein is not limited to a particular shape. A nozzle can be of a uniform width such as in the shape of a cylinder, a cuboid, a rhombohedron, or a parallelepiped. A nozzle can also be a funnel or frustum shape, with a wide end and a narrow end. The shape of a nozzle can be wider at the upstream end and narrower at the downstream end. A nozzle can be wider at the downstream end and narrower at the upstream end. In other embodiments, the widest and narrowest sections of a nozzle, however, are not be at any end. For example, the widest section of a nozzle can be at any position along the upstream to downstream axis. In nozzles where the widest section is found mid-length along the axis, the widest section can function as a stop that prevents the nozzle from being inserted further into a nostril. In some embodiments, a nozzle is composed of two or more shapes such as any of the shapes provided herein. For example, a nozzle can include a cylinder shaped portion and a cone shaped portion. The nozzle can include a section, e.g., a nozzle pipe, designed for insertion into a nostril and a section, e.g., a nozzle base, designed for attachment to an air source, for example, attachment to the throat of a flexible vial.

Nozzle Material

A nozzle can be composed of a variety of polymers, plastics, rubber, silicones, metal, composites, any other materials described herein as suitable for use in the manufacture of a device applicator, or any other material suitable for use as an applicator nozzle. A nozzle can be made of one material or type of material. A nozzle can be composed two or more different materials or types of materials. All or a portion of a nozzle can be a biocompatible material or a hypoallergenic material. In some embodiments, a nozzle is comprised of one or more of silicone, styrene butadiene block copolymer (SBS), polyacetal, polyoxymethylene, acrylates, polyethylenes, polyurethane, hydrogel, polyester (e.g., DACRONB from E. I. Du Pont de Nemours and Company, Wilmington, Del.), polypropylene, polytetrafluoroethylene (PTFE), expanded PTFE (ePTFE), polyether ether ketone (PEEK), nylon, extruded collagen, polymer foam, rubber, silicone rubber, polyethylene terephthalate, ultra high molecular weight polyethylene, polycarbonate urethane, polyimides, aluminum, stainless steel, nickel-titanium alloy (e.g., Nitinol), titanium, stainless steel, or cobalt-chrome alloy (e.g., ELGILOYB from Elgin Specialty Metals, Elgin, Ill.; CONICHROMEB from Carpenter Metals Corp., Wyomissing, Pa.).

Nozzle Opaqueness

A nozzle can be composed partially or entirely of clear or translucent materials. The use of a clear or translucent nozzle can allow for the visual inspection of the nozzle to ascertain whether there is appreciable residual powdered therapeutic formulation (powdered composition) remaining in a reservoir after use. If, upon inspection, a subject notices that there is a residual powdered therapeutic formulation in a reservoir, the subject can activate an air source once or multiple times and then check by visual inspection of the clear or translucent nozzle to see if there was sufficient delivery. This process can be repeated as needed to ensure that an adequate dose is delivered. The nozzle can be composed partially or entirely of opaque or substantially opaque materials. For example, if the device contains a light-sensitive powdered therapeutic formulation, an opaque nozzle or substantially opaque material can protect the light-sensitive powdered therapeutic formulation from exposure to light.

Nozzle Rigidity

A nozzle material can be a soft, pliable or malleable material such that the nozzle can conform to the shape of a nostril of a subject. A nozzle can be composed of rigid, substantially rigid, flexible, or substantially flexible materials, or a combination thereof. A nozzle can be a rigid material such as a polymer, plastic, silicone, metal, or a composite at one end, and a soft, malleable, or pliable material at another end, such as, for example the end of the nozzle that is placed in the nostril. The soft, pliable, or malleable material can provide the advantage of reducing the likelihood of injury during contact between a nostril of a subject and the nozzle. The reduction of likelihood of an injury can be useful if a device is used by a third party such as a doctor, a nurse, a nursing home attendant, an emergency medical technician, a paramedic, a parent, a guardian or other caregiver to deliver a powdered therapeutic formulation to a subject (e.g., a child or an elderly person).

Nozzle/Nasal Insertion

In some embodiments, a nozzle is of a size to substantially fit inside a nostril of a subject. For example, at least 10%, 20%, 25%, 30%, 40%, 50%, 60%, 70%, 75%, 80%, 90%, or 95% of the nozzle can fit inside a nostril of a subject during use of a device. Less than about 10%, 20%, 25%, 30%, 40%, 50%, 60%, 70%, 75%, 80%, 90%, or 95% of the nozzle can fit inside a nostril of a subject during use of a device. Between about 5% and about 90% of the nozzle of a device can fit inside the nostril of a subject during use of a device. In other embodiments, between about 5% and 75%, 10% and 50%, 10% and 30%, 20% and 60% or 30% and 90% of the nozzle of a device can fit inside the nostril of a subject during use of a device. About 10%, 20%, 25%, 30%, 40%, 50%, 60%, 70%, 75%, 80%, 90%, or 95% of the nozzle can fit inside a nostril of a subject during use of a device.

Nozzle Pipe/Nasal Insertion

The nozzle can comprise a nozzle pipe for insertion into a nostril and a base section, e.g., for attachment to an air source. In some embodiments, a nozzle pipe is of a size to substantially fit inside a nostril of a subject. For example, at least 10%, 20%, 25%, 30%, 40%, 50%, 60%, 70%, 75%, 80%, 90%, or 95% of the nozzle pipe can fit inside a nostril of a subject during use of a device. Less than 10%, 20%, 25%, 30%, 40%, 50%, 60%, 70%, 75%, 80%, 90%, or 95% of the nozzle pipe can fit inside a nostril of a subject during use of a device. Between about 5% and about 90% of the nozzle pipe of a device can fit inside the nostril of a subject during use of a device. In other embodiments, between about 5% and 75%, 10% and 50%, 10% and 30%, 20% and 60% or 30% and 90% of the nozzle pipe of a device can fit inside the nostril of a subject during use of a device. About 10%, 20%, 25%, 30%, 40%, 50%, 60%, 70%, 75%, 80%, 90%, or 95% of the nozzle pipe can fit inside a nostril of a subject during use of a device. In some embodiments, a nozzle base section can fit inside a nostril of a subject. For example, at least 10%, 20%, 25%, 30%, 40%, 50%, 60%, 70%, 75%, 80%, 90%, or 95% of the nozzle base can fit inside a nostril of a subject during use of a device. Less than 10%, 20%, 25%, 30%, 40%, 50%, 60%, 70%, 75%, 80%, 90%, or 95% of the nozzle base can fit inside a nostril of a subject during use of a device. Between about 5% and about 90% of the nozzle base of a device can fit inside the nostril of a subject during use of a device. In other embodiments, between about 5% and 75%, 10% and 50%, 10% and 30%, 20% and 60% or 30% and 90% of the nozzle base of a device can fit inside the nostril of a subject during use of a device. About 10%, 20%, 25%, 30%, 40%, 50%, 60%, 70%, 75%, 80%, 90%, or 95% of the nozzle base can fit inside a nostril of a subject during use of a device. Alternatively, in some embodiments, the nozzle base section does not fit inside a nostril of the subject.

Nozzle Length

The length of nozzle can be measured from an upstream end to a downstream end, where upstream and downstream denote the direction of flow of air or other propellant during operation of a device (i.e. air or other propellant can flow from upstream to downstream). The length of a nozzle can include the length of a nozzle pipe and a nozzle base section.

The length of nozzle can be the length of a nozzle pipe. The upstream to downstream length of the nozzle can be less than about 5 cm, less than about 4.5 cm, less than about 4 cm, less than about 3.5 cm, less than about 3 cm, less than about 2.5 cm, less than about 2 cm, less than about 1.5 cm, less than about 1.0 cm, or less than about 0.5 cm. The length of the nozzle can be between about 0.5 cm and 5 cm, between about 1 cm and 5 cm, between about 1 cm and 4 cm, between about 1 cm and 3 cm, between about 2 cm and 5 cm, or between about 2 cm and 4 cm in length. The length of the nozzle can be about 0.5 cm, 1 cm, 1.5 cm, 2 cm, 2.5 cm, 3 cm, 3.5 cm, 4 cm, 4.5 cm, or 5 cm. The length of the nozzle can be more than about 0.5 cm, 1 cm, 1.5 cm, 2 cm, 2.5 cm, 3 cm, 3.5 cm, 4 cm, 4.5 cm, or 5 cm.

Nozzle Pipe Length

A nozzle can comprise a nozzle pipe for insertion into a nostril and a throat section for attachment to an air source. The length of a nozzle pipe can be measured from an upstream end to a downstream end, where upstream and downstream denote the direction of flow of air or other propellant during operation of a device (i.e. air or other propellant can flow from upstream to downstream). The upstream to downstream length of the nozzle pipe can be less than about 5 cm, less than about 4.5 cm, less than about 4 cm, less than about 3.5 cm, less than about 3 cm, less than about 2.5 cm, less than about 2 cm, less than about 1.5 cm, or less than about 1.0 cm. The length of the nozzle pipe can be between about 0.5 cm and 5 cm, between about 1 cm and 5 cm, between about 1 cm and 4 cm, between about 1 cm and 3 cm, between about 2 cm and 5 cm, or between about 2 cm and 4 cm in length. The length of the nozzle pipe can be about 0.5 cm, 1 cm, 1.5 cm, 2 cm, 2.5 cm, 3 cm, 3.5 cm, 4 cm, 4.5 cm, or 5 cm. The length of the nozzle pipe can be more than about 0.5 cm, 1 cm, 1.5 cm, 2 cm, 2.5 cm, 3 cm, 3.5 cm, 4 cm, 4.5 cm, or 5 cm.

External Nozzle Width

In some embodiments, the external width perpendicular to the upstream to downstream axis of the nozzle at its widest section is between about 0.1 cm to 4 cm, 1 cm to about 4 cm, 1 cm to about 3 cm, 1 cm to about 2 cm, 2 cm to about 4 cm, or 2 cm to about 3 cm, 0.1 cm to 2 cm, 0.5 cm to 2 cm, or 1 cm to 2 cm. In some embodiments, the external width perpendicular to the upstream to downstream axis of the nozzle at its widest section is no more than about 0.5 cm, 1 cm, 1.5 cm, 2 cm, 2.5 cm, 3 cm, 3.5 cm, 4 cm, 4.5 cm, or 5 cm wide. In some embodiments, the external width perpendicular to the upstream to downstream axis of the nozzle at its widest section is about 0.1 cm, 0.2 cm, 0.3 cm, 0.4 cm, 0.5 cm, 0.6 cm, 0.7 cm, 0.8 cm, 0.9 cm, 1.0 cm, 1.2 cm, 1.4 cm, 1.6 cm, 1.8 cm, 2.0 cm, 2.2 cm, 2.4 cm, 2.6 cm, 2.8 cm, 3 cm, 3.2 cm, 3.4 cm, 3.6 cm, 3.8 cm, 4 cm, 4.2 cm, 4.4 cm, 4.6 cm, 4.8 cm, or 5 cm. In some embodiments, the external width perpendicular to the upstream to downstream axis of the nozzle at its widest section is more than about 0.1 cm, 0.2 cm, 0.3 cm, 0.4 cm, 0.5 cm, 0.6 cm, 0.7 cm, 0.8 cm, 0.9 cm, 1.0 cm, 1.2 cm, 1.4 cm, 1.6 cm, 1.8 cm, 2.0 cm, 2.2 cm, 2.4 cm, 2.6 cm, 2.8 cm, 3 cm, 3.2 cm, 3.4 cm, 3.6 cm, 3.8 cm, 4 cm, 4.2 cm, 4.4 cm, 4.6 cm, 4.8 cm, or 5 cm.

In some embodiments, the external width perpendicular to the upstream to downstream axis of the nozzle at its narrowest section is no more than about 0.1 cm, 0.25 cm, 0.5 cm, 0.75 cm, 1.0 cm, 1.5 cm, 2.0 cm, 2.5 cm, or 3.0 cm. In some embodiments, the external width perpendicular to the upstream to downstream axis of the nozzle at its narrowest section lies within the range of 0.5 cm to 3.0 cm; 1.0 to 2.5 cm or 1.0 to 2.0 cm, 0.1 cm to 2.0 cm, 0.5 cm to 1.5 cm. In some embodiments, the external width perpendicular to the upstream to downstream axis of the nozzle at its narrowest section is about 0.1 cm, 0.2 cm, 0.3 cm, 0.4 cm, 0.5 cm, 0.6 cm, 0.7 cm, 0.8 cm, 0.9 cm, 1.0 cm, 1.2 cm, 1.4 cm, 1.6 cm, 1.8 cm, 2.0 cm, 2.2 cm, 2.4 cm, 2.6 cm, 2.8 cm, 3 cm, 3.2 cm, 3.4 cm, 3.6 cm, 3.8 cm, 4 cm, 4.2 cm, 4.4 cm, 4.6 cm, 4.8 cm, or 5 cm. In some embodiments, the external width perpendicular to the upstream to downstream axis of the nozzle at its narrowest section is more than about 0.1 cm, 0.2 cm, 0.3 cm, 0.4 cm, 0.5 cm, 0.6 cm, 0.7 cm, 0.8 cm, 0.9 cm, 1.0 cm, 1.2 cm, 1.4 cm, 1.6 cm, 1.8 cm, 2.0 cm, 2.2 cm, 2.4 cm, 2.6 cm, 2.8 cm, 3 cm, 3.2 cm, 3.4 cm, 3.6 cm, 3.8 cm, 4 cm, 4.2 cm, 4.4 cm, 4.6 cm, 4.8 cm, or 5 cm.

The width of the nozzle can vary continuously, can vary in a step-wise fashion, does not vary, or a combination thereof. The inner width or the outer width of the nozzle can vary continuously, can vary in a step-wise fashion, does not vary, or a combination thereof. The upstream and downstream ends of the nozzle can be the same width or different. In some embodiments, the narrowest end is the end that is placed in a nostril of a subject before and during administration. In some embodiments, the widest and narrowest sections of a nozzle are at the ends. For example, the widest section of a nozzle can be at the upstream end and the narrowest section of the nozzle can be at the downstream end, or vice versa. In some embodiment, the widest and/or narrowest sections of a nozzle are not at the end. In some embodiments, the widest section of a nozzle houses a powdered therapeutic formulation reservoir. In some embodiments, the widest section of a nozzle is a nozzle base for attachment to a manual air pump.

Internal Nozzle Width

In some embodiments, the internal width perpendicular to the upstream to downstream axis of the nozzle at its widest section is between about 0.1 cm to 4 cm, 1 cm to about 4 cm, 1 cm to about 3 cm, 1 cm to about 2 cm, 2 cm to about 4 cm, or 2 cm to about 3 cm, 0.1 cm to 2 cm, 0.5 cm to 2 cm, or 1 cm to 2 cm. In some embodiments, the internal width perpendicular to the upstream to downstream axis of the nozzle at its widest section is no more than about 0.5 cm, 1 cm, 1.5 cm, 2 cm, 2.5 cm, 3 cm, 3.5 cm, 4 cm, 4.5 cm, or 5 cm wide. In some embodiments, the internal width perpendicular to the upstream to downstream axis of the nozzle at its widest section is more than about 0.5 cm, 1 cm, 1.5 cm, 2 cm, 2.5 cm, 3 cm, 3.5 cm, 4 cm, 4.5 cm, or 5 cm wide. In some embodiments, the internal width perpendicular to the upstream to downstream axis of the nozzle at its widest section is about 0.1 cm, 0.2 cm, 0.3 cm, 0.4 cm, 0.5 cm, 0.6 cm, 0.7 cm, 0.8 cm, 0.9 cm, 1.0 cm, 1.2 cm, 1.4 cm, 1.6 cm, 1.8 cm, 2.0 cm, 2.2 cm, 2.4 cm, 2.6 cm, 2.8 cm, 3 cm, 3.2 cm, 3.4 cm, 3.6 cm, 3.8 cm, 4 cm, 4.2 cm, 4.4 cm, 4.6 cm, 4.8 cm, or 5 cm.

In some embodiments, the internal width perpendicular to the upstream to downstream axis of the nozzle at its narrowest section is no more than about 0.1 cm, 0.25 cm, 0.5 cm, 0.75 cm, 1.0 cm, 1.5 cm, 2.0 cm, 2.5 cm, or 3.0 cm. In some embodiments, the internal width perpendicular to the upstream to downstream axis of the nozzle at its narrowest section is more than about 0.1 cm, 0.25 cm, 0.5 cm, 0.75 cm, 1.0 cm, 1.5 cm, 2.0 cm, 2.5 cm, or 3.0 cm. In some embodiments, the internal width perpendicular to the upstream to downstream axis of the nozzle at its narrowest section lies within the range of 0.5 cm to 3.0 cm; 1.0 to 2.5 cm or 1.0 to 2.0 cm, 0.1 cm to 2.0 cm, 0.5 cm to 1.5 cm. In some embodiments, the internal width perpendicular to the upstream to downstream axis of the nozzle at its narrowest section is about 0.1 cm, 0.2 cm, 0.3 cm, 0.4 cm, 0.5 cm, 0.6 cm, 0.7 cm, 0.8 cm, 0.9 cm, 1.0 cm, 1.2 cm, 1.4 cm, 1.6 cm, 1.8 cm, 2.0 cm, 2.2 cm, 2.4 cm, 2.6 cm, 2.8 cm, 3 cm, 3.2 cm, 3.4 cm, 3.6 cm, 3.8 cm, 4 cm, 4.2 cm, 4.4 cm, 4.6 cm, 4.8 cm, or 5 cm.

Nozzle Internal Volume

The nozzle can be hollow and can contain an internal volume. The internal volume of a nozzle can be about 5 cm$^3$ or less, 4 cm$^3$ or less, 3 cm$^3$ or less, 2 cm$^3$ or less, 1 cm$^3$ or less, 0.5 cm$^3$ or less. In some embodiments, the internal volume of a nozzle is between about 1 cm$^3$ and about 5 cm$^3$, between about 1 cm$^3$ and about 4 cm$^3$, between about 1 cm$^3$ and about 3 cm$^3$, between about 1 cm$^3$ and about 2 cm$^3$, between about 0.1 cm$^3$ and 2 cm$^3$, and between about 0.1 cm$^3$ and about 1 cm$^3$. The internal volume of the nozzle can be about 0.1, 0.2, 0.3, 0.4, 0.5, 0.6, 0.7, 0.8, 0.9, 1.0, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, or 5.0 cm$^3$. The internal volume of the nozzle can be more than about 0.5, 1, 1.5, 2, 2.5, 3, 3.5, 4, 4.5, or 5 cm$^3$. The internal volume of the nozzle can be less than about 0.5, 1, 1.5, 2, 2.5, 3, 3.5, 4, 4.5, or 5 cm$^3$.

Nozzle as a Reservoir

A nozzle can comprise a powdered therapeutic formulation reservoir adapted to contain a powdered therapeutic formulation for delivery into a nostril of a subject. In some instances, a powdered therapeutic reservoir is formed entirely by the nozzle. In other instances, a reservoir is formed in part by the nozzle and in part by a one way valve of a device and/or an air source or components thereof. For example, the downstream end of a reservoir can be formed by a nozzle, and the upstream end of a reservoir can be formed by one way valve and the air source and components thereof (see, e.g., FIG. 1). A reservoir can be an integral part of the nozzle in that it cannot be removed or replaced separately from removing or replacing the nozzle itself. A reservoir can be a separate replaceable, insertable, or removable part. In some embodiments, the replaceable, insertable, or removable reservoir takes the form of a capsule or cartridge. In some embodiments, the replaceable reservoir is not a capsule. There can be a one way valve or other means for regulating the flow of air, propellant, or powdered therapeutic from a reservoir. There can be a one way valve or other means for regulating the flow of air, propellant, or powdered therapeutic into a reservoir. In some embodiments, a nozzle houses a separate powdered therapeutic formulation reservoir that is disposed within the nozzle adapted to contain a powdered therapeutic formulation for delivery into the nostril of a subject. By designing the drug reservoir in the nozzle, close to the exit opening, the amount of residual drug after activation of the device can be minimized, e.g., for a sticky drug or for powders that stick to plastic due to, e.g., adhesivity, electrostatic, etc.

Nozzle Reservoir Volume

In some embodiments, a powdered therapeutic formulation reservoir is about 5 cm$^3$ or less, 4 cm$^3$ or less, 3 cm$^3$ or less, 2 cm$^3$ or less, 1 cm$^3$ or less, or 0.5 cm$^3$ or less in volume. In some embodiments, a powdered therapeutic formulation reservoir is between about 1 cm$^3$ and about 5 cm$^3$, between about 1 cm$^3$ and about 4 cm$^3$, between about 1 cm$^3$ and about 3 cm$^3$, between about 1 cm$^3$ and about 2 cm$^3$, between about 0.1 cm$^3$ and 2 cm$^3$, and between about 0.1 cm$^3$ and about 1 cm$^3$ in volume. A powdered therapeutic formulation reservoir can be about 0.1, 0.2, 0.3, 0.4, 0.5, 0.6, 0.7, 0.8, 0.9, 1.0, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, or 5.0 cm$^3$ in volume. A powdered therapeutic formulation reservoir can be more than about 0.5, 1, 1.5, 2, 2.5, 3, 3.5, 4, 4.5, or 5 cm$^3$ in volume. A powdered therapeutic formulation reservoir can be less than about 0.5, 1, 1.5, 2, 2.5, 3, 3.5, 4, 4.5, or 5 cm$^3$ in volume.

Amount of Powdered Therapeutic Formulation in the Reservoir

In some embodiments, a reservoir is suitable for storing a dose of a powdered therapeutic formulation of between about 10 mg and 2000 mg, between about 50 mg and 1500 mg, between about 100 mg and 1000 mg, between about 100 mg and 500 mg, between about 500 mg and 2000 mg, or between about 1000 mg and 2000 mg of a powdered therapeutic formulation. In some embodiments, a reservoir is suitable for storing at least 10 mg, 50 mg, 100 mg, 200 mg, 300 mg, 400 mg, 500 mg, 600 mg, 700 mg, 800 mg, 900 mg, 1000 mg, 1500 mg, or 2000 mg of a powdered therapeutic formulation. In some embodiments, a reservoir is suitable for storing at most 10 mg, 25 mg, 50 mg, 75 mg, 100 mg, 200 mg, 300 mg, 400 mg, 500 mg, 600 mg, 700 mg, 800 mg, 900 mg, 1000 mg, 1500 mg, or 2000 mg of a powdered therapeutic formulation. A reservoir can store about 10 mg, 25 mg, 50 mg, 75 mg, 100 mg, 200 mg, 300 mg, 400 mg, 500 mg, 600 mg, 700 mg, 800 mg, 900 mg, 1000 mg, 1500 mg, or 2000 mg of a powdered therapeutic formulation. In some embodiments, a reservoir is configured to hold a single dose of a powdered therapeutic formulation while in other embodiments a reservoir is configured to hold multiple (e.g., 2, 3, 4, 5, 6, 7, 8, 9, 10) doses of a powdered therapeutic formulation. A dose can refer to the amount of powdered therapeutic formulation that a subject uses at a time.

A reservoir can be filled with a powdered therapeutic formulation during manufacture of a device. A reservoir can be filled with a powdered therapeutic formulation prior to affixing or attaching the nozzle to an air source. A reservoir can be filled after affixing or attaching a nozzle to an air source or a combination thereof.

Internal Nozzle Wall and Slits

The internal nozzle wall can also comprise one or more slits (canals or grooves). A slit or groove can be formed by a curved surface (e.g., a semicircle; see e.g., FIG. 2D), two surfaces (see e.g., FIG. 2E), three surfaces (see e.g., FIG. 2F), four surfaces, five surfaces, six surfaces, seven surfaces, eight surfaces, nine surfaces, or 10 surfaces. An internal nozzle wall can have slits or grooves with at least 1, 2, 3, 4, 5, 6, 7, 8, 9, or 10 different forms. The one or more slits can be used to create a vortex in the reservoir of the device when the device is activated (e.g., when air enters a powdered therapeutic formulation reservoir from an air source). The vortex can enable complete delivery of the powdered therapeutic formulation. The one or more slits can be positioned to permit laminar air flow in the reservoir.

Slit or Groove Number

The internal nozzle wall can have at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 slits or grooves. The internal nozzle wall can have less than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 slits or grooves. The internal nozzle wall can have about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 slits or grooves. The internal nozzle wall can have about 1-100, 1-90, 1-80, 1-70, 1-60, 1-50, 1-40, 1-30, 1-25, 1-20, or 1-10 slits or grooves.

Slit or Groove Positioning

The slits or grooves can be substantially parallel to each other in the internal nozzle wall. In some embodiments, all the slits or grooves are not substantially parallel to each other in the internal nozzle wall. In some embodiments, all the slits or grooves are not evenly spaced in the internal nozzle wall. In some embodiments, all the slits or grooves are evenly spaced on the internal nozzle wall.

Slit or Groove Length

A slit can be about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 mm in length. A slit can be less than about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 mm in length. A slit can be more than about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 mm in length.

Powdered Therapeutic Formulation Reservoir Shape

A powdered therapeutic formulation reservoir is not limited to any particular shape and can be disposed within a nozzle as a sphere, an ellipsoid, a cylinder, a cuboid, a frustum, or any other suitable shape such as any of the shapes described herein. In some embodiments, the shape of a reservoir is chosen to minimize the presence of corners, sharp edges, or other surface features that can disrupt airflow. In some embodiments, the shape of a reservoir is chosen to eliminate areas that do not experience uniform, laminar or high airflow during operation of a device. This can have the effect of reducing places within a reservoir and the nozzle where the powdered therapeutic formulation can clump or accumulate and thereby lower the total amount of powdered therapeutic formulation delivered to the nostril of the subject. For example, the shape of a powdered therapeutic formulation reservoir can be a frustum, or parallelepiped in which all corners have been rounded off. In some embodiments, a powdered therapeutic formulation reservoir is composed of two or more shapes such as any of the shapes provided herein. For example, a powdered therapeutic formulation reservoir can include a cylinder shaped portion and a cone shaped portion. Alternatively, by way of example only, a powdered therapeutic formulation reservoir can include two cone shaped portions joined at their widest ends or two cone shaped portions linked by an intervening cylinder shaped portion. In some embodiments, the internal surface of the powdered therapeutic formulation reservoir is smooth. Alternatively, the internal surface can be rough. In some embodiments, one or more internal surface feature can be provided within the powdered therapeutic formulation reservoir. One or more ridges, grooves, protrusions, bumps, channels, or other surface features can be provided on the internal surface of the reservoir. Such surface features can affect the air flow and delivery of the powdered therapeutic formulation.

Nozzle Flow Restrictor

A nozzle can contain a flow restrictor adapted to restrict the flow of air through at least a portion of a device and thereby increase or decrease the velocity of, or redirect, the airflow within a device. In some embodiments, a flow restrictor is at the downstream end of the nozzle. A flow restrictor can be at the upstream end of the nozzle. There can be a flow restrictor at both the upstream and downstream end of a nozzle. In some embodiments, a flow restrictor is disposed at the downstream end of the nozzle and smoothly narrows in width from the upstream to the downstream end. Alternatively, a flow restrictor can narrow in a stepwise fashion, or can narrow in a combination of stepwise and continuously from the upstream to the downstream end. This narrowing can provide for increased velocity of air and/or powdered therapeutic from the nozzle into the nostril of the subject during operation of a device. In some embodiments, a flow restrictor disposed at the downstream end of a nozzle narrows down to a nozzle hole from which air and powdered therapeutic exits the nozzle during operation.

Nozzle Flow Restrictor Shape

A flow restrictor can provide for the redirection of air or other propellant from along the inner walls of the nozzle and into the center of the airflow stream. A flow restrictor can be configured to direct the flow of air from along the inner walls of the nozzle in a laminar like fashion. A flow restrictor can be configured to direct the airflow into a powdered therapeutic formulation reservoir in a turbulent fashion. A flow restrictor can be configured to provide a vortex in at least a portion of a powdered therapeutic formulation reservoir during use of a device. The redirected flow of air provided by the flow restrictor can break up at least a portion of aggregates or clumps of a powdered therapeutic formulation present in a reservoir. The redirected flow of air can ensure that a substantial fraction of a powdered therapeutic formulation present in a reservoir is delivered to the nostril of a subject during routine use of a device. For example, the redirected flow of air provided by a flow restrictor can turbulently mix and therefore effectively aerosolize a powdered therapeutic. A flow restrictor can be any of a number of shapes including but not limited to a cone, a cylinder, tapered cylinder, a frustum, and a parallelepiped or any other shape provided herein, including a combination of one or more shapes.

Nozzle Flow Restrictor Width

A flow restrictor can vary in width from slightly smaller than the width of a nozzle down to the width of a nozzle hole. For example, a flow restrictor can vary in width from at least about 0.1 mm, 0.2 mm, 0.3 mm, 0.4 mm, 0.5 mm, 0.6 mm, 0.7 mm, 0.8 mm, 0.9 mm, 1 mm, 1.5 mm, 2 mm, 2.5 mm, 3 mm, 4 mm, 5 mm, 6 mm, 7 mm, 8 mm, 9 mm, 10 mm, 11 mm, 12 mm, 13 mm, 14 mm, or 15 mm at the widest part to less than about 0.1 mm, 0.2 mm, 0.3 mm, 0.4 mm, 0.5 mm, 0.6 mm, 0.7 mm, 0.8 mm, 0.9 mm, 1 mm, 2 mm, 3 mm, 4 mm, 5 mm, 6 mm, 7 mm, 8 mm, 9 mm, or 10 mm at the narrowest section of the flow restrictor. A flow restrictor can be at its widest point between about 5 mm and about 15 mm wide, or between about 8 mm and 12 mm. A flow restrictor can be at its narrowest point between about 1 mm and about 10 mm wide, between about 2 mm and 7 mm wide, about 0.1 mm to 2 mm wide, or about 0.5 mm to about 1.5 mm wide.

Nozzle Flow Restrictor Length

A flow restrictor can have an upstream to downstream length of at least 20 mm, 15 mm, 10 mm, 5 mm, 4 mm, 3 mm, 2 mm, or 1 mm. A flow restrictor can have an upstream to downstream length of less than 20 mm, 15 mm, 10 mm, 5 mm, 4 mm, 3 mm, 2 mm, or 1 mm. A flow restrictor can be between about 5 mm and about 20 mm long, between about 5 mm and about 15 mm long, between about 5 mm and about 10 mm long, between about 1 mm and about 5 mm long, or between about 0.5 mm and about 2.5 mm long. A flow restrictor can be about 0.5 mm, 1 mm, 1.5 mm, 2 mm, 2.5 mm, 3 mm, 3.5 mm, 4 mm, 4.5 mm, 5 mm, 5.5 mm, 6 mm, 6.5 mm, 7 mm, 7.5 mm, 8 mm, 8.5 mm, 9 mm, 9.5 mm, or 10 mm long.

Nozzle Hole

A nozzle hole can be adapted to allow the exit of a powdered therapeutic formulation from the nozzle as a single stream. In some embodiments, a nozzle has multiple holes that can emit a powdered therapeutic formulation as multiple streams that remain separate or that can combine into a single stream. In some embodiments, a nozzle hole is disposed at the downstream end of the nozzle. In some embodiments, a nozzle hole is also the downstream end of the flow restrictor. A nozzle hole can be any of a number of shapes including but not limited to a circle, oval, triangle, rectangle, or combination thereof. In some embodiments, a nozzle is configured to provide a high velocity of propellant and/or powdered therapeutic into the nostril of a subject. For example, a nozzle can be configured to provide a peak propellant velocity of between about 1 m/s to about 10 m/s, about 2 m/s to about 8 m/s or about 3 m/s to about 6 m/s.

Nozzle Hole Width

In some embodiments, the size of the nozzle hole when there is only one hole, when measured at its widest section, is less than 20 mm, less than about 15 mm, less than about 12 mm, less than about 10 mm, less than about 8 mm, less than about 5 mm, less than about 3 mm, less than about 2 mm, less than about 1 mm, or less than about 0.5 mm. In embodiments where there is more than one nozzle hole the width of individual holes is less than 10 mm, less than about 8 mm, less than about 6 mm, less than about 5 mm, less than about 4 mm, less than about 3 mm, less than about 2 mm, less than about 1 mm, or less than about 0.5 mm. The width of the nozzle hole at its widest section can be about 0.1 mm, 0.15 mm, 0.2 mm, 0.25 mm, 0.3 mm, 0.35 mm, 0.4 mm, 0.45 mm, 0.5 mm, 0.55 mm, 0.6 mm, 0.65 mm, 0.7 mm, 0.75 mm, 0.8 mm, 0.9 mm, 1 mm, 1.1 mm, 1.2 mm, 1.3 mm, 1.4 mm, 1.5 mm, 1.6 mm, 1.7 mm, 1.8 mm, 1.9 mm, 2.0 mm, 2.1 mm, 2.2 mm, 2.3 mm, 2.4 mm, 2.5 mm, 2.6 mm, 2.7 mm, 2.8 mm, 2.9 mm, 3.0 mm. A nozzle hole at its widest section can be more than about 0.1 mm, 0.15 mm, 0.2 mm, 0.25 mm, 0.3 mm, 0.35 mm, 0.4 mm, 0.45 mm, 0.5 mm, 0.55 mm, 0.6 mm, 0.65 mm, 0.7 mm, 0.75 mm, 0.8 mm, 0.9 mm, 1 mm, 1.1 mm, 1.2 mm, 1.3 mm, 1.4 mm, 1.5 mm, 1.6 mm, 1.7 mm, 1.8 mm, 1.9 mm, 2.0 mm, 2.1 mm, 2.2 mm, 2.3 mm, 2.4 mm, 2.5 mm, 2.6 mm, 2.7 mm, 2.8 mm, 2.9 mm, 3.0 mm. A nozzle hole at its widest section can be less than about 0.1 mm, 0.15 mm, 0.2 mm, 0.25 mm, 0.3 mm, 0.35 mm, 0.4 mm, 0.45 mm, 0.5 mm, 0.55 mm, 0.6 mm, 0.65 mm, 0.7 mm, 0.75 mm, 0.8 mm, 0.9 mm, 1 mm, 1.1 mm, 1.2 mm, 1.3 mm, 1.4 mm, 1.5 mm, 1.6 mm, 1.7 mm, 1.8 mm, 1.9 mm, 2.0 mm, 2.1 mm, 2.2 mm, 2.3 mm, 2.4 mm, 2.5 mm, 2.6 mm, 2.7 mm, 2.8 mm, 2.9 mm, 3.0 mm. A nozzle hole at its widest section can be in a range from about 0.1 mm to 2 mm, 0.5 mm to 1.5 mm, or 0.75 mm to 1.25 mm.

Nozzle Hole Depth

In some embodiments, the upstream to downstream depth of a nozzle hole, that is the length of the channel formed from the surface of a nozzle at the site of the hole to the tip of a reservoir or flow restrictor, is less than about 50 mm, less than about 40 mm, less than about 30 mm, less than about 25 mm, less than about 20 mm, less than about 15 mm, less than about 10 mm, less than about 7 mm, less than about 5 mm, less than about 3 mm, or less than about 1 mm. In some embodiments, the surface of a nozzle at the site of the hole is the downstream top of a reservoir or flow restrictor effectively producing a depth of 0 mm. A nozzle hole depth can be more than about 0.1 mm, 0.25 mm, 0.5 mm, 0.75 mm, 1 mm, 1.5 mm, 2 mm, 3 mm, 4 mm, 5 mm, 6 mm, 7 mm, 8 mm, 9 mm, 10 mm, 12.5 mm, 15 mm, 17.5 mm, 20 mm, 22.5 mm, 25 mm, 27.5 mm, 30 mm, 35 mm, 40 mm, 45 mm, or 50 mm. A nozzle hole depth can be about 0.1 mm, 0.25 mm, 0.5 mm, 0.75 mm, 1 mm, 1.5 mm, 2 mm, 3 mm, 4 mm, 5 mm, 6 mm, 7 mm, 8 mm, 9 mm, 10 mm, 12.5 mm, 15 mm, 17.5 mm, 20 mm, 22.5 mm, 25 mm, 27.5 mm, 30 mm, 35 mm, 40 mm, 45 mm, or 50 mm.

Nozzle Base

A nozzle can also include a base. A base can be adapted to provide for a flow of air from a manual air chamber to a powdered therapeutic formulation reservoir or a nozzle. In some embodiments, a base is at the upstream end of a nozzle. A throat can additionally or alternatively be at the upstream end of a reservoir. In some embodiments, a base is a part of a nozzle. A base can form part of the upstream end of a powdered therapeutic formulation reservoir. In some embodiments, a base is partially formed by a nozzle and partially formed by a one way valve. In some embodiments, a base can accommodate all or part of a one way valve.

A base can be configured to provide for air or propellant egress from a manual air pump, thereby allowing it to enter a nozzle and/or powdered therapeutic formulation reservoir. In some embodiments, a base is configured to house a one way valve or a portion of a one way valve. In some embodiments, a throat is configured to slidably house a one way valve or a portion of a one way valve. In some embodiments, a one way valve disposed within a base restrains a powdered therapeutic formulation inside a nozzle from moving upstream such as into an air source. A base can be any number of shapes including but not limited to a cone, a cylinder, tapered cylinder, a frustum, and a parallelepiped or any other shape provided herein, including a combination of one or more shapes.

In some embodiments, the upstream to downstream length of a base is less than 20 mm, less than 15 mm, less than 12 mm, less than 11 mm, less than 10 mm, less than 9 mm, less than 8 mm, less than 7 mm, less than 6 mm, less than 5 mm, less than 4 mm, or less than 2 mm. In some instances, the upstream to downstream length of a base is between about 2 mm and 20 mm, between about 5 mm and 15 mm, or between about 5 mm and 10 mm.

In some embodiments, the width perpendicular to the upstream to downstream axis of a base at its widest section is between about 2 mm to about 10 mm, about 2 mm to about 8 mm, or about 2 mm to about 5 mm. In some embodiments, the width perpendicular to the upstream to downstream axis of a base at its widest section is at least 1 mm, 2 mm, 3 mm, 4 mm, 5 mm, 6 mm, 7 mm, 8 mm, 9 mm, 10 mm wide, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, 26 mm, 27 mm, 28 mm, 29 mm, or 30 mm. The width perpendicular to the upstream to downstream axis of a base at its widest section can be about 1 mm, 2 mm, 3 mm, 4 mm, 5 mm, 6 mm, 7 mm, 8 mm, 9 mm, 10 mm wide, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, 26 mm, 27 mm, 28 mm, 29 mm, or 30 mm.

A throat base can comprise one or more threads for attachment to, for example, a manual air pump and/or flexible vial. The one or more threads can be used to screw the nozzle and manual air pump together.

Cover

A nozzle can include a cover. A cover can be positioned at the downstream end of a nozzle. Alternatively, or in addition, a cover can be positioned at the downstream end of a nozzle hole. A cover can be configured to inhibit an unintentional discharge of a device. For example, a cover can be air tight preventing any airflow out of the downstream end of a nozzle and thereby preclude accidental activation of an air source from leading to discharge of a powdered therapeutic formulation. Such accidental activations can occur by rough handling of a device such as during storage or shipping. A cover can also be configured to provide an environment suitable for storage of a powdered therapeutic formulation within a powdered therapeutic formulation reservoir. For example, a cover can inhibit or block the intrusion of outside air and/or water into a nozzle and thus inhibit or block the intrusion of air or water into a powdered medicine reservoir. A cover can be a replaceable cover, such that it can be removed and replaced. With a replaceable cap, a removable band can be employed to securely fasten a cap to a nozzle. Alternatively, a cover can be a removable or breakable cover such that it is removed once by breaking from a nozzle or can be removed and replaced (e.g, put back into place) one or more times. A cover can be a removable or breakable tab, or a removable or breakable membrane, or a removable or breakable cap (e.g., an airtight cap).

B. One Way Valve

Devices described herein comprise at least one one way valve. A one way valve can be configured to regulate the flow of air from an air source and into a nozzle of a device. A one way valve can further be configured to regulate the movement of powdered therapeutic formulation. A one way valve can be configured to block air or gas flow from an air source into a nozzle when the device is not activated (e.g., a manual air pump is not compressed) and can permit air or gas flow from an air source into a nozzle when the device is activated (e.g., a manual air pump is compressed).

In some embodiments, a one way valve is configured to block movement of powdered therapeutic formulation (e.g., by gravity) in an upstream direction (e.g., into an air source). A one way valve can be configured so it can be in one position in the device when the device is not activated (e.g., an air source is not activated) and another position in the device when the device is activated (e.g., an air source is activated). A one way valve can be configured to block movement of a powdered therapeutic formulation (e.g., by gravity) in an upstream direction (e.g., into a flexible vial and/or manual air pump) when the device is not activated (e.g., a manual air pump is not compressed) and when the device is activated (e.g., a manual air pump is compressed). The one way valve can contain slits (or channels or grooves) diagonal to a major axis of the device that can create a vortex along the walls of the reservoir.

One Way Valve Composition

A one way valve can be composed of a variety of polymers, plastics, rubber, silicones, metal, composites, any other materials described herein as suitable for use in the manufacture of an intranasal delivery device, or any other material suitable for use in an intranasal delivery device. A one way valve can be made of one material or type of material. Alternatively, a one way valve can be composed two or more different materials or types of materials. All or a portion of a one way valve can be a biocompatible material or a hypoallergenic material. A one way valve can be composed of rigid, substantially rigid, flexible, or substantially flexible materials, or a combination thereof. In some embodiments, a one way valve can be comprised of one or more of paper, silicone, styrene butadiene block copolymer (SBS), polyacetal, polyoxymethylene, acrylates, polyethylenes, polyurethane, hydrogel, polyester (e.g., DACRONB from E. I. Du Pont de Nemours and Company, Wilmington, Del.), polypropylene, polytetrafluoroethylene (PTFE), expanded PTFE (ePTFE), polyether ether ketone (PEEK), nylon, extruded collagen, polymer foam, rubber, silicone rubber, polyethylene terephthalate, ultra high molecular weight polyethylene, polycarbonate urethane, polyimides, aluminum, stainless steel, nickel-titanium alloy (e.g., Nitinol), titanium, stainless steel, or cobalt-chrome alloy (e.g., ELGILOYB from Elgin Specialty Metals, Elgin, Ill.; CONICHROMEB from Carpenter Metals Corp., Wyomissing, Pa.).

One Way Valve Dimensions

A one way valve can be any number of shapes including but not limited to a disc, an annulus, a torus, a cone, a pyramid, a cylinder, tapered cylinder, a frustum, a cuboid, and a parallelepiped or any other shape provided herein, including a combination of one or more shapes. A one way valve can have a narrow end and a wide end. In some embodiments, the widest portion of a one way valve cannot lie at the upstream or downstream end. In some embodiments, the narrowest portion of a one way valve cannot lie at the upstream or downstream end. A one way valve can be hollow. A one way valve can have an opening at one end. In some embodiments, a one way valve does not have an opening at one end.

The upstream to downstream length of a one way valve can be less than about 30, 29, 28, 27, 26, 25, 24, 23, 22, 21, 20, 19, 18, 17, 16, 15, 14, 13, 12, 11, 10, 9, 8, 7, 6, or 5 mm. The length of a one way valve can be between about 5 mm and 30 mm, between about 5 mm and 20 mm, between about 5 mm and 15 mm, or between about 5 mm and 10 mm. The length the a one way valve can be more than about 5, 6, 7, 8, 9, 10, 11, 12, 13, 14, 15, 16, 17, 18, 19, 20, 21, 22, 23, 24, 25, 26, 27, 28, 29, or 30 mm. The length of a one way valve can be about 5, 6, 7, 8, 9, 10, 11, 12, 13, 14, 15, 16, 17, 18, 19, 20, 21, 22, 23, 24, 25, 26, 27, 28, 29, or 30 mm.

The width perpendicular to the upstream to downstream axis of a one way valve at its widest section can be between about 1 mm to about 30 mm, about 1 mm to about 25 mm, about 1 mm to about 20 mm, about 1 mm to about 15 mm, about 1 mm to about 10 mm, or about 1 mm to about 5 mm. The width perpendicular to the upstream to downstream axis of a one way valve at its widest section can be more than about 1 mm, 2 mm, 3 mm, 4 mm, 5 mm, 6 mm, 7 mm, 8 mm, 9 mm, or 10 mm wide. The width perpendicular to the upstream to downstream axis of a one way valve at its widest section can be less than about 1 mm, 2 mm, 3 mm, 4 mm, 5 mm, 6 mm, 7 mm, 8 mm, 9 mm, or 10 mm wide.

The width perpendicular to the upstream to downstream axis of a one way valve at its narrowest section can be between about 1 mm to about 30 mm, about 1 mm to about 25 mm, about 1 mm to about 20 mm, about 1 mm to about 15 mm, about 1 mm to about 10 mm, or about 1 mm to about 5 mm. In some embodiments, a one way valve has a width at its narrowest section that is no more than about 0.5 mm, 1 mm, 2 mm, 3 mm, 4 mm, 5 mm, 6 mm, 7 mm, 8 mm, 9 mm wide, 10 mm, 11 mm, 12 mm, 13 mm, 14 mm, 15 mm, 16 mm, 17 mm, 18 mm, 19 mm, or 20 mm wide. In some embodiments, a one way valve has a width at its narrowest section that is more than about 0.5 mm, 1 mm, 2 mm, 3 mm, 4 mm, 5 mm, 6 mm, 7 mm, 8 mm, 9 mm wide, 10 mm, 11 mm, 12 mm, 13 mm, 14 mm, 15 mm, 16 mm, 17 mm, 18 mm, 19 mm, or 20 mm wide. The width perpendicular to the upstream to downstream axis of a one way valve at its widest section or narrowest section can be about 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, or 20 mm wide.

One Way Valve Dimensions Relative to Nozzle

A one way valve can be configured to slidably fit within part or all of a nozzle. The width of part of a one way valve can be less than the internal width of a nozzle pipe. For example, the width at the base of a top section (e.g., FIG. 1 (118)) and the width of a first cylindrical section (e.g., FIG. 1 (120)) can be less than the width of the widest part of a nozzle pipe (e.g., FIG. 1 (130)). The difference in width of a first cylindrical section of a one way valve and the internal width of the widest part a nozzle pipe can be about 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.30, 0.31, 0.32, 0.33, 0.34, 0.35, 0.36, 0.37, 0.38, 0.39, 0.40, 0.41, 0.42, 0.43, 0.44, 0.45, 0.46, 0.47, 0.48, 0.49, or 0.5 mm. The difference in width of a first cylindrical section of a one way valve and the internal width of the widest part a nozzle pipe can be less than about 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.30, 0.31, 0.32, 0.33, 0.34, 0.35, 0.36, 0.37, 0.38, 0.39, 0.40, 0.41, 0.42, 0.43, 0.44, 0.45, 0.46, 0.47, 0.48, 0.49, or 0.5 mm. The difference in width of a first cylindrical section of a one way valve and the internal width of the widest part a nozzle pipe can be more than about 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.30, 0.31, 0.32, 0.33, 0.34, 0.35, 0.36, 0.37, 0.38, 0.39, 0.40, 0.41, 0.42, 0.43, 0.44, 0.45, 0.46, 0.47, 0.48, 0.49, or 0.5 mm. The difference in width of a first cylindrical section (see e.g., FIG. 3 (118)) and the internal width of the widest part of a nozzle pipe (see e.g., FIG. 3 (130)) can permit air to flow from a manual air pump to the nozzle when the manual air pump is activated (see e.g., FIG. 3).

Top Section

A one way valve can have multiple sections (see, e.g., FIG. 2A). A one way valve can have a top section (see, e.g., FIG. 2A (118)) in the shape of, e.g., a cone, a pyramid, or a trapezoid. A top section can have a convex surface. A top section can allow a powdered therapeutic formulation to accumulate along the wall of a nozzle pipe to increase flow and assist in proper air flow when the intranasal delivery device is activated. In some embodiments, a top section can further comprise an additional section. The additional section can be connected to the top portion of the top section and can be in the shape of, e.g., a cone, a pyramid, or a trapezoid.

Top Section Height

The height of a top section of a one way valve can be about 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, or 20 mm. The height of the top section of a one way valve can be more than about 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, or 20 mm. The height of a top section of a one way valve can be less than about 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, or 20 mm. The height of the top section of a one way valve can be about 1 to 20 mm, about 1 to 10 mm, about 1 to 5 mm, or about 1 to 2.5 mm.

Top Section Width

The diameter of the bottom of a top section can be about 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, or 20 mm. The diameter of the bottom of a top section can be more than about 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, or 20 mm. The diameter of the bottom of a top section can be less than about 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, or 20 mm. The diameter of the bottom of a top section can be from about 1 to 20 mm, 1 to 10 mm, 1 to 7.5 mm, 1 to 5 mm, 2.5 to 20 mm, 2.5 to 10 mm, or 2.5 to 7.5 mm.

Top Section Angle

An angle formed by a surface of a top section of a one way valve and a plane parallel to the base of the top section can be an obtuse angle. An obtuse angle formed by a surface of a top section of a one way valve and a plane parallel to the base of the top section can be from about 179 degrees to about 91 degrees, from about 170 to 100 degrees, from about 160 to about 110 degrees, from about 150 to about 120 degrees, or from about 140 to about 130 degrees. An obtuse angle formed by a surface of a top section of a one way valve and a plane parallel to the base of the top section can be about 179, 178, 177, 176, 175, 174, 173, 172, 171, 170, 169, 168, 167, 166, 165, 164, 163, 162, 161, 160, 159, 158, 157, 156, 155, 154, 153, 152, 151, 150, 149, 148, 147, 146, 145, 144, 143, 142, 141, 140, 139, 138, 137, 136, 135, 134, 133, 132, 131, 130, 129, 128, 127, 126, 125, 124, 123, 122, 121, 120, 119, 118, 117, 116, 115, 114, 113, 112, 111, 110, 109, 108, 107, 106, 105, 104, 103, 102, 101, 100, 99, 98, 97, 96, 95, 94, 93, 92, or 91 degrees. An obtuse angle formed by a surface of a top section of a one way valve and a plane parallel to the base of the top section can be less than about 179, 178, 177, 176, 175, 174, 173, 172, 171, 170, 169, 168, 167, 166, 165, 164, 163, 162, 161, 160, 159, 158, 157, 156, 155, 154, 153, 152, 151, 150, 149, 148, 147, 146, 145, 144, 143, 142, 141, 140, 139, 138, 137, 136, 135, 134, 133, 132, 131, 130, 129, 128, 127, 126, 125, 124, 123, 122, 121, 120, 119, 118, 117, 116, 115, 114, 113, 112, 111, 110, 109, 108, 107, 106, 105, 104, 103, 102, 101, 100, 99, 98, 97, 96, 95, 94, 93, 92, or 91 degrees. An obtuse angle formed by a surface of a top section of a one way valve and a plane parallel to the base of the top section can be more than about 179, 178, 177, 176, 175, 174, 173, 172, 171, 170, 169, 168, 167, 166, 165, 164, 163, 162, 161, 160, 159, 158, 157, 156, 155, 154, 153, 152, 151, 150, 149, 148, 147, 146, 145, 144, 143, 142, 141, 140, 139, 138, 137, 136, 135, 134, 133, 132, 131, 130, 129, 128, 127, 126, 125, 124, 123, 122, 121, 120, 119, 118, 117, 116, 115, 114, 113, 112, 111, 110, 109, 108, 107, 106, 105, 104, 103, 102, 101, 100, 99, 98, 97, 96, 95, 94, 93, 92, or 91 degrees.

First Cylindrical Section of a One Way Valve

The top section can be connected at its base to a first cylindrical section. The width of the first cylindrical section (see e.g., FIG. 2A (120)) can be the same as the width of the base of a top section (see e.g., FIG. 2A (118)).

First Cylindrical Section Height

The height of a first cylindrical section of a one way valve can be about 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, or 20 mm. The height of the first cylindrical section of a one way valve can be more than about 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, or 20 mm. The height of a first cylindrical section of a one way valve can be less than about 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, or 20 mm. The height of the first cylindrical section of a one way valve can be about 1 to 20 mm, about 1 to 10 mm, about 1 to 7.5 mm, about 1 to 5 mm, about 2.5 to 20 mm, about 2.5 to 10 mm, about 2.5 to 7.5 mm, or about 2.5 to 5 mm.

First Cylindrical Section Width

The diameter of a first cylindrical section can be about 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, or 20 mm. The diameter of a first cylindrical section can be more than about 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, or 20 mm. The diameter of a first cylindrical section can be less than about 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, or 20 mm. The diameter of a first cylindrical section can be from about 1 to 20 mm, 1 to 10 mm, 1 to 7.5 mm, 1 to 5 mm, 2.5 to 20 mm, 2.5 to 10 mm, or 2.5 to 7.5 mm.

First Shelf of a One Way Valve

A one way valve can have a first shelf (see, e.g., FIG. 2A (122)) that can extend outward and downward from the base of a first cylindrical section of a one way valve (see e.g., FIG. 2A (116)). A first shelf can contain slits or grooves that regulate air flow when a device is activated. A first shelf can serve to block the upward movement of a one way valve in a nozzle pipe when a device is activated.

The shortest length of the surface of a first shelf from the base of the first cylindrical section to the top of a second cylindrical section can be about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5 mm. The shortest length of the surface of a first shelf from the base of the first cylindrical section to the top of a second cylindrical section can be more than about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5 mm. The shortest length of the surface of a first shelf from the base of the first cylindrical section to the top of a second cylindrical section can be less than about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5 mm. The shortest length of the surface of a first shelf from the base of the first cylindrical section to the top of a second cylindrical section can be about 0.1 to 5 mm, 0.1 to 4 mm, 0.1 to 3 mm, 0.1 to 2 mm, 0.1 to 1.75 mm, 0.1 to 1.5 mm, 0.1 to 1.25 mm, or 0.1 to 1 mm.

An angle formed between the side of the first cylindrical section and the surface of the first shelf can be between about 91 to 179 degrees, 100 to 170 degrees, 110 to 160 degrees, 120 to 150 degrees, or 130 to 140 degrees. An angle formed between the side of the first cylindrical section and the surface of the first shelf can be about 179, 178, 177, 176, 175, 174, 173, 172, 171, 170, 169, 168, 167, 166, 165, 164, 163, 162, 161, 160, 159, 158, 157, 156, 155, 154, 153, 152, 151, 150, 149, 148, 147, 146, 145, 144, 143, 142, 141, 140, 139, 138, 137, 136, 135, 134, 133, 132, 131, 130, 129, 128, 127, 126, 125, 124, 123, 122, 121, 120, 119, 118, 117, 116, 115, 114, 113, 112, 111, 110, 109, 108, 107, 106, 105, 104, 103, 102, 101, 100, 99, 98, 97, 96, 95, 94, 93, 92, or 91 degrees. An angle formed between the side of the first cylindrical section and the surface of the first shelf can be more than about 179, 178, 177, 176, 175, 174, 173, 172, 171, 170, 169, 168, 167, 166, 165, 164, 163, 162, 161, 160, 159, 158, 157, 156, 155, 154, 153, 152, 151, 150, 149, 148, 147, 146, 145, 144, 143, 142, 141, 140, 139, 138, 137, 136, 135, 134, 133, 132, 131, 130, 129, 128, 127, 126, 125, 124, 123, 122, 121, 120, 119, 118, 117, 116, 115, 114, 113, 112, 111, 110, 109, 108, 107, 106, 105, 104, 103, 102, 101, 100, 99, 98, 97, 96, 95, 94, 93, 92, or 91 degrees. An angle formed between the side of the first cylindrical section and the surface of the first shelf can be less than about 179, 178, 177, 176, 175, 174, 173, 172, 171, 170, 169, 168, 167, 166, 165, 164, 163, 162, 161, 160, 159, 158, 157, 156, 155, 154, 153, 152, 151, 150, 149, 148, 147, 146, 145, 144, 143, 142, 141, 140, 139, 138, 137, 136, 135, 134, 133, 132, 131, 130, 129, 128, 127, 126, 125, 124, 123, 122, 121, 120, 119, 118, 117, 116, 115, 114, 113, 112, 111, 110, 109, 108, 107, 106, 105, 104, 103, 102, 101, 100, 99, 98, 97, 96, 95, 94, 93, 92, or 91 degrees. An angle formed between the side of the first cylindrical section and the surface of the first shelf can be an obtuse angle.

First Shelf Dimensions Relative to Nozzle Pipe

A first shelf can be configured to have a diameter that is wider than the internal diameter of a nozzle pipe. A first shelf can be configured to contact the base of a nozzle with the device is activated. The first shelf can be configured to prevent the entire one way valve from entering a nozzle pipe with the device is activated. The first shelf can be configured to prevent a powdered therapeutic formulation from moving upstream in a manual air pump (e.g., a flexible vial) when the device is activated.

Slits or Grooves in a First Shelf

A first shelf can have one or more slits or grooves on the surface of the shelf. The slits can permit air flow from a manual air pump to a nozzle with the device is activated (e.g., by compression). The one or more slits can be used to create a vortex in the reservoir of the device when the device is activated (e.g., when air enters a powdered therapeutic formulation reservoir from an air source). The resulting vortex can enable complete delivery of the powdered therapeutic formulation. The slits or grooves can be positioned to permit laminar air flow in the reservoir.

Slit or Groove Length

A slit or groove (e.g., see FIG. 2A (128)) can extend from the base of a first cylindrical section (e.g., see FIG. 2A (120)) to the top of a second cylindrical section (e.g., see FIG. 2A (124)) on the surface of a first shelf (e.g., see FIG. 2A (122)) of a one way valve (e.g., see FIG. 2A (116)). A slit or groove can extend about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% of the shortest length from bottom of the first cylindrical section to the top of the second cylindrical section on the surface of the first shelf. A slit or groove can extend more than about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% of the shortest length from bottom of the first cylindrical section to the top of the second cylindrical section on the surface of the first shelf. A slit or groove can extend less than about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% of the shortest length from bottom of the first cylindrical section to the top of the second cylindrical section on the surface of the first shelf. A slit or groove can extend about 1-100%, 10-100%, 20-100%, 30-100%, 40-100%, 50-100%, 60-100%, 70-100%, 80-100%, or 90-100% of the shortest length from the bottom of the first cylindrical section to the top of the second cylindrical section on the surface of a first shelf on the surface of the first shelf Angle of Slit or Groove A slit or groove can lie at a 90 degree or non-90 degree angle relative to a line representing the shortest length from the bottom of the first cylindrical section to the top of the second cylindrical section on the surface of a first shelf. With respect to a line representing the shortest length from the bottom of the first cylindrical section to the top of the second cylindrical section on the surface of a first shelf, a slit or groove can be at an angle of about 0 to 90 degrees, 5 to 90 degrees, 10 to 80 degrees, 15 to 75 degrees, 20 to 70 degrees, 25 to 65 degrees, 30 to 60 degrees, 35 to 55 degrees, or 40 to 50 degrees. With respect to a line representing the shortest length from the bottom of the first cylindrical section to the top of the second cylindrical section on the surface of a first shelf, a slit or groove can be at an angle of about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90 degrees. With respect to a line representing the shortest length from the bottom of the first cylindrical section to the top of the second cylindrical section on the surface of a first shelf, a slit or groove can be at an angle of more than about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, or 89 degrees. With respect to a line representing the shortest length from the bottom of the first cylindrical section to the top of the second cylindrical section on the surface of a first shelf, a slit or groove can be at an angle of less than about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89 or 90 degrees. When the one or more slits are at a 0 degree angle (parallel to a line representing the shortest length from the bottom of the first cylindrical section to the top of the second cylindrical section on the surface of a first shelf) air can flow straight along the walls of the reservoir. When the slits are at an angle of greater than 0 degrees and less than 90 degrees, a vortex can be created along the walls of the reservoir, enabling complete delivery of the drug out of the reservoir.

Slit or Groove Depth

The maximum depth of a slit or groove can be about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% of the length of a slit or groove. The maximum depth of a slit or groove can be more than about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% of the length of a slit or groove. The maximum depth of a slit or groove can be less than about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% of the length of a slit or groove. The maximum depth of a slit or groove can be about 1 to 50%, 1 to 40%, 1 to 30%, 1 to 25%, 1 to 20%, 1 to 15%, 1 to 10%, 1 to 5%, or 1 to 2.5% of the length of a slit or groove.

Slit or Groove Shape

A slit or groove can be formed by a curved surface (e.g., a semicircle; see e.g., FIG. 2D), two surfaces (see e.g., FIG. 2E), three surfaces (see e.g., FIG. 2F), four surfaces, five surfaces, six surfaces, seven surfaces, eight surfaces, nine surfaces, or 10 surfaces. A first shelf can have slits or grooves with at least 1, 2, 3, 4, 5, 6, 7, 8, 9, or 10 different forms.

Slit or Groove Number

A first shelf of a one way valve can have at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 slits or grooves. A first shelf of a one way valve can have less than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 slits or grooves. A first shelf of a one way valve can have about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 slits or grooves. A first shelf of a one way valve have about 1-100, 1-90, 1-80, 1-70, 1-60, 1-50, 1-40, 1-30, 1-25, 1-20, or 1-10 slits or grooves.

Slit or Groove Positioning

When a first shelf has more than one slit or groove, the slits or grooves can be substantially parallel to each other. In some embodiments, all the slits or grooves are not substantially parallel to each other. In some embodiments, all the slits or grooves are not evenly spaced on the first shelf. In some embodiment, all the slits or grooves are evenly spaced on the first shelf Second Cylindrical Section A one way valve can have a second cylindrical section (see e.g., FIG. 2A (124)) below the first shelf.

Second Cylindrical Section Height

The height of a second cylindrical section of a one way valve can be longer than the height of a first cylindrical section. The height of a second cylindrical section of a one way valve can be shorter than the height of a first cylindrical section. The height of a second cylindrical section of a one way valve can be about 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, or 20 mm. The height of the first cylindrical section of a one way valve can be more than about 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, or 20 mm. The height of a first cylindrical section of a one way valve can be less than about 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, or 20 mm. The height of the first cylindrical section of a one way valve can be about 1 to 20 mm, about 1 to 10 mm, about 1 to 7.5 mm, about 1 to 5 mm, about 1 to 4 mm, about 1 to 3 mm, or about 1 to 2 mm.

Second Cylindrical Section Width

A second cylindrical section of a one way valve can be wider than a first cylindrical section of a one way valve. A second cylindrical section can be wider than the internal diameter of a nozzle pipe. A second cylindrical section can be narrower than the internal diameter of a nozzle pipe.

The diameter of a second cylindrical section can be about 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, or 20 mm. The diameter of a second cylindrical section can be more than about 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, or 20 mm. The diameter of a second cylindrical section can be less than about 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, or 20 mm. The diameter of a second cylindrical section can be from about 1 to 20 mm, 1 to 10 mm, 1 to 7.5 mm, 1 to 5 mm, 2.5 to 20 mm, 2.5 to 10 mm, or 2.5 to 7.5 mm.

Figure 5:
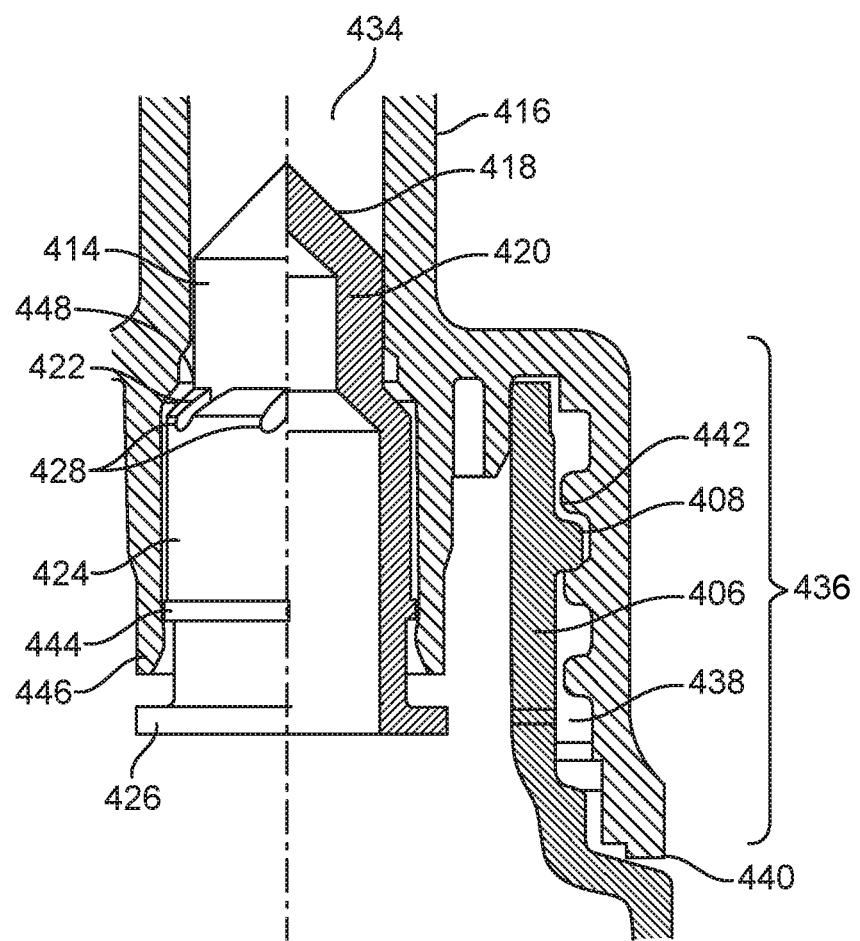
FIG. 5 illustrates a magnified view of a one way valve of the intranasal delivery device depicted in FIG. 4.

In some embodiments, a second cylindrical portion of a one way valve comprises a ridge (see e.g., FIG. 5 (444)). When a device is not activated, a ridge can rest on a bulge in the nozzle pipe (see e.g., FIG. 5 (446)). This positioning can prevent the one way valve from moving upstream in to a manual air pump. This positioning can also prevent a powdered therapeutic formulation from moving upstream into a manual air pump. The combination of the ridge and the second cylindrical section can be wider than the width of the second cylindrical section. A ridge can be positioned anywhere along the length of a cylindrical second section. A ridge can form a ring around all or a portion of a second cylindrical section. A ridge can be any of a variety of shapes or sizes.

Second Shelf

A one way valve can have a second shelf that extends inward and downward from the base of a second cylindrical section (see e.g., FIG. 2A (126)). A second shelf can be configured to cover a flow outlet on a manual air pump when the manual air pump is not compressed to prevent a powdered therapeutic formulation from moving upstream into the manual air pump.

Second Shelf Length

The shortest length of the surface of a second shelf from the base of the second cylindrical section to the bottom of the one way valve can be about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5 mm. The shortest length of the surface of a second shelf from the base of the second cylindrical section to the bottom of the one way valve more than about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5 mm. The shortest length of the surface of a second shelf from the base of the second cylindrical section to the bottom of the one way valve less than about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5 mm. The shortest length of the surface of a second shelf from the base of the second cylindrical section to the bottom of the one way valve about 0.1 to 5 mm, 0.1 to 4 mm, 0.1 to 3 mm, 0.1 to 2 mm, 0.1 to 1.75 mm, 0.1 to 1.5 mm, 0.1 to 1.25 mm, or 0.1 to 1 mm.

Second Shelf Angle

An angle formed between the side of the second cylindrical section and the surface of the second shelf can be between about 0 to 90 degrees, 10 to 80 degrees, 20 to 70 degrees, 30 to 60 degrees, or 40 to 50 degrees. An angle formed between the side of the second cylindrical section and the surface of the second shelf can be about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90 degrees. An angle formed between the side of the second cylindrical section and the surface of the second shelf can be more than about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90 degrees. An angle formed between the side of the second cylindrical section and the surface of the second shelf can be less than about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90 degrees. An angle formed between the side of the second cylindrical section and the surface of the second shelf can be an acute angle or a right angle.

Base of a One Way Valve

A one way valve can be configured to have a base that is wider than the width of a second cylindrical section. In some embodiments, a base does not touch a nozzle pipe when a device is activated or when a device is not activated.

Alternative Configurations

In some embodiments, a one way valve has a top section, first cylindrical section, first shelf, second cylindrical section, and a second shelf or a base. In other embodiments, the one way valve need not have all such sections. For example, a one way valve can be formed of a single cylinder or other shape that rests on a vial throat in its unactivated position and is positioned beneath a nozzle shoulder. The one way valve may have one or more slit or passageway that is blocked by the vial throat when the one way valve is resting on the vial throat. When a manual pump is compressed, the one way valve can be pushed upward against the nozzle shoulder in its activated position, and air may flow through the one or more slit or passageway that is not blocked by the nozzle shoulder into the nozzle.

The one way valve can have any shape with one or more sections that can allow the one way valve to rest on the vial throat and not fall into the vial. The one way valve can have any shape with one or more sections that can allow the one way valve to move upwards a limited amount to a second position when activated. In some embodiments, the one way valve is limited in its upward movement by a nozzle shoulder or other shaped feature of the nozzle. The one way valve can have one or more fluid flow passageway (e.g., slit, channel, groove, tunnel, tube) that is not in fluid communication with the air or gas source when the one way valve is in an inactivated position. In some embodiments, the fluid flow passageway is blocked by the nozzle shoulder directly, or the fluid communication is blocked by a portion of the one way valve resting on the vial shoulder. The fluid flow passageway can provide fluid communication between the air or gas source and the interior of the nozzle when the one way valve is in an activated position. The fluid flow passageway can be positioned so as not to be blocked by the nozzle shoulder when the one way valve is in an activated or inactivated position.

One Way Valve Operation

A one way valve can be configured to adopt a first position and a second position in a device (e.g., compare FIG. 1 and FIG. 3). In some embodiments, the first position is a closed configuration which prevents the flow of air from an air source, and in some embodiments, through a flow outlet, and/or throat. In some embodiments, the first position further prevents the flow of air into a nozzle and/or powdered therapeutic reservoir. In some embodiments, a moveable valve in the first position is configured such that air cannot flow from a flow outlet and therapeutic formulation cannot flow upstream from a reservoir into an air source. In some embodiments, a one way valve in the first position is in communication with a flow outlet such that air cannot flow from a flow outlet into an air source. In some embodiments, the one way valve is held in the first position by gravity. Alternatively, the one way valve can be held in the first position by a biasing force. The biasing force can be provided by a compressible mechanism or tension mechanism. The biasing force can be provided by a spring, elastic, plastic foam, or rubber portion. In some embodiments, the second position of a valve disk is an open configuration which allows the flow of air from an air source, out of a flow outlet, and through a flow passage and/or powdered therapeutic reservoir.

The movement of a one way valve from the first position to the second position can be reversible, such as by gravity, pressure, airflow, a lever or spring mechanism, or a combination thereof. In other embodiments, the movement of a one way valve from the first position to the second position is not reversible or not readily reversible. In some embodiments, the position of a one way valve can be regulated by a pressure differential between the pressure of air or other propellant at a flow outlet and the pressure of air or other propellant in a reservoir. In some embodiments, a one way valve can be configured to remain in the second position in the presence of a sufficient flow or velocity of air from an air source and move to the first configuration in the absence of a sufficient flow or velocity of air from an air source.

C. Air Source

A device described herein can comprise an air source. An air source can be configured to provide a flow of air or other propellant or a combination thereof through a powdered therapeutic formulation reservoir, out of a nozzle and into a nostril or nasal cavity of a subject. An air source can be configured to provide a flow of air past a valve which regulates the flow of air into a nozzle or reservoir.

An air source can be composed of a variety of polymers, plastics, rubber, silicones, metal, composites, any other materials described herein as suitable for use in the manufacture of a device applicator, or any other material suitable for use as an applicator air source. An air source can be made of one material or type of material. Alternatively, an air source can be composed two or more different materials or types of materials. In some embodiments, all or a portion of an air source can be a biocompatible material, or a hypoallergenic material. An air source can be composed of rigid, substantially rigid, flexible, or substantially flexible materials, or a combination thereof. In some embodiments, an air source is comprised of one or more of silicone, acrylates, polyethylenes, polyurethane, polyurethane, hydrogel, polyester (e.g., DACRONB from E. I. Du Pont de Nemours and Company, Wilmington, Del.), polypropylene, polytetrafluoroethylene (PTFE), expanded PTFE (ePTFE), polyether ether ketone (PEEK), nylon, extruded collagen, polymer foam, rubber, silicone rubber, polyethylene terephthalate, ultra high molecular weight polyethylene, polycarbonate urethane, polyurethane, polyimides, aluminum, stainless steel, nickel-titanium alloy (e.g., Nitinol), titanium, stainless steel, or cobalt-chrome alloy (e.g., ELGILOYB from Elgin Specialty Metals, Elgin, Ill.; CONICHROMEB from Carpenter Metals Corp., Wyomissing, Pa.).

An air source can be one of a variety of air sources suitable for use in a nasal applicator such as, for example, air sources described in U.S. Patent Application Nos. US20090025720, US20090064997, US20080819617, US20080161771, US20080289629, US20080142018, US20070129665, US20060219240, US20060024185, US20060254585, US20040187868, US20040149289, US20040112378, US20020174865; U.S. Pat. No. 3,856,185, U.S. Pat. No. 4,017,007, U.S. Pat. No. 4,200,099, U.S. Pat. No. 5,046,493, U.S. Pat. No. 5,683,361, U.S. Pat. No. 5,702,362, U.S. Pat. No. 6,488,648, U.S. Pat. No. 6,824,080, U.S. Pat. No. 6,866,039, U.S. Pat. No. 6,938,798, U.S. Pat. No. 6,186,141, U.S. Pat. No. 6,345,737, U.S. Pat. No. 6,585,172, U.S. Pat. No. 6,543,448, U.S. Pat. No. 6,089,228, U.S. Pat. No. 6,427,680, U.S. Pat. No. 6,644,305, U.S. Pat. No. 6,494,204, U.S. Pat. No. 6,290,667, U.S. Pat. No. 7,481,218, international patent applications nos. WO2002/00282, WO2005/000477, WO2008/026730, WO2007/102089, WO1990/07351, and WO/2003/000310, European Patent Nos. EP1673123, and EP1390091, and Japanese Patent and Application Nos. JP2006122189, JP2001095918, JP3678955, JP11226127, JP3488624, JP11221280, JP11197245, JP3547605, JP10028735, JP9248342, JP09028805, JP08322934, JP08280808, JP8206208, JP8103499, and JP8071152, all of which are herein incorporated by reference in their entireties.

An air source can be a pressurized container. In some embodiments, a pressurized container contains air or other propellant such as one or more of a low molecular weight hydrocarbon such as butane or propane, dimethyl ether, methyl ethyl ether, nitrous oxide, carbon dioxide, nitrogen, a hydrofluorocarbon, compressed air, a chlorofluorocarbon, or a hydrofluoroalkane such as for example, 1,1,2,-tetrafluoroethane or 1,1,1,2,3,3,3-heptafluoropropane. A pressurized container can contain between about 0.1 g of propellant and about 5 g of propellant including at least about 4 g, 3 g, 2 g, 1.5 g, 1 g, 0.75 g, 0.5 g, 0.25 g, 0.2 g, or about 0.1 g of propellant. A pressurized container can be configured to contain a propellant at a maximum pressure of at least about 1.5 atm, 2 atm, 2.5 atm, 3 atm, 3.5 atm, 4 atm, 4.5 atm, 5 atm, 5.5 atm, 6 atm, 7 atm, 8 atm, 9 atm, 10 atm, 11 atm, or about 12 atm. In some embodiments, a pressurized container can be configured to contain a propellant at a maximum pressure of between about 2 atm and about 10 atm, 3 atm and about 9 atm, 4 atm and about 8 atm, 4 atm and about 7 atm, or between about 4 atm and about 6 atm.

A pressurized container can be activated to release propellant by any means known in the art. For example a pressure valve can engage an air source to release propellant upon the application of a compressive force, or a lever can engage an air source to release propellant upon movement of the lever. In another example, a pressurized container can be activated to release propellant in response to a digital or analog signal. For example, a user can push a button which controls the release of propellant such as by controlling a servo motor or a microprocessor controlled valve. In some embodiments, a container can be activated by a mechanism that detects nasal inhalation. For example, a lever or other sensing means such as a pressure sensor can be activated by positioning a device as described herein into the nostril of a subject and the inhalation of the subject. A pressurized container can be configured to release a controlled or metered amount of propellant each time a container is activated. In other embodiments, a pressurized container can continue to release propellant until a user has ceased to provide an activation input.

An air source can be a pump such as an electric pump or a manual pump. An air source can comprise an inner container slidably disposed within an outer container. Movement of one or more of inner and outer containers by manual or other means can provide a flow of air out of an air source and into a flow passage. Inner and outer containers of a pump can be configured to return to a resting state in the absence of an external compressive force, such as for example through the action of a spring or other return mechanism. In another example, a pump comprises a slidable piston. A piston can be actuated by manual or electric means. Movement of a piston by manual or other means can provide a flow of air out of an air source and into a flow passage. A piston can be configured to return to a resting state in the absence of an external force, such as for example through the action of a spring or other return mechanism.

A pump can comprise a deformable volume. For example, a pump can comprise a plastic, rubber or other deformable material. A pump can also comprise an articulated volume such that accordion-like folds allow compression of a pump to deliver air. A deformable volume can be compressed by for example one or more fingers, (e.g., between a thumb and a forefinger, middle finger, ring finger, little finger) or combination or by one or more hands. Alternatively, a deformable volume can be compressed by electronic or hydraulic means. In some embodiments, a deformable volume is compressed such as by application of a squeezing or other compressive force and can revert to a non-compressed shape upon release of the compressive force. In some embodiments, the reversion to a non-compressed shape can be provided by an inherent elastomeric force of the shape and materials of a deformable volume. The reversion can be assisted by a spring or other energy return mechanism.

An air source can be any shape suitable for use in a device described herein, including but not limited to a sphere, an ellipsoid, a cylinder, a cuboid, a frustum, or any other suitable shape such as any of the shapes described herein, or a combination thereof. The upstream to downstream length of an air source can be less than about 10 cm, 9 cm, 8 cm, 7 cm, 6 cm, 5 cm, 4.5 cm, 4 cm, 3.5 cm, 3 cm, or 2 cm. In some embodiments, the length of an air source can be between about 2 cm and 10 cm, between about 2 cm and 8 cm, between about 2 cm and 5 mm, between about 4 cm and 10 cm, or between about 4 cm and 6 cm. The upstream to downstream length of an air source can be at least 1 cm, 2 cm, 3 cm, 4 cm, 5 cm, 6 cm, 7 cm, 8 cm, 9 cm, or 10 cm. The upstream to downstream length of an air source can be about 1 cm, 2 cm, 3 cm, 4 cm, 5 cm, 6 cm, 7 cm, 8 cm, 9 cm, or 10 cm.

In some embodiments, the width perpendicular to the upstream to downstream axis of an air source at its widest section is less than 1 cm, 1.5 cm, 2 cm, 2.5 cm, 3 cm, 3.5 cm, 4 cm, 4.5 cm, 5 cm, 6 cm, 7 cm, 8 cm, 9 cm, 10 cm, 12 cm, 15 cm, or 20 cm wide. The width perpendicular to the upstream to downstream axis of an air source at its widest section can be at least 1 cm, 1.5 cm, 2 cm, 2.5 cm, 3 cm, 3.5 cm, 4 cm, 4.5 cm, 5 cm, 6 cm, 7 cm, 8 cm, 9 cm, 10 cm, 12 cm, 15 cm, or 20 cm wide. The width perpendicular to the upstream to downstream axis of an air source at its widest section can be 1 cm, 1.5 cm, 2 cm, 2.5 cm, 3 cm, 3.5 cm, 4 cm, 4.5 cm, 5 cm, 6 cm, 7 cm, 8 cm, 9 cm, 10 cm, 12 cm, 15 cm, or 20 cm wide.

In some embodiments, an air source has a volume that is less than 10 cm$^3$, 9 cm$^3$, 8 cm$^3$, 7 cm$^3$, 6 cm$^3$, 5 cm$^3$, 4 cm$^3$, 3 cm$^3$, 2 cm$^3$, or 1 cm$^3$. In some embodiments, an air source comprises a volume of between about 1 cm$^3$ and about 10 cm$^3$, or between about 2 cm$^3$ and about 10 cm$^3$, 2 cm$^3$ and about 7 cm$^3$, or 4 cm$^3$ and about 8 cm$^3$. An air source can have a volume more than 10 cm$^3$, 9 cm$^3$, 8 cm$^3$, 7 cm$^3$, 6 cm$^3$, 5 cm$^3$, 4 cm$^3$, 3 cm$^3$, 2 cm$^3$, or 1 cm$^3$. An air source can have a volume of about 10 cm$^3$, 9 cm$^3$, 8 cm$^3$, 7 cm$^3$, 6 cm$^3$, 5 cm$^3$, 4 cm$^3$, 3 cm$^3$, 2 cm$^3$, or 1 cm$^3$.

An air source can be configured to deliver between about 1 mL to about 10 mL of air or other propellant to a nostril of a subject during a single activation. An air source can be configured to deliver between about 1 mL to about 10 mL of air or other propellant to a powdered therapeutic reservoir of a device during a single activation. In some embodiments, an air source is configured to deliver at least 1 mL, 2 mL, 3 mL, 4 mL, 5 mL, 6 mL, 7 mL, 8 mL, 9 mL, or 10 mL of air or other propellant to a nostril of a subject or to a reservoir of a device. In some instances, an air source is configured to deliver between 1 least 1 mL and 10 mL, 1 mL and 8 mL, 1 mL and 5 mL, 2 mL and 10 mL, 2 mL and 8 mL, 2 mL and 7 mL, 2 mL and 6 mL, 2 mL and 5 mL, 3 mL and 10 mL or 3 mL and 8 mL of air or other propellant to a nostril of a subject or to a reservoir of a device. An air source can be configured to deliver less than 1 mL, 2 mL, 3 mL, 4 mL, 5 mL, 6 mL, 7 mL, 8 mL, 9 mL, or 10 mL of air or other propellant to a nostril of a subject or to a reservoir of a device. An air source can be configured to deliver about 1 mL, 2 mL, 3 mL, 4 mL, 5 mL, 6 mL, 7 mL, 8 mL, 9 mL, or 10 mL of air or other propellant to a nostril of a subject or to a reservoir of a device. An air source can be configured to be activated by a force of between about 5 kPa and 100 kPa. An air source can be configured to be activated by a force of less than about 5 kPa, 6 kPa, 7 kPa, 8 kPa, 9 kPa, 10 kPa, 11 kPa, 12 kPa, 13 kPa, 14 kPa, 15 kPa, 16 kPa, 17 kPa, 18 kPa, 19 kPa, 20 kPa, 21 kPa, 22 kPa, 23 kPa, 24 kPa, 25 kPa, 26 kPa, 28 kPa, 30 kPa, 32 kPa, 33 kPa, 35 kPa, 38 kPa, 40 kPa, 42 kPa, 45 kPa, 48 kPa, or 50 kPa of pressure. An air source can be configured to provide a pressure of air or other propellant at a flow outlet of about 1 kilopascals to about 100 kilopascals, about 2 kilopascals to about 50 kilopascals, about 4 kilopascals to about 40 kilopascals, about 5 kilopascals to about 35 kilopascals, or about 10 to about 30 kilopascals.

Flow Inlet

An air source can comprise a flow inlet for filling of an air source with air or other propellant. In some embodiments, a flow inlet is in communication with an air source and with an outside environment. A flow inlet can further comprise a valve or other means for regulating the flow of air through a flow inlet. In some embodiments, a flow inlet can be configured to provide a unidirectional flow of air from the outside of an air source towards the inside of an air source. In some embodiments, a flow inlet is configured to provide for a movement from a compressed form of an air source provided by application of a compressive force and a non-compressed form of an air source provided by release of the compressive force. For example, application of compressive force by manual squeezing of an air source can provide for movement of air from an air source through a flow outlet and ultimately out of a nozzle, while, releasing of compressive force provides for movement of air into an air source via a flow inlet which in part or in whole provides for a return of an air source to a non-compressed state.

A flow inlet can be any of a number of shapes including but not limited to a cone, a cylinder, tapered cylinder, a frustum, and a parallelepiped or any other shape provided herein, including a combination of one or more of the shapes provided herein. In some embodiments, the width or diameter of a flow inlet is correlated to the width or diameter of a flow outlet. For example, the width or diameter of a flow inlet can be configured to be less than 1%, 2%, 2%, 4%, 5%, 6%, 8%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 55%, 60%, 65%, 70%, 75%, 80%, or 90% of the width or diameter of a flow outlet. In some case, the size of a flow inlet is correlated to the size of a flow outlet. For example, the size of a flow inlet can be configured to be more than 1%, 2%, 2%, 4%, 5%, 6%, 8%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 55%, 60%, 65%, 70%, 75%, 80%, or 90% of the size of a flow outlet.

The diameter of a flow inlet can be between about 0.05 and 2 mm, about 0.05 mm and 1 mm, about 0.05 and 0.5 mm, about 0.05 and 0.1 mm. The diameter of a flow inlet can be about 0.05, 0.06, 0.07, 0.08, 0.09, 0.1, 0.15, 0.2, 0.25, 0.3, 0.35, 0.4, 0.45, 0.5, 0.55, 0.6, 0.65, 0.7, 0.75, 0.8, 0.85, 0.9, 1, 1.1, 1.2, 1.3, 1.4, 1.5, 1.6, 1.7, 1.8, 1.9, and 2 mm. The diameter of a flow inlet can be more than about 0.05, 0.06, 0.07, 0.08, 0.09, 0.1, 0.15, 0.2, 0.25, 0.3, 0.35, 0.4, 0.45, 0.5, 0.55, 0.6, 0.65, 0.7, 0.75, 0.8, 0.85, 0.9, 1, 1.1, 1.2, 1.3, 1.4, 1.5, 1.6, 1.7, 1.8, 1.9, and 2 mm. The diameter of a flow inlet can be less than about 0.05, 0.06, 0.07, 0.08, 0.09, 0.1, 0.15, 0.2, 0.25, 0.3, 0.35, 0.4, 0.45, 0.5, 0.55, 0.6, 0.65, 0.7, 0.75, 0.8, 0.85, 0.9, 1, 1.1, 1.2, 1.3, 1.4, 1.5, 1.6, 1.7, 1.8, 1.9, and 2 mm.

A flow inlet can be on an air source. A flow inlet can be located in the throat of an air source. In some embodiments, a nozzle hole can also be a flow inlet.

Flow Outlet

A flow outlet can be configured to provide a pressure of between about 1 kilopascals to about 100 kilopascals, about 2 kilopascals to about 50 kilopascals, about 4 kilopascals to about 40 kilopascals or about 5 kilopascals to about 35 kilopascals. A flow outlet can be any of a number of shapes including but not limited to a cone, a cylinder, tapered cylinder, a frustum, and a parallelepiped or any other shape provided herein, including a combination of one or more shapes.

In some embodiments, the upstream to downstream length of a flow outlet is less than about 20 mm, less than about 15 mm, less than about 10 mm, less than about 8 mm, less than about 7 mm, less than about 6 mm, less than about 5 mm, less than about 4 mm, or less than about 3 mm. In some embodiments, the length of a flow outlet is between about 3 mm and 20 mm, between about 3 mm and 15 mm, between about 3 mm and 10 mm, or between about 5 mm and 10 mm. A flow outlet can be about 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 mm in length. In some embodiments, the width perpendicular to the upstream to downstream axis of a flow outlet at its widest section is between about 5 mm and about 20 mm, or about 5 mm and 15 mm. In some embodiments, the width perpendicular to the upstream to downstream axis of a flow outlet at its widest section is at least about 5 mm, 6 mm, 7 mm, 8 mm, 9 mm, 10 mm, 11 mm, 12 mm, 13 mm, 14 mm, 15 mm, or 20 mm wide. In some embodiments, the width perpendicular to the upstream to downstream axis of a flow outlet at its narrowest is less than about 4 mm, 5 mm, 6 mm, 7 mm, 8 mm, 9 mm, 10 mm, 11 mm, 12 mm, 13 mm, 14 mm, 15 mm, or 20 mm wide. The width perpendicular to the upstream to downstream axis of a flow outlet at its widest section can be about 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, 26 mm, 27 mm, 28 mm, 29 mm, or 30 mm.

One Way Valve for Airtight Apparatus

In some embodiments, the one way valve can be configured to minimize or prevent exposure of the powder formulation to air and moisture, which can result in increased stability of a powder formulation pre-filled in the device or reservoir when the device does not contain an air inlet or when the device is a closed system. The valve can be made by a more simplified manufacturing process of the parts of the device and can result in better cost effectiveness.

The valve can be a one way valve for the powder formulation and a two way valve for air. The valve can be configured to allow the exit of a powdered therapeutic formulation from the nozzle and allow exit of air from the pump from the nozzle and allow entry of air from the outside environment through the nozzle, which can allow air to enter into the pump. This can allow for repeated activation of the device without the need for a flow inlet in the pump of the device.

In some embodiments, the device can be an airtight container or a closed system, for example there can be no inlets or holes in the device, for example the pump, when the removable or breakable cover is in place or has not been removed. In some embodiments the pump does not comprise an air inlet. A device comprising an air inlet in the pump (as described above) can access the outside air. Air can escape from within the device through the air inlet in the pump when the pump is activated in such a device. This loss of air through the air inlet in the pump during activation of the pump can lead to a less than maximal amount of air from within the pump being used to expel the therapeutic formulation from the device. In a device without an air inlet in the pump, there is no air from within the pump lost to the environment through an air inlet. This prevention of air loss in the pump during activation of the pump can lead to the maximal amount of air within the pump being used to expel the therapeutic formulation from the device. In some embodiments, all air that has been squeezed out of the pump upon activation of the pump in a device lacking an air inlet in the pump can act to propel the therapeutic formulation. This device design (no air inlet in the pump) enables for a reduction in the pump volume and a smaller device compared to a device with an air inlet in the pump. The reduced pump volume size and reduced device size can decrease manufacturing costs and increasing portability of the device lacking an air inlet in the pump compared to a device with an air inlet in the pump.

In some embodiments, when the removable or breakable cover is in place or has not been removed, there is no communication with an air source and with the outside environment. In some embodiments, when the removable or breakable cover is removed the device can comprise a flow inlet. In some embodiments, the flow inlet can comprise the nozzle hole when the removable or breakable cover is removed. The nozzle hole (flow inlet) can be adapted to allow the exit of a powdered therapeutic formulation from the nozzle as a single stream. In some embodiments, the nozzle has multiple holes (flow inlets) that can emit a powdered therapeutic formulation as multiple streams that remain separate or that can combine into a single stream when the device is activated. In some embodiments, the nozzle hole is disposed at the downstream end of the nozzle. In some embodiments, the nozzle hole is also the downstream end of the flow restrictor. A nozzle hole can be any of a number of shapes including but not limited to a circle, oval, triangle, rectangle, or combination thereof.

In some embodiments, a one way valve is configured to block movement of powdered therapeutic formulation (e.g., by gravity) in an upstream direction (e.g., into an air source). A one way valve can be configured so it can be in one position in the device when the device is not activated (e.g., an air source is not activated) and another position in the device when the device is activated (e.g., an air source is activated). A one way valve can be configured to block movement of a powdered therapeutic formulation (e.g., by gravity) in an upstream direction (e.g., into a flexible vial and/or manual air pump) when the device is not activated (e.g., a manual air pump is not compressed) and when the device is activated (e.g., a manual air pump is compressed).

A one way valve can be configured to regulate the flow of air from an air source and into a nozzle of a device. A one way valve can further be configured to regulate the movement of a powdered therapeutic formulation. A one way valve can be configured to block air or gas flow from an air source into a nozzle when the device is not activated (e.g., a manual air pump is not compressed) and can permit air or gas flow from an air source into a nozzle when the device is activated (e.g., a manual air pump is compressed).

In some embodiments the one way valve can be configured to allow movement of air from the outside environment in an upstream direction (e.g., into a flexible vial and/or manual air pump) when the device is being deactivated (e.g., a manual air pump is being decompressed) and in a downstream direction when the device is activated (e.g., a manual air pump is compressed). The decompression of the pump can pull air from the outside environment through the nozzle hole (e.g., flow inlet) and into the nozzle reservoir, through the valve cavity, and into the pump.

In some embodiments, a nozzle hole (flow inlet) can be configured to provide a bidirectional flow of air from the outside of an air source towards the inside of an air source and from the inside of an air source toward the outside of an air source. In some embodiments, a nozzle hole or flow inlet is configured to provide for a movement from a compressed form of an air source provided by application of a compressive force and a non-compressed form of an air source provided by release of the compressive force. For example, application of compressive force by manual squeezing of an air source can provide for movement of air from an air source through a flow outlet and ultimately out of a nozzle. Releasing of compressive force can provide for movement of air into an air source via a flow inlet (nozzle hole), through a cavity in the valve, and the flow outlet, which in part or in whole provides for a return of an air source to a non-compressed state. For example, when the compressive force is released, air from the outside environment moves into the air source (e.g., pump) via the nozzle hole (flow inlet), into the nozzle reservoir, through a cavity spanning internally through the valve, and into the air source.

The one way valve can contain slits (or channels or grooves) diagonal to a major axis of the device that can create a vortex along the walls of the reservoir when the device is activated.

Devices described herein can be more fully understood by reference to the figures provided herein. FIG. 9 illustrates a cross-sectional view of a single-use intranasal delivery device. The intranasal delivery device (900) can comprise air source, which can be a flexible vial (902). The flexible vial can function as a manual air pump (904). The flexible vial can comprise a flow outlet (906) and does not comprise a flow inlet when the removable or breakable cover (934) has not been removed. The flow inlet can comprise the nozzle hole (932), which can act as a flow inlet when the removable or breakable cover (934) has been removed. The flexible vial can comprise a throat (908) at the top of the flexible vial with a narrower diameter than the bottom of the flexible vial (910). The throat (908) can comprise an external thread (912) for attachment of a nozzle (914).

A one way valve (916) can sit on a surface in the throat (908) of the flexible vial (902) and block the flow outlet (906) when the device is not activated (e.g., when the manual air pump is not compressed). Resting of the one way valve (916) on a surface in the throat (908) can prevent a powdered therapeutic composition (M) from entering the flexible vial (902) when the device is not activated.

A one way valve (916) can comprise an inner inlet section (944), a valve cavity (946), a top section (918), a first cylindrical section (920), a first shelf (922), a second cylindrical section (924), and a second shelf (926). In some embodiments, the top section comprises the inner inlet section. In some embodiments, the valve does not comprise a top section. One or more slits (928) can be in the surface of the first shelf. One or more slits (928) can permit flow of air or gas from the flexible vial (902) to the nozzle (914) when the manual air pump (904) is compressed (see e.g., FIGS. 11A-11B). Embodiments of the one way valve (916) are depicted in FIGS. 10A-10F.

An intranasal device (900) can further comprise a nozzle (914) that can comprise a nozzle pipe (930) which can be inserted or partially inserted into the nasal cavity or a nostril of a subject. The nozzle (914) can further comprise a removable or breakable cover (934), a nozzle hole (932), which can act as a flow inlet when the removable or breakable cover is removed, and a reservoir for a powdered therapeutic formulation (938). The reservoir for the powdered therapeutic formulation can comprise a powdered therapeutic formulation (M). The nozzle (914) can comprise a base (940) that can comprise an internal thread (942) for attachment to the throat (908) of the flexible vial (902). The internal thread of the nozzle base can mate with an external tread of the vial throat.

FIGS. 10A-10F illustrate different views of embodiments of a one way valve (916) that correspond to the one way valve (916) illustrated in FIG. 9. FIG. 10A illustrates a side view of a one way valve (916) with the top of the one way valve pointing to the left. In this embodiment, the one way valve comprises an inner inlet section (944), a valve cavity (946), a top section (918), extending from the base of the inner inlet section (944), and a first cylindrical section (920) extending from the base of the top section (918). At the base of the first cylindrical section is a first shelf (922) that extends outward and downward from the base of the first cylindrical section (920). Illustrated here is a single slit (928) on the top of the first shelf (922), and the slit lies at a non 90 degree angle relative to either edge of the shelf. The first shelf can have multiple slits. The inner inlet section (944) can be connected to the top of the top section. The inner inlet section (944) can comprise an opening in connection with the reservoir for a powdered therapeutic formulation (938). In some embodiments, the inner inlet section (944) the can be hollow. In some embodiments, the inner inlet section (944) can comprise part of the valve cavity (946). The bottom of the top section can be connected to the top of a first shelf (922). The bottom of the first shelf can connect to the top of a second cylindrical section (924). The bottom of the second cylindrical section can connect to a second shelf (926) that can extend inward and downward relative to the bottom of the second cylindrical section (924). In some embodiments, the one way valve can be integrally formed as a single piece. For example, a top section, first cylindrical section, first shelf, second cylindrical section, and second shelf can be integrally formed as a single piece. Alternatively, one or more parts of the one way valve can be formed separately.

In some embodiments, the inner inlet section (944) forms the top (upstream section) of the valve cavity (946). The valve cavity can comprise two openings. The two openings can comprise an upstream opening and a downstream opening. In some embodiments, the upstream opening is in connection with a reservoir for a powdered therapeutic formulation (938). In some embodiments, the downstream opening is in connection with the pump (904). In some embodiments, the upstream opening extends upstream into a valve to form a valve cavity (946), which can extend through the valve to the second upstream opening and into the pump. The valve cavity can extend from the downstream opening of the inner inlet section (944) connected to the reservoir for a powdered therapeutic formulation (938) through the valve to the downstream opening connected to the pump. The valve cavity can connect the two openings such that a hollow space is formed within the valve and can allow air to pass through in both directions. The valve cavity can form a hollow space through a top section, a first and second shelf, and a first and second cylindrical section of a valve to form a continuous cavity therethrough. In some embodiments, the valve cavity extends from the opening in the inner inlet section (944) and extends to form a hollow channel or cavity through the entire length of the valve into the manual air pump (904). An inner inlet section disclosed herein is not limited to a particular shape. An inner inlet section can be of a uniform width such as in the shape of a cylinder, a cuboid, a rhombohedron, or a parallelepiped. An inner inlet section can also be a funnel or frustum shape, with a wide end and a narrow end. The shape of an inner inlet section can be wider at the upstream end and narrower at the downstream end. An inner inlet section can be wider at the downstream end and narrower at the upstream end.

FIG. 10B illustrates a cross-sectional view of the one way valve along a plane AA of FIG. 2A as viewed from the right of the one way valve (916) depicted in FIG. 10A. The cross-sectional view illustrates multiple indentations (928) around the perimeter of the first shelf of the one way valve that correspond to slits (928). The circle in the middle (936) illustrates that the one way valve (916) can be hollow. In other embodiments, the one way valve can be solid. In other embodiments, the one way valve is not hollow.

FIG. 10C illustrates a cross-sectional view along the plane of BB of FIG. 10A as viewed from the bottom and left of the one way valve illustrated in FIG. 10A. A slit is illustrated (928).

FIGS. 10D-10F illustrate cross-sectional views of a portion of a one way valve along a plane AA as in FIG. 10A as viewed from the right of the one way valve depicted in FIG. 10A. Different geometries for slits that can be formed in the top shelf of the one way valve of FIG. 10A are illustrated. The geometry of the slit in this view can be formed by a curved surface (FIG. 10D), by two surfaces (FIG. 10E), or by 3 surfaces (FIG. 10F). The cross-sectional geometry of the slit can be curved, angled, or any combination thereof.

FIG. 11A illustrates an activated configuration of the intranasal delivery device illustrated in FIG. 9 and the flow path of air or gas from the manual air pump (904) to the nozzle (914). FIG. 11B illustrates a deactivated configuration of the intranasal delivery device illustrated in FIG. 9 and the flow path of air or gas from the outside environment through the nozzle hole (932), into the reservoir for a powdered therapeutic formulation (938), through the inner inlet section (944), through the valve cavity (946), and into the manual air pump (904). The removable or breakable cover (934) is removed from the intranasal delivery device (900). A one way valve (916) can be resting on the surface of a vial throat (908). To activate the device, a user compresses the flexible vial (902) (compression is illustrated by the arrows and the deformed flexible vial relative to the vial in FIG. 9) that serves as a manual air pump (904). Air flows out the flow outlet (906) of the flexible vial (902). The air flow causes the one way valve (916) to rise in the nozzle (914). When the one way valve (916) rises in the nozzle it may no longer be resting on the vial throat (908). The non-slit portions of the first shelf (922) of the one way valve contact the nozzle pipe (930) to prevent a powdered therapeutic formulation from moving upstream into the flexible vial (902). Air travels around the second shelf (926) of the one way valve (916) and the second cylindrical section (924) of the one way valve (916) and flows through the slit (928) in the first shelf (922) of the one way valve (916). The air then flows between the first cylindrical section (920) and the nozzle pipe (930) into the reservoir (938) and forces the powdered therapeutic formulation (M) up the nozzle pipe (930) and out the nozzle hole (932). The air also travels through the valve cavity (946) and into the reservoir (938). After activation of the device, the pump is then decompressed. Upon decompression of the pump, air from the outside environment is pulled through the nozzle hole (flow inlet) and into the reservoir (938). The air flows into the opening of the inner inlet section and through the valve cavity and through the second opening of the valve cavity into the pump resulting in recompression of the pump.

Inner Inlet Section Length

The length of an inner inlet section can be measured from an upstream end to a downstream end, where upstream and downstream denote the direction of flow of air or other propellant during operation of a device (i.e. air or other propellant can flow from upstream to downstream). The length of an inner inlet section can be the length of a reservoir for a powdered therapeutic formulation (938). The length of an inner inlet section can be the length of a nozzle pipe. The length of an inner inlet section can be at most about the length from the top (upstream end) of a valve top section to the base (downstream end) of a nozzle hole. The length of the inner inlet section can be at least about the length from the top (upstream end) of a valve top section to a length above the height (upstream end) of a powdered therapeutic formulation when a powdered therapeutic formulation is present in the powdered therapeutic formulation reservoir (938). The length of the inner inlet section can be at least about the length from the top (upstream) of a valve top section to a length such that the powdered formulation in the reservoir (938) cannot enter into the pump when the pump is activated or deactivated. The length of the inner inlet section can be at least about the length from the top (upstream) of a valve top section to a length such that the powdered formulation in the reservoir (938) cannot enter into or be pulled into the pump when the device is deactivated, or when there is negative pressure in the device.

The upstream to downstream length of an inner inlet section can be less than about 5 cm, less than about 4.5 cm, less than about 4 cm, less than about 3.5 cm, less than about 3 cm, less than about 2.5 cm, less than about 2 cm, less than about 1.5 cm, less than about 1.0 cm, or less than about 0.5 cm. The length of the inner inlet section can be between about 0.5 cm and 5 cm, between about 1 cm and 5 cm, between about 1 cm and 4 cm, between about 1 cm and 3 cm, between about 2 cm and 5 cm, or between about 2 cm and 4 cm in length. The length of the inner inlet section can be about 0.5 cm, 1 cm, 1.5 cm, 2 cm, 2.5 cm, 3 cm, 3.5 cm, 4 cm, 4.5 cm, or 5 cm. The length of the inner inlet section can be more than about 0.5 cm, 1 cm, 1.5 cm, 2 cm, 2.5 cm, 3 cm, 3.5 cm, 4 cm, 4.5 cm, or 5 cm.

External Inner Inlet Section Width

In some embodiments, the external width perpendicular to the upstream to downstream axis of the inner inlet section at its widest section is between about 0.01 cm to 0.2 cm, 0.01 cm to about 0.15 cm, 0.01 cm to about 0.1 cm, 0.01 cm to about 0.05 cm, 0.02 cm to 0.2 cm, 0.02 cm to about 0.15 cm, 0.02 cm to about 0.1 cm, 0.02 cm to about 0.05 cm, 0.03 cm to 0.2 cm, 0.03 cm to about 0.15 cm, 0.03 cm to about 0.1 cm, 0.03 cm to about 0.05 cm, 0.04 cm to 0.2 cm, 0.04 cm to about 0.15 cm, 0.04 cm to about 0.1 cm, or 0.04 cm to about 0.05 cm. In some embodiments, the external width perpendicular to the upstream to downstream axis of the inner inlet section at its widest section is no more than about 0.01 cm, 0.02 cm, 0.03 cm, 0.04 cm, 0.05 cm, 0.06 cm, 0.07 cm, 0.08 cm, 0.09 cm, 0.1 cm, 0.11 cm, 0.12 cm, 0.13 cm, 0.14 cm, 0.15 cm, 0.16 cm, 0.17 cm, 0.18 cm, 0.19 cm, 0.2 cm, 0.3 cm, or 0.4 cm wide. In some embodiments, the external width perpendicular to the upstream to downstream axis of the inner inlet section at its widest section is about 0.01 cm, 0.02 cm, 0.03 cm, 0.04 cm, 0.05 cm, 0.06 cm, 0.07 cm, 0.08 cm, 0.09 cm, 0.1 cm, 0.11 cm, 0.12 cm, 0.13 cm, 0.14 cm, 0.15 cm, 0.16 cm, 0.17 cm, 0.18 cm, 0.19 cm, 0.2 cm, 0.3 cm, or 0.4 cm wide. In some embodiments, the external width perpendicular to the upstream to downstream axis of the inner inlet section at its widest section is more than about 0.01 cm, 0.02 cm, 0.03 cm, 0.04 cm, 0.05 cm, 0.06 cm, 0.07 cm, 0.08 cm, 0.09 cm, 0.1 cm, 0.11 cm, 0.12 cm, 0.13 cm, 0.14 cm, 0.15 cm, 0.16 cm, 0.17 cm, 0.18 cm, 0.19 cm, 0.2 cm, 0.3 cm, or 0.4 cm wide.

In some embodiments, the external width perpendicular to the upstream to downstream axis of the inner inlet section at its narrowest section is no more than about 0.01 cm, 0.02 cm, 0.03 cm, 0.04 cm, 0.05 cm, 0.06 cm, 0.07 cm, 0.08 cm, 0.09 cm, 0.1 cm, 0.11 cm, 0.12 cm, 0.13 cm, 0.14 cm, 0.15 cm, 0.16 cm, 0.17 cm, 0.18 cm, 0.19 cm, 0.2 cm, 0.3 cm, or 0.4 cm. In some embodiments, the external width perpendicular to the upstream to downstream axis of the inner inlet section at its narrowest section lies within the range of 00.01 cm to 0.2 cm, 0.01 cm to about 0.15 cm, 0.01 cm to about 0.1 cm, 0.01 cm to about 0.05 cm, 0.02 cm to 0.2 cm, 0.02 cm to about 0.15 cm, 0.02 cm to about 0.1 cm, 0.02 cm to about 0.05 cm, 0.03 cm to 0.2 cm, 0.03 cm to about 0.15 cm, 0.03 cm to about 0.1 cm, 0.03 cm to about 0.05 cm, 0.04 cm to 0.2 cm, 0.04 cm to about 0.15 cm, 0.04 cm to about 0.1 cm, or 0.04 cm to about 0.05 cm. In some embodiments, the external width perpendicular to the upstream to downstream axis of the inner inlet section at its narrowest section is about 0.01 cm, 0.02 cm, 0.03 cm, 0.04 cm, 0.05 cm, 0.06 cm, 0.07 cm, 0.08 cm, 0.09 cm, 0.1 cm, 0.11 cm, 0.12 cm, 0.13 cm, 0.14 cm, 0.15 cm, 0.16 cm, 0.17 cm, 0.18 cm, 0.19 cm, 0.2 cm, 0.3 cm, or 0.4 cm. In some embodiments, the external width perpendicular to the upstream to downstream axis of the inner inlet section at its narrowest section is more than about 0.01 cm, 0.02 cm, 0.03 cm, 0.04 cm, 0.05 cm, 0.06 cm, 0.07 cm, 0.08 cm, 0.09 cm, 0.1 cm, 0.11 cm, 0.12 cm, 0.13 cm, 0.14 cm, 0.15 cm, 0.16 cm, 0.17 cm, 0.18 cm, 0.19 cm, 0.2 cm, 0.3 cm, or 0.4 cm.

The width of the inner inlet section can vary continuously, can vary in a step-wise fashion, does not vary, or a combination thereof. The inner width or the outer width of the inner inlet section can vary continuously, can vary in a step-wise fashion, does not vary, or a combination thereof. The upstream and downstream ends of the inner inlet section can be the same width or different. In some embodiments, the widest and narrowest sections of an inner inlet section are at the ends (i.e., the top (upstream) of the valve top section and the upstream opening of the valve cavity (946)). For example, the widest section of an inner inlet section can be at the upstream end and the narrowest section of the inner inlet section can be at the downstream end, or vice versa. In some embodiment, the widest and/or narrowest sections of an inner inlet section are not at the end. In some embodiments, the widest section of an inner inlet section is an inner inlet section base for attachment to a valve top section (918).

Internal Inner Inlet Section Width

In some embodiments, the internal width perpendicular to the upstream to downstream axis of the inner inlet section at its widest section is between about 0.001 cm to 0.2 cm, 0.001 cm to about 0.15 cm, 0.001 cm to about 0.1 cm, 0.001 cm to about 0.06 cm, 0.001 cm to about 0.05 cm, 0.005 cm to 0.2 cm, 0.005 cm to about 0.15 cm, 0.005 cm to about 0.1 cm, 0.005 cm to about 0.06 cm, 0.005 cm to about 0.05 cm, 0.01 cm to 0.2 cm, 0.01 cm to about 0.15 cm, 0.01 cm to about 0.1 cm, 0.01 cm to about 0.06 cm, 0.01 cm to about 0.05 cm, 0.015 cm to 0.2 cm, 0.015 cm to about 0.15 cm, 0.015 cm to about 0.1 cm, 0.015 cm to about 0.06 cm, 0.015 cm to about 0.05 cm, 0.02 cm to 0.2 cm, 0.02 cm to about 0.15 cm, 0.02 cm to about 0.1 cm, 0.02 cm to about 0.06 cm, or 0.02 cm to about 0.05 cm. In some embodiments, the internal width perpendicular to the upstream to downstream axis of the inner inlet section at its widest section is no more than about 0.001 cm, 0.002 cm, 0.003 cm, 0.004 cm, 0.005 cm, 0.006 cm, 0.007 cm, 0.008 cm, 0.009 cm, 0.01 cm, 0.015 cm, 0.02 cm, 0.025 cm, 0.03 cm, 0.035 cm, 0.04 cm, 0.045 cm, 0.05 cm, 0.055 cm, 0.06 cm, 0.065 cm, 0.07 cm, 0.075 cm, 0.08 cm, 0.085 cm, 0.09 cm, 0.095 cm, 0.1 cm, 0.11 cm, 0.12 cm, 0.13 cm, 0.14 cm, 0.15 cm, 0.16 cm, 0.17 cm, 0.18 cm, 0.19 cm, or 0.2 cm wide. In some embodiments, the internal width perpendicular to the upstream to downstream axis of the inner inlet section at its widest section is more than about 0.001 cm, 0.002 cm, 0.003 cm, 0.004 cm, 0.005 cm, 0.006 cm, 0.007 cm, 0.008 cm, 0.009 cm, 0.01 cm, 0.015 cm, 0.02 cm, 0.025 cm, 0.03 cm, 0.035 cm, 0.04 cm, 0.045 cm, 0.05 cm, 0.055 cm, 0.06 cm, 0.065 cm, 0.07 cm, 0.075 cm, 0.08 cm, 0.085 cm, 0.09 cm, 0.095 cm, 0.1 cm, 0.11 cm, 0.12 cm, 0.13 cm, 0.14 cm, 0.15 cm, 0.16 cm, 0.17 cm, 0.18 cm, 0.19 cm, or 0.2 cm wide. In some embodiments, the internal width perpendicular to the upstream to downstream axis of the inner inlet section at its widest section is about 0.001 cm, 0.002 cm, 0.003 cm, 0.004 cm, 0.005 cm, 0.006 cm, 0.007 cm, 0.008 cm, 0.009 cm, 0.01 cm, 0.015 cm, 0.02 cm, 0.025 cm, 0.03 cm, 0.035 cm, 0.04 cm, 0.045 cm, 0.05 cm, 0.055 cm, 0.06 cm, 0.065 cm, 0.07 cm, 0.075 cm, 0.08 cm, 0.085 cm, 0.09 cm, 0.095 cm, 0.1 cm, 0.11 cm, 0.12 cm, 0.13 cm, 0.14 cm, 0.15 cm, 0.16 cm, 0.17 cm, 0.18 cm, 0.19 cm, or 0.2 cm wide.

In some embodiments, the internal width perpendicular to the upstream to downstream axis of the inner inlet section at its narrowest section is no more than about 0.001 cm, 0.002 cm, 0.003 cm, 0.004 cm, 0.005 cm, 0.006 cm, 0.007 cm, 0.008 cm, 0.009 cm, 0.01 cm, 0.015 cm, 0.02 cm, 0.025 cm, 0.03 cm, 0.035 cm, 0.04 cm, 0.045 cm, 0.05 cm, 0.055 cm, 0.06 cm, 0.065 cm, 0.07 cm, 0.075 cm, 0.08 cm, 0.085 cm, 0.09 cm, 0.095 cm, 0.1 cm, 0.11 cm, 0.12 cm, 0.13 cm, 0.14 cm, 0.15 cm, 0.16 cm, 0.17 cm, 0.18 cm, 0.19 cm, or 0.2 cm wide. In some embodiments, the internal width perpendicular to the upstream to downstream axis of the inner inlet section at its narrowest section is more than about 0.001 cm, 0.002 cm, 0.003 cm, 0.004 cm, 0.005 cm, 0.006 cm, 0.007 cm, 0.008 cm, 0.009 cm, 0.01 cm, 0.015 cm, 0.02 cm, 0.025 cm, 0.03 cm, 0.035 cm, 0.04 cm, 0.045 cm, 0.05 cm, 0.055 cm, 0.06 cm, 0.065 cm, 0.07 cm, 0.075 cm, 0.08 cm, 0.085 cm, 0.09 cm, 0.095 cm, 0.1 cm, 0.11 cm, 0.12 cm, 0.13 cm, 0.14 cm, 0.15 cm, 0.16 cm, 0.17 cm, 0.18 cm, 0.19 cm, or 0.2 cm wide. In some embodiments, the internal width perpendicular to the upstream to downstream axis of the inner inlet section at its narrowest section lies within the range of 0.001 cm to 0.2 cm, 0.001 cm to about 0.15 cm, 0.001 cm to about 0.1 cm, 0.001 cm to about 0.06 cm, 0.001 cm to about 0.05 cm, 0.005 cm to 0.2 cm, 0.005 cm to about 0.15 cm, 0.005 cm to about 0.1 cm, 0.005 cm to about 0.06 cm, 0.005 cm to about 0.05 cm, 0.01 cm to 0.2 cm, 0.01 cm to about 0.15 cm, 0.01 cm to about 0.1 cm, 0.01 cm to about 0.06 cm, 0.01 cm to about 0.05 cm, 0.015 cm to 0.2 cm, 0.015 cm to about 0.15 cm, 0.015 cm to about 0.1 cm, 0.015 cm to about 0.06 cm, 0.015 cm to about 0.05 cm, 0.02 cm to 0.2 cm, 0.02 cm to about 0.15 cm, 0.02 cm to about 0.1 cm, 0.02 cm to about 0.06 cm, or 0.02 cm to about 0.05 cm. In some embodiments, the internal width perpendicular to the upstream to downstream axis of the inner inlet section at its narrowest section is about 0.001 cm, 0.002 cm, 0.003 cm, 0.004 cm, 0.005 cm, 0.006 cm, 0.007 cm, 0.008 cm, 0.009 cm, 0.01 cm, 0.015 cm, 0.02 cm, 0.025 cm, 0.03 cm, 0.035 cm, 0.04 cm, 0.045 cm, 0.05 cm, 0.055 cm, 0.06 cm, 0.065 cm, 0.07 cm, 0.075 cm, 0.08 cm, 0.085 cm, 0.09 cm, 0.095 cm, 0.1 cm, 0.11 cm, 0.12 cm, 0.13 cm, 0.14 cm, 0.15 cm, 0.16 cm, 0.17 cm, 0.18 cm, 0.19 cm, or 0.2 cm wide.

Internal Volume of Inner Inlet Section

The inner inlet section can be hollow and can contain an internal volume. The internal volume of an inner inlet section can be about 0.0001 $cm^3$ or more, 0.0005 $cm^3$ or more, 0.001 $cm^3$ or more, 0.005 $cm^3$ or more, 0.01 $cm^3$ or more, 0.02 $cm^3$ or more, or 0.03 $cm^3$ or more. In some embodiments, the internal volume of an inner inlet section is between about 0.0001 $cm^3$ and about 0.03 $cm^3$, between about 0.0001 $cm^3$ and about 0.02 $cm^3$, between about 0.0001 $cm^3$ and about 0.01 $cm^3$, between about 0.0001 $cm^3$ and about 0.005 $cm^3$, between about 0.0001 $cm^3$ and about 0.001 $cm^3$, between about 0.0001 $cm^3$ and about 0.0005 $cm^3$, between about 0.0005 $cm^3$ and about 0.03 $cm^3$, between about 0.0005 $cm^3$ and about 0.02 $cm^3$, between about 0.0005 $cm^3$ and about 0.01 $cm^3$, between about 0.0005 $cm^3$ and about 0.005 $cm^3$, between about 0.0005 $cm^3$ and about 0.001 $cm^3$, between about 0.001 $cm^3$ and about 0.03 $cm^3$, between about 0.001 $cm^3$ and about 0.02 $cm^3$, between about 0.001 $cm^3$ and about 0.01 $cm^3$, between about 0.001 $cm^3$ and about 0.005 $cm^3$, between about 0.005 $cm^3$ and about 0.03 $cm^3$, between about 0.005 $cm^3$ and about 0.02 $cm^3$, between about 0.005 $cm^3$ and about 0.01 $cm^3$, between about 0.01 $cm^3$ and about 0.03 $cm^3$, or between about 0.01 $cm^3$ and about 0.02 $cm^3$. The internal volume of the inner inlet section can be about 0.0001 $cm^3$, 0.0002 $cm^3$, 0.0003 $cm^3$, 0.0004 $cm^3$, 0.0005 $cm^3$, 0.0006 $cm^3$, 0.0007 $cm^3$, 0.0008 $cm^3$, 0.0009 $cm^3$, 0.001 $cm^3$, 0.002 $cm^3$, 0.003 $cm^3$, 0.004 $cm^3$, 0.005 $cm^3$, 0.006 $cm^3$, 0.007 $cm^3$, 0.008 $cm^3$, 0.009 $cm^3$, 0.011 $cm^3$, 0.012 $cm^3$, 0.013 $cm^3$, 0.014 $cm^3$, 0.015 $cm^3$, 0.016 $cm^3$, 0.017 $cm^3$, 0.018 $cm^3$, 0.019 $cm^3$, 0.02 $cm^3$, 0.021 $cm^3$, 0.022 $cm^3$, 0.023 $cm^3$, 0.024 $cm^3$, 0.025 $cm^3$, 0.026 $cm^3$, 0.027 $cm^3$, 0.028 $cm^3$, 0.029 $cm^3$, 0.03 $cm^3$, 0.04 $cm^3$, 0.05 $cm^3$, 0.06 $cm^3$, 0.07 $cm^3$, 0.08 $cm^3$, 0.09 $cm^3$, or 1.0 $cm^3$. The internal volume of the inner inlet section can be more than about 0.0001 $cm^3$, 0.0005 $cm^3$, 0.001 $cm^3$, 0.005 $cm^3$, 0.01 $cm^3$, 0.02 $cm^3$, or 0.03 $cm^3$. The internal volume of the inner inlet section can be less than about 0.0001 $cm^3$, 0.0005 $cm^3$, 0.001 $cm^3$, 0.005 $cm^3$, 0.01 $cm^3$, 0.02 $cm^3$, or 0.03 $cm^3$.

Throat Ring

A flow outlet of an air source can be located in the throat of the air source (e.g., manual air pump and/or vial). A manual air pump or vial can contain a throat ring in a throat of the manual air pump of vial. A throat ring can be fused to the throat of a manual air pump or vial. A throat ring can be inserted into the throat of a manual air pump or vial. A throat ring can be configured to restrict the width of the throat of a manual air pump or vial. An opening in a throat ring can be of a width narrower than the widest width of a one way valve.

The width of a hole formed by a throat ring can be about 1 to 20 mm, 1 to 10 mm, 1 to 7.5 mm, or 1 to 5 mm. The width of a hole formed by a throat ring can be about 1, 2, 3, 4, 5, 6, 7, 8, 9, 10, 11, 12, 13, 14, 15, 16, 17, 18, 19, or 20 mm. The width of a hole formed by a throat ring can be more than about 1, 2, 3, 4, 5, 6, 7, 8, 9, 10, 11, 12, 13, 14, 15, 16, 17, 18, 19, or 20 mm. The width of a hole formed by a throat ring can be less than about 1, 2, 3, 4, 5, 6, 7, 8, 9, 10, 11, 12, 13, 14, 15, 16, 17, 18, 19, or 20 mm.

The diameter of a throat ring can be about 1 to 20 mm, 1 to 17.5 mm, 1 to 15 mm, 1 to 12.5 mm, 1 to 10 mm, 1 to 7.5 mm, or 1 to 5 mm. The diameter of a throat ring can be about 1, 2, 3, 4, 5, 6, 7, 8, 9, 10, 11, 12, 13, 14, 15, 16, 17, 18, 19, or 20 mm. The diameter of a throat ring can be more than about 1, 2, 3, 4, 5, 6, 7, 8, 9, 10, 11, 12, 13, 14, 15, 16, 17, 18, 19, or 20 mm. The diameter of a throat ring can be less than about 1, 2, 3, 4, 5, 6, 7, 8, 9, 10, 11, 12, 13, 14, 15, 16, 17, 18, 19, or 20 mm.

The height of a throat ring can be about 1 to 20 mm, 1 to 17.5 mm, 1 to 15 mm, 1 to 12.5 mm, 1 to 10 mm, 1 to 7.5 mm, or 1 to 5 mm. The height of a throat ring can be about 1, 2, 3, 4, 5, 6, 7, 8, 9, 10, 11, 12, 13, 14, 15, 16, 17, 18, 19, or 20 mm. The height of a throat ring can be more than about 1, 2, 3, 4, 5, 6, 7, 8, 9, 10, 11, 12, 13, 14, 15, 16, 17, 18, 19, or 20 mm. The height of a throat ring can be less than about 1, 2, 3, 4, 5, 6, 7, 8, 9, 10, 11, 12, 13, 14, 15, 16, 17, 18, 19, or 20 mm. The height of a throat ring can be the same or different as the height of a throat of a manual air pump or vial.

A throat ring thickness (distance inner to outer edge of a throat ring) can be about 0.1 to 20 mm, 0.1 to 15 mm, 0.1 to 10 mm, 0.1 to 7.5 mm, 0.1 to 5 mm, or 0.1 to 2.5 mm. A throat ring thickness (distance from inner to outer edge of a throat ring) can be about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5 5.6, 5.7, 5.8, 5.9, 6, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, or 10 mm. A throat ring thickness (distance from inner to outer edge of a throat ring) can be more than about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5 5.6, 5.7, 5.8, 5.9, 6, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, or 10 mm. A throat ring thickness (distance from inner to outer edge of a throat ring) can be less than about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5 5.6, 5.7, 5.8, 5.9, 6, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, or 10 mm.

A throat ring can be composed of a variety of polymers, plastics, rubber, silicones, metal, composites, any other materials described herein as suitable for use in the manufacture of an intranasal delivery device, or any other material suitable for use in an intranasal delivery device. A throat ring can be made of one material or type of material. Alternatively, a throat ring can be composed two or more different materials or types of materials. All or a portion of a throat ring can be a biocompatible material or a hypoallergenic material. A throat ring can be composed of rigid, substantially rigid, flexible, or substantially flexible materials, or a combination thereof. In some embodiments, a throat ring can be comprised of one or more of paper, silicone, acrylates, polyethylenes, polyurethane, polyurethane, hydrogel, polyester (e.g., DACRONB from E. I. Du Pont de Nemours and Company, Wilmington, Del.), polypropylene, polytetrafluoroethylene (PTFE), expanded PTFE (ePTFE), polyether ether ketone (PEEK), nylon, extruded collagen, polymer foam, rubber, silicone rubber, polyethylene terephthalate, ultra high molecular weight polyethylene, polycarbonate urethane, polyurethane, polyimides, aluminum, stainless steel, nickel-titanium alloy (e.g., Nitinol), titanium, stainless steel, or cobalt-chrome alloy (e.g., ELGILOYB from Elgin Specialty Metals, Elgin, Ill.; CONICHROMEB from Carpenter Metals Corp., Wyomissing, Pa.).

The devices disclosed herein can be utilized for the delivery of any composition which can be delivered intranasally. For example, the devices can be used for dry powder formulations of a pharmaceutical, a neutraceutical or other desired compound.

Methods

Provided herein are methods for delivering a powdered therapeutic formulation to a subject with an intranasal delivery device described herein. A drug can be loaded to a nozzle, and the nozzle with the drug can be attached to an air source. If the intranasal delivery device contains a cover, for example, a removable or breakable cover or a cap, the cover can be removed from the intranasal delivery device. The removal can be by breaking, lifting, twisting, pressing, or turning the cover. When the device is not activated, a one way valve can rest on the surface of a vial throat to prevent the powdered therapeutic from moving upstream into an air source (e.g., a flexible vial). The nozzle can be inserted or partially inserted in a nostril of a subject. The user can insert the device or another person (e.g., a health care provider) can insert the device in a nostril of the subject. A device can be activated (e.g., by compressing an air source that is a flexible vial, by activating a pressurized air source). Air can flow out a flow outlet of an air source and cause the one way valve to rise in the nozzle of the device. When the one way valve rises in the nozzle it may no longer be resting on the vial throat. The non-slit portions of a one way valve can contact the nozzle pipe to prevent a powdered therapeutic formulation from moving upstream into the air source. Air can travel around parts of the one way valve and flow over slits in the one way valve. The air can then flow into a reservoir and force the powdered therapeutic formulation up a nozzle pipe, out a nozzle hole, and into the nostril of the subject. FIG. 3 illustrates an intranasal delivery device that has been activated.

Air Flow in the Reservoir

As illustrated in the partial view of the embodiment of the device in FIG. 6, a powdered therapeutic formulation can be found along the internal wall of the nozzle (Y) and between the one way valve (116) and the internal wall of the nozzle (Z). The one way valve can be adapted to permit spinning airflow in the reservoir when the air source is activated. For example, one or more slits (128) in the one way valve can be diagonally oriented to create spinning air flow when the device is activated, and the spinning airflow can take the powder away from the internal wall of the nozzle.

FIGS. 7A and 7B illustrate differences in access of air flow along the internal wall of the nozzle and along the surface of the one way valve (700) when the slits on the first shelf (730) of the one way valve (700) are non-diagonal (FIG. 7A, 740) and when the slits are diagonal (FIG. 7B, 750). Shown in FIGS. 7A and 7B is the top section (710), first cylindrical section (720), and part of the first shelf (730) of a one way valve (700). When the one or more slits on the first shelf (730) are non-diagonal (FIG. 7A, 740), there are areas (760) on the internal wall of the nozzle that air flow may not reach when the air source is activated. There are also areas (762) along the first cylindrical section (720) where air flow may not reach when the air source is activated. Also shown is area representing the internal surface of the nozzle where the air flow will reach (764) when the air source is activated.

When the one or more slits on the first shelf are diagonal (FIG. 7B, 750), air flow can access the entire internal wall of the nozzle (768) downstream from the first cylindrical section (720) of the one way valve. The area along the first cylindrical section (720) where the air flow may not reach (766) is minimized relative to if the one or more slits are non-diagonal on the first shelf (e.g., compare the area of 766 in FIG. 7B to the area of 762 in FIG. 7A). Devices with diagonal slits in the first shelf of the one-way valve can have increased delivery of a powdered therapeutic formulation that resides between the internal wall of the nozzle and the one-way valve when the air source is activated relative to devices with non-diagonal slits in the first shelf of the one way valve.

FIGS. 8A and 8B illustrate differences in access of air flow along the one way valve (800) when the slits in the first shelf (830) are non-diagonal (FIG. 8A, 840) and when the slits are diagonal (FIG. 8B, 850). When the one or more slits on the first shelf are diagonal (FIG. 8B, 850), the area along the first cylindrical section (820) where the air flow may not reach (862) is minimized relative to if the one or more slits are non-diagonal on the first shelf (e.g., compare the area of 860 in FIG. 8A to the area of 862 in FIG. 7B). Devices with diagonal slits in the first shelf of the one-way valve can have increased delivery of a powdered therapeutic formulation the resides between the internal wall of the nozzle and the one-way valve when the air source is activated relative to devices with non-diagonal slits in the first shelf of the one way valve.

Assembly

A powdered therapeutic formulation can be loaded into a nozzle. The nozzle can have a cap, removable or breakaway cover, etc. A nozzle can then be coupled to an air source. The nozzle can be coupled to the air source by, for example, screwing the nozzle to the air source, clipping the nozzle to the air source, snapping the nozzle to the air source, etc.

II. Compositions

A device described herein is suitable for delivering therapeutic agents including, but not limited to, free-base and salt forms of the agents. A therapeutic agent can be in crystalline or amorphous forms. A powdery therapeutic formulation can consist of just the therapeutic agent "carrier free" or they can further comprise a suitable carrier, filler, diluent, excipient, permeation enhancers, solubilizers and adjuvants or other material.

A device described herein can protect the powdered therapeutic formulation from moisture or air until a device is prepared for use. A device can be prepared for use by removing or breaking off of a protective cover. Anhydrous compositions can be provided in a reservoir and a device can further be packaged using materials known to prevent exposure to humidity or water such that they can be included in suitable formulary kits. Examples of suitable packaging include, but are not limited to, hermetically sealed foils, plastic or the like, unit dose containers, blister packs, and strip packs.

Pharmaceutical Kits

A pharmaceutical kit is provided for use of a therapeutic compositions described herein. In some embodiments, a kit comprising a unit dosage of a dry powder formulation suitable for intranasal administration and an intranasal delivery device or dispenser is provided. In some embodiments, a therapeutic composition is present in a therapeutic quantity. In some embodiments, kits include a carrier, package, or container that is compartmentalized to receive one or more blister packs, bottles, tubes, capsules, and the like. In certain embodiments, a pharmaceutical composition is presented in a pack or dispenser device which contains one or more unit dosage forms containing a compound provided herein. In other embodiments, a pack contains metal or plastic foil, such as a blister pack. In some embodiments, a pack contains capsules, cartridges, vials, or tubes. In other embodiments, a pack or dispenser device is accompanied by instructions for administration. In some embodiments, a dispenser is disposable or single use, while in other embodiments, a dispenser is reusable. In certain embodiments, a pharmaceutical formulation is preloaded into a device. In some embodiments, nasal applicator has a volume of not more than about 3 mL, 5 mL, 10 mL, 15 mL, 20 mL, 30 mL, 40 mL, or 50 mL.

In some embodiments, a pack or dispenser also accompanied with a notice as required by a governmental agency regulating the manufacture, use, or sale of pharmaceuticals. This notice states that a drug is approved by the agency for human or veterinary administration. Such notice, for example, is a labeling approved by the U.S. Food and Drug Administration for prescription drugs, or an approved product. Compositions containing a compound provided herein formulated in a compatible pharmaceutical carrier are also prepared, placed in an appropriate container, and labeled for treatment of an indicated condition.

The articles of manufacture provided herein can also contain an intranasal administration or dispensing device. A device can rely on the patient's inspiration to transport a formulation or pumps can be provided or built into devices to assist the aerosolization and transport of a formulation. Alternatively, a propellant can be included with or it can be stored within devices.

Such kits optionally comprise an identifying description or label for containers. In further embodiments, a label is on a container with letters, numbers or other characters forming the label and attached, molded or etched into a container itself; a label is associated with a container when it is present within a receptacle or carrier that also holds the container, e.g., as a package insert. In some embodiments, a label is used to indicate that the contents are to be used for a specific therapeutic application. In yet other embodiments, a label also indicates directions for use of the contents, such as in methods described herein. A set of instructions can also be included, generally in the form of a package insert. An informational material can contain instructions on how to dispense the pharmaceutical composition, including description of the type of patients who can be treated, the schedule (e.g., dose and frequency), and the like.

EXAMPLES

Example 1. Single Use of a Device to Deliver a Therapeutic to a Subject

A device is positioned by a user whereby a nozzle of a device is at least partially positioned within a nostril of a subject. The user compresses an air source between the thumb and forefinger with approximately 25 kPa of force. A powdered therapeutic formulation residing in a reservoir disposed within the nozzle of the device is delivered into the nostril of the subject. The user visually inspects the nozzle and ascertains that a sufficient amount of the therapeutic has exited a nozzle and been delivered.

Example 2. Use of a Device to Deliver a Single Dose of a Therapeutic to a Subject A device is positioned by a user whereby a nozzle of a device is at least partially positioned within a nostril of a subject. The user compresses an air source between the thumb and forefinger. A one way valve moves from a first position to a second position in the device, and air moves over the surface of slits in the one way valve into a reservoir containing a therapeutic formulation. The powdered therapeutic formulation residing in the reservoir disposed within a nozzle of the device is delivered into the nostril of the subject. The user visually inspects the nozzle and ascertains that a sufficient amount of the therapeutic has not exited the nozzle and been delivered. The user repeats compression of the air source until visual inspection reveals that a sufficient amount of the therapeutic has exited the nozzle and been delivered.

Example 3: Intranasal Delivery Device

FIG. 1 illustrates a cross-sectional view of a single-use intranasal delivery device. The intranasal delivery device (100) can comprise air source, which can be a flexible vial (102). The flexible vial can function as a manual air pump (104). The flexible vial can comprise a flow inlet (not shown) and a flow outlet (106). The flexible vial can comprise a throat (108) at the top of the flexible vial with a narrower diameter than the bottom of the flexible vial (110). The throat (108) can comprise an external thread (112) for attachment of a nozzle (114).

A one way valve (116) can sit on a surface in the throat (108) of the flexible vial (102) and block the flow outlet (106) when the device is not activated (e.g., when the manual air pump is not compressed). Resting of the one way valve (116) on a surface in the throat (108) can prevent a powdered therapeutic composition (M) from entering the flexible vial (102) when the device is not activated.

A one way valve (116) can comprise a top section (118), a first cylindrical section (120), a first shelf (122), a second cylindrical section (124), and a second shelf (126). One or more slits (128) can be in the surface of the first shelf. One or more slits (128) can permit flow of air or gas from the flexible vial (102) to the nozzle (114) when the manual air pump (104) is compressed (see e.g., FIG. 3). Embodiments of the one way valve (116) are depicted in FIGS. 2A-2F.

An intranasal device (100) can further comprise a nozzle (114) that can comprise a nozzle pipe (130) which can be inserted or partially inserted into the nasal cavity or a nostril of a subject. The nozzle (114) can further comprise a nozzle hole (132), a removable or breakable cover (134), and a reservoir for a powdered therapeutic formulation (138). The reservoir for the powdered therapeutic formulation can comprise a powdered therapeutic formulation (M). The nozzle (114) can comprise a base (140) that can comprise an internal thread (142) for attachment to the throat (108) of the flexible vial (102).

Example 4: One Way Valve

FIGS. 2A-2F illustrate different views of embodiments of a one way valve (116) that correspond to the one way valve (116) illustrated in FIG. 1. FIG. 2A illustrates a side view of a one way valve (116) with the top of the one way valve pointing to the left. In this embodiment, the one way valve comprises a top section (118) and a first cylindrical section (120) extending from the base of the top section (118). At the base of the first cylindrical section is a first shelf (122) that extends outward and downward from the base of the first cylindrical section (120). Illustrated here is a single slit (128) on the top of the first shelf (122), and the slit lies at a non 90 degree angle relative to either edge of the shelf. The first shelf can have multiple slits. The bottom of the first shelf connects to the top of a second cylindrical section (124). The bottom of the second cylindrical section connects to a second shelf (126) that can extend inward and downward relative to the bottom of the second cylindrical section (124).

FIG. 2B illustrates a cross-sectional view of the one way valve along a plane AA of FIG. 2A as viewed from the right of the one way valve (116) depicted in FIG. 2A. The cross-sectional view illustrates multiple indentations (128) around the perimeter of the first shelf of the one way valve that correspond to slits (128). The circle in the middle (136) illustrates that the one way valve (116) can be hollow.

FIG. 2C illustrates a cross-sectional view along the plane of BB of FIG. 2A as viewed from the bottom and left of the one way valve illustrated in FIG. 2A. A slit is illustrated (128).

FIGS. 2A-2F illustrate cross-sectional views of a portion of a one way valve along a plane AA of FIG. 2A as viewed from the right of the one way valve depicted in FIG. 2A. Different geometries for slits that can be formed in the top shelf of the one way valve of FIG. 2A are illustrated. The geometry of the slit in this view can be formed by a curved surface (FIG. 2D), by two surfaces (FIG. 2E), or by 3 surfaces (FIG. 2F).

Example 5: Activated Intranasal Delivery Device

FIG. 3 illustrates an activated configuration of the intranasal delivery device illustrated in FIG. 1 and the flow path of air or gas from the manual air pump (104) to the nozzle (114). The removable or breakable cover (134) is removed from the intranasal delivery device (100). A user compresses the flexible vial (102) (compression is illustrated by the arrows and the deformed flexible vial relative to the vial in FIG. 1) that serves as a manual air pump (104). Air flows out the flow outlet (106) of the flexible vial (102). The air flow causes the one way valve (116) to rise in the nozzle (114). The non-slit portions of the first shelf (122) of the one way valve contact the nozzle pipe (130) to prevent a powdered therapeutic formulation from moving upstream into the flexible vial (102). Air travels around the second shelf (126) of the one way valve (116) and the second cylindrical section (124) of the one way valve (116) and flows through the slit (128) in the first shelf (122) of the one way valve (116). The air then flows between the first cylindrical section (120) and the nozzle pipe (130) into the reservoir (138) and forces the powdered therapeutic formulation (M) up the nozzle pipe (130) and out the nozzle hole (132).

Example 6. Delivery Devices: Single-Use Device

Intranasal formulation is delivered into the nasal cavity using an intranasal delivery device described herein. An intranasal delivery device described herein, an air-driven device, is designed for intranasal delivery of TRG. As shown in FIG. 1, powder formulation is pre-filled in the device. Upon use, the plastic tab or an airtight cap is removed, as shown in FIG. 3, thereby clearing the pathway of the powder formulation, allowing the intranasal formulation to be released. Once the plastic tab or an airtight cap is removed from an applicator described herein, patients can manually pump a device easily, and deliver the intranasal formulation through the single nozzle of a device into the nasal cavity. Intranasal formulation is administered into the nasal cavity using an intranasal delivery device described herein. The shape and secondary particle size of intranasal formulation powder emitted from an applicator described herein are analyzed to evaluate the delivery characteristics of intranasal formulation powder generated in combination with an intranasal delivery device described herein.

While preferred embodiments have been shown and described herein, it will be obvious to those skilled in the art that such embodiments are provided by way of example only. Numerous variations, changes, and substitutions will now occur to those skilled in the art without departing from devices, methods and compositions described herein. It should be understood that various alternatives to the embodiments of described herein can be employed in practicing devices, methods and compositions described herein. It is intended that the following claims define the scope of methods, compositions and devices and that methods, compositions, and devices within the scope of these claims and their equivalents be covered thereby.

What is claimed is:

1. A device that comprises:
   a) a nozzle having an upstream end and a downstream end adapted to allow positioning of at least a portion of the nozzle into a nostril of a subject;
   b) a reservoir comprising a single dose of a powdered therapeutic formulation, wherein the reservoir has an upstream end and a downstream end, and is an integral part of the nozzle;
   c) a valve having an upstream end and a downstream end, wherein:
      1) the valve is adapted to cause diffusion of the powdered therapeutic formulation when the device is activated, and
      2) the valve comprises a conical top section that is connected to a first cylindrical section, wherein the first cylindrical section is connected to a first shelf that is connected to a second cylindrical section, and wherein the first shelf comprises at least one slit; and
   d) an air source operably linked to the upstream end of the valve, wherein the air source comprises a manual air pump, and
   wherein the device is a single-use device.

2. The device of claim 1, wherein the at least one slit is adapted to permit an air flow from the air source to the nozzle when the air source is engaged.

3. The device of claim 1, wherein the device is adapted to deliver between 80% and 99% of the single dose of the powdered therapeutic formulation into the nostril of the subject after one or more activations of the air source.

4. The device of claim 1, wherein the at least one slit lies at a 45 degree angle relative to an edge of the first shelf.

5. The device of claim 1, wherein the first shelf comprises about 3-20 slits.

6. The device of claim 1, wherein the first shelf comprises about 8 slits.

7. The device of claim 1, wherein the valve comprises an inner inlet section that is connected to the conical top section.

8. The device of claim 1, wherein the valve is partially located within a nozzle pipe of the nozzle.

9. The device of claim 8, wherein the conical top section and the first cylindrical section of the valve are located within the nozzle pipe; or wherein the second cylindrical section of the valve is not located within the nozzle pipe.

10. The device of claim 8, wherein the first shelf contacts the nozzle pipe when the air source is activated.

11. The device of claim 1, wherein the valve comprises an inner inlet section that is connected to the first cylindrical section.

12. The device of claim 1, wherein the valve comprises a valve cavity.

13. The device of claim 12, wherein the valve cavity spans the entire length of the valve.

14. The device of claim 1, wherein the air source further comprises a flow outlet.

15. The device of claim 14, wherein the air source further comprises a flow inlet that is from 0.1 to 2 mm in diameter; or less than 10% of a size of the flow outlet.

16. The device of claim 1, wherein the reservoir comprises an inner diameter of less than 10 mm.

17. A method of delivering a powdered therapeutic formulation, the method comprising positioning the nozzle of the device of claim 1 into the nostril of the subject and activating the air source.

18. The device of claim 1, wherein the at least one slit is in the surface of the first shelf of the valve and is adapted to create a vortex in the reservoir when the device is activated.

19. A method of manufacturing a device for delivering a powdered therapeutic formulation to a subject, wherein the method comprises providing the powdered therapeutic formulation to a reservoir and subsequently coupling a nozzle to an air source, and wherein the device comprises:
   a) the nozzle having an upstream end and a downstream end, the nozzle adapted to allow positioning of at least a portion of the nozzle into a nostril of the subject;
   b) the reservoir comprising a dose of the powdered therapeutic formulation and having an upstream end and a downstream end, wherein the reservoir is an integral part of the nozzle;
   c) a valve having an upstream end and a downstream end, wherein:
      1) the valve is adapted to cause diffusion of the powdered therapeutic formulation when the device is activated, and
      2) the valve comprises a conical top section that is connected to a first cylindrical section, wherein the first cylindrical section is connected to a first shelf that is connected to a second cylindrical section, and wherein the first shelf comprises at least one slit; and
   d) the air source operably linked to the upstream end of the valve, wherein the air source comprises a manual air pump.

20. The method of claim 19, wherein the at least one slit is in the surface of the first shelf of the valve and is adapted to create a vortex in the reservoir when the device is activated.

* * * * *